(12) United States Patent
Li et al.

(10) Patent No.: US 9,227,944 B2
(45) Date of Patent: *Jan. 5, 2016

(54) DOPAMINE D3 RECEPTOR LIGANDS AND PREPARATION AND MEDICAL USES OF THE SAME

(71) Applicant: INSTITUTE OF PHARMACOLOGY AND TOXICOLOGY ACADEMY OF MILITARY MEDICAL SCIENCE P.L.A. CHINA, Beijing (CN)

(72) Inventors: Jin Li, Beijing (CN); Rifang Yang, Beijing (CN); Rui Song, Beijing (CN); Hui Zhu, Beijing (CN); Ning Wu, Beijing (CN); Liuhong Yun, Beijing (CN); Ruibin Su, Beijing (CN); Rusheng Zhao, Beijing (CN)

(73) Assignee: INSTITUTE OF PHARMACOLOGY AND TOXICOLOGY ACADEMY OF MILITARY SCIENCE P.L.A. CHINA, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/294,721

(22) Filed: Jun. 3, 2014

(65) Prior Publication Data
US 2014/0329831 A1  Nov. 6, 2014

Related U.S. Application Data

(63) Continuation-in-part of application No. 13/123,368, filed as application No. PCT/CN2009/001096 on Sep. 28, 2009, now Pat. No. 8,829,001.

(30) Foreign Application Priority Data

Oct. 10, 2008  (CN) .......................... 2008 1 0167089

(51) Int. Cl.
| C07D 263/58 | (2006.01) |
| A61K 31/496 | (2006.01) |
| C07D 277/68 | (2006.01) |
| C07D 413/12 | (2006.01) |
| C07D 417/12 | (2006.01) |

(52) U.S. Cl.
CPC ............ *C07D 277/68* (2013.01); *C07D 263/58* (2013.01); *C07D 413/12* (2013.01); *C07D 417/12* (2013.01)

(58) Field of Classification Search
None
See application file for complete search history.

(56) References Cited

U.S. PATENT DOCUMENTS

| 4,863,951 | A | 9/1989 | Peglion et al. |
| 5,872,119 | A | 2/1999 | Wermuth et al. |
| 6,090,807 | A | 7/2000 | Hellendahl et al. |
| 6,358,955 | B1 | 3/2002 | Thurkauf et al. |
| 6,465,485 | B1 | 10/2002 | Branch et al. |
| 6,521,638 | B1 | 2/2003 | Johnson et al. |
| 6,602,867 | B1 | 8/2003 | Starck et al. |
| 6,673,800 | B2 | 1/2004 | Koh et al. |
| 8,829,001 | B2 * | 9/2014 | Li et al. .................... 514/252.19 |
| 2002/0156085 | A1 | 10/2002 | Anand et al. |
| 2005/0197343 | A1 | 9/2005 | Gmeiner et al. |
| 2007/0054918 | A1 | 3/2007 | Braje et al. |
| 2008/0113988 | A1 | 5/2008 | Andres-Gil et al. |
| 2008/0194539 | A1 | 8/2008 | Gmeiner et al. |
| 2008/0214542 | A1 | 9/2008 | Capet et al. |
| 2011/0251212 | A1 | 10/2011 | Masui et al. |

FOREIGN PATENT DOCUMENTS

| CA | 2574827 A1 | 2/2006 |
| EP | 1749529 A1 | 2/2007 |
| WO | 9504713 A1 | 2/1995 |
| WO | 9510513 A1 | 4/1995 |
| WO | 9743262 A1 | 11/1997 |
| WO | 9806699 A1 | 2/1998 |
| WO | 03028728 A1 | 4/2003 |
| WO | 03051370 A1 | 6/2003 |
| WO | 2007022936 A1 | 3/2007 |

(Continued)

OTHER PUBLICATIONS

Achat-Mendes et al. Journal of Pharmacology and Experimental Therapeutics vol. 334, pp. 556-565 (2010).*

(Continued)

*Primary Examiner* — Emily Bernhardt
(74) *Attorney, Agent, or Firm* — Banner & Witcoff, Ltd.

(57) ABSTRACT

The present invention relates to a novel piperazine derivative represented by Formula I having an activity for regulating dopamine D3 receptor, stereoisomers thereof, pharmaceutically acceptable salts or solvates, and a pharmaceutical composition comprising the compound, a process for preparing the same, and use thereof in the prevention or treatment of a disease associated with central nervous system dysfunction, such as Parkinson's disease, schizophrenia, drug addiction and relapse, as well as kidney protection and immunoregulation, or as a tool for researching D3R function or diseases associated with D3R dysfunction.

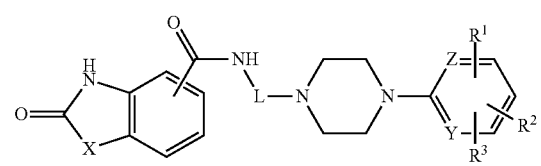

4 Claims, 30 Drawing Sheets

(56) References Cited

FOREIGN PATENT DOCUMENTS

| WO | 2008047883 A1 | 4/2008 |
|---|---|---|
| WO | 2009025265 A1 | 2/2009 |

OTHER PUBLICATIONS

Hu et al., "The dopamine D3 receptor antagonist YQA14 that inhibits the expression and drug-primed reactivation of morphine-induced conditioned place preference in rats,"European Journal of Pharmacology, 720, 2013, pp. 212-217.

Blagg et al., Design and synthesis of a functionally selective D3 agonist and its in vivo delivery via the intranasal route, Bioorg Med Chem Lett, 2007, 17: 6691-6696.

Boeckler et al., "Attenuation of 1-methyl-4-phenyl-1,2,3,6-tetrahydropyridine (MPTP) neurotoxicity by the novel selective dopamine D3-receptor partial agonist FAUC 329 predominantly in the nucleus accumbens of mice", Beichem Pharmacol, 2003, 66: 1025-1032.

Dubuffet et al., "Novel Benzopyrano[3,4-C]Pyrrole Derivatives as Potent and Selective Dopamine D3 Receptor Antagonists", Bioorg & Med Chem Lett, 1999, 9: 2059-2064.

Grundt et al., "Dopmine D3 Receptor Partial Agonists and Antagonists as Potential Drug Abuse Therapeutic Agents", J Med Chem, 2005, 45(11): 3663-3679.

Grundt et al., "Heterocyclic Analogues of N-(4-(4-(2,3-Dichlorophenyl)piperazin-1-yl)butyl)arylcarboxamides with Functionalized Linking Chains as Novel Dopamine D3 Receptor Ligands: Potential Substance Abuse Therapeutic Agents," J. Med. Chem, 2007, 50, 4135-4146.

Heidbreder, "Recent Advances in the Pharmacotherapeutic Management of Drug Dependence and Addiction", Curr Psychiatry Rev, 2005, (1): 45-67.

Heidbreder et al., "The role of central dopamine D3 receptors in drug addiction: a review of pharmacological evidence", Brain Res Rev, 2005, 49: 77-105.

Japanese Office Action for JP No. 2011-530350 mailed Nov. 5, 2013, with translation.

Joyce, J.N. et al., "Dopamine D3 receptor antagonists as therapeutic agents", Drug Disc Today, 2005,10(13): 917-925.

Leiberman, "Depression in Parkinson's disease—a review", Acta Neuro Scand, 2006, 113: 1-8.

Leopoldo et al., "Design, Synthesis, and Binding Affinities of Potential Positron Emission Tomography (PET) Ligands for Visualization of Brain Dopamine D3 Receptors," J. Med. Chem, 2006, 49, 358-365.

Luippold et al., "Effect of dopamine D3 receptor blockade on reneal function and glomerular size in diabetic rats," Arch. Pharmacology, vol. 371, pp. 420-427, 2005.

Moore, N.A. et al., "Behavioral Pharmacology of Olanzapine: A Novel Antipsychotic Drug", J Clin Psychiatry, 58 (suppl 10): 37-44 (1997).

Song et al., "YQA14: a novel dopamine D3 receptor antagonist that inhibits cocaine self-administration in rats and mice, but not in D3 receptor-knockout mice," Addiction Biology 17, 259-73, 2011.

Song et al., "Blockade of D3 Receptors by YQA14 Inhibits Cocaine's Rewarding Effects and Relapse to Drug-Seeking Behavior in Rats," Neuropharmacology, Feb. 2014;77:398-405; Epub Oct. 28, 2013.

Song et al., "Dopamine D3 receptor deletion or blockade attenuates cocaine-induced conditioned place preference in mice," Neuropharmacology 72, 82-87, 2013.

Suzuki, T. et al., "Studies on a New Nonsteroidal Antiinflammatory Agent II. A New Synthetic Mthod of 2-Substituted-5-benzothiazole-acetic Acids and Their Derivatives", 1974, 94(8): 891-897.

Vippagunta et al., "Crystalline Solids," Advanced Drug Delivery Reviews, vol. 48, pp. 3-26, 2001.

Xi et al., "Levo-tetrahydroplamatine inhibits cocaine's rewarding effects: Experiments with self-administration and brain-stimulation reward in rats," Neuropharmacology, 2007, 53: 771-782.

Food and Drug Administration, Center for Drug Evaluation and Research (CDER), "Assessment of Abuse Potential of Drugs," Draft Guidance for Industry, Jan. 2010, 25 pages.

Haney et al., "Controversies in Translational Research: Drug Self-administration," NIH Public Access Author Manuscript, available in PMC on Aug. 25, 2009, pp. 1-24; published in final form in Psychopharmacology 199, 403-19, 2008.

Marusich et al., "Prediction and Prevention of Prescription Drug Abuse: Role of Preclinical Assessment of Substance Abuse Liability," NIH Public Access Author Manuscript, available in PMC on Sep. 3, 2013, pp. 1-16; published in final form in Methods Rep RTI Press. 1-14, Jul. 2013.

Mugnaini et al., "Occupancy of Brain Dopamine D3 Receptors and Drug Craving: A Translational Approach," Neuropsychopharmacology 38, 302-12, 2013.

* cited by examiner

FIG. 19A
FIG. 19B
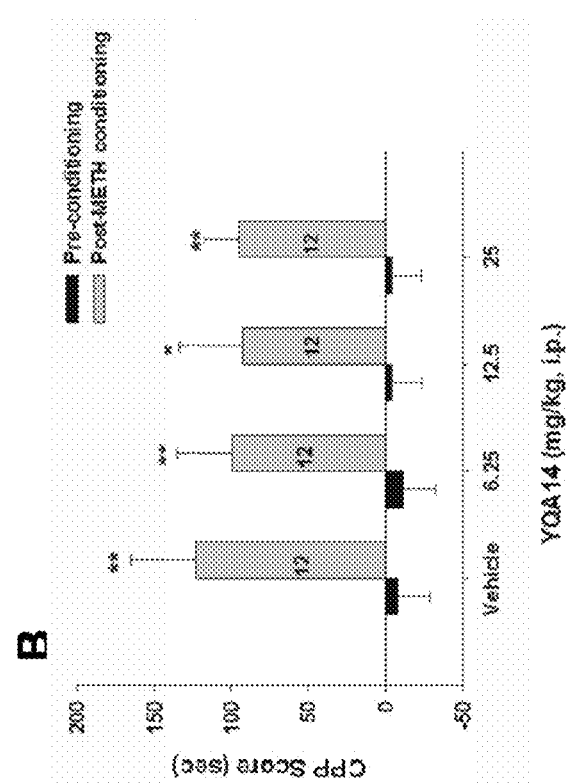
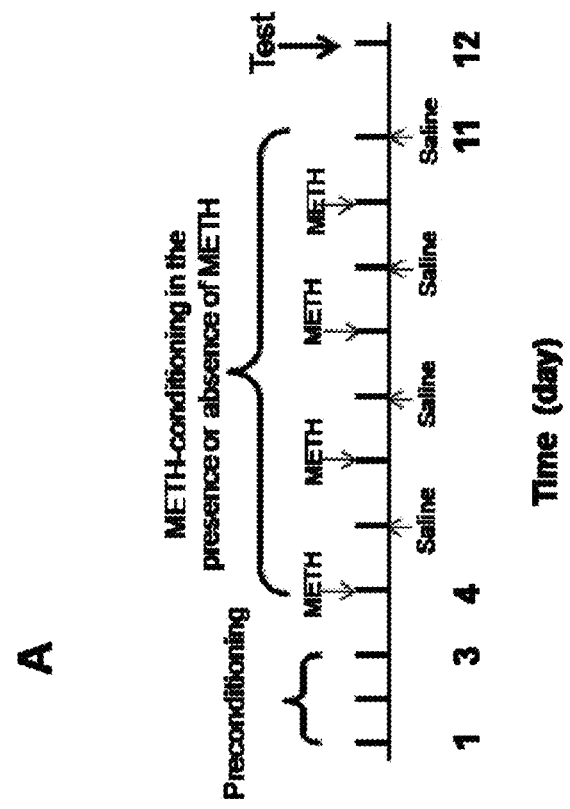

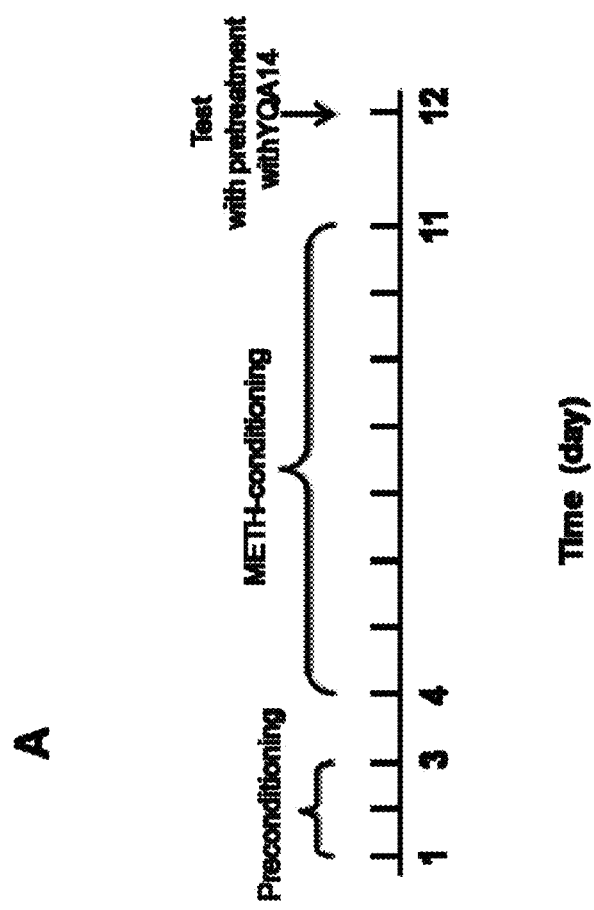
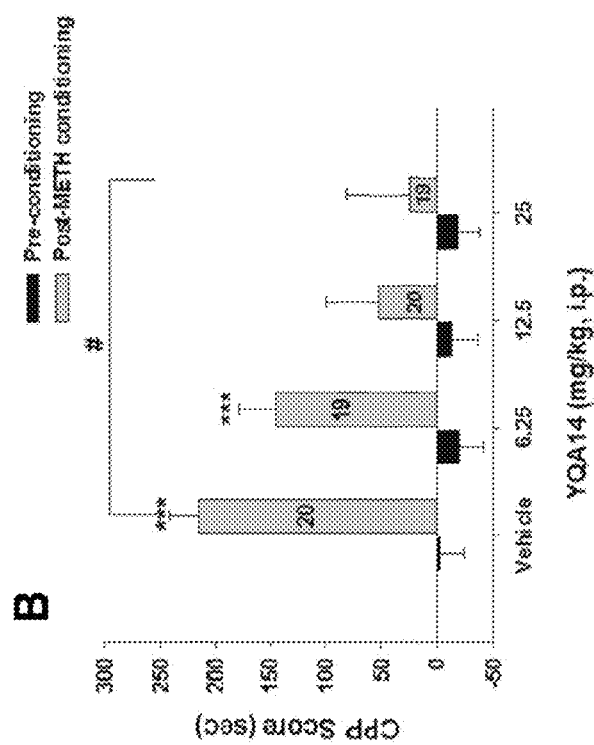
FIG. 20A
FIG. 20B

FIG. 21A
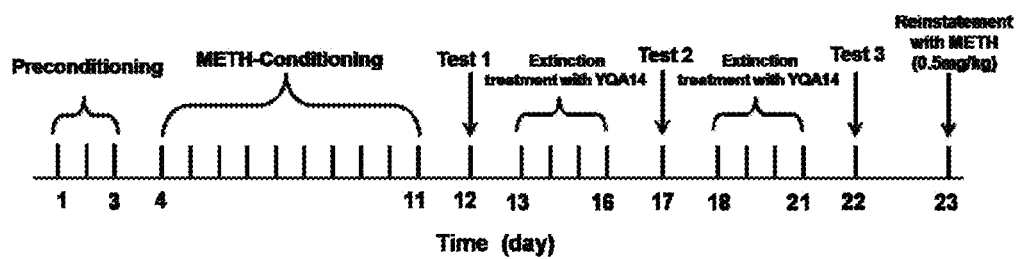
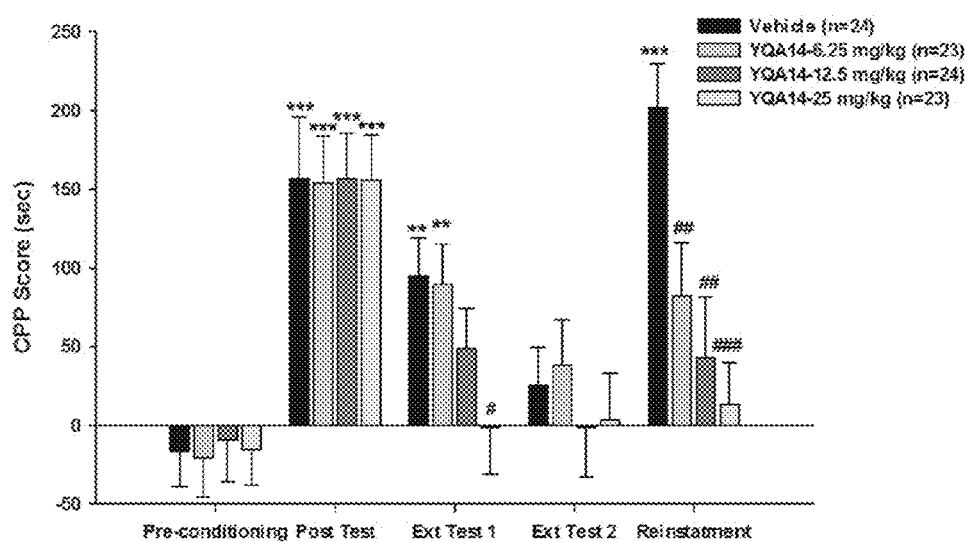
FIG. 21B

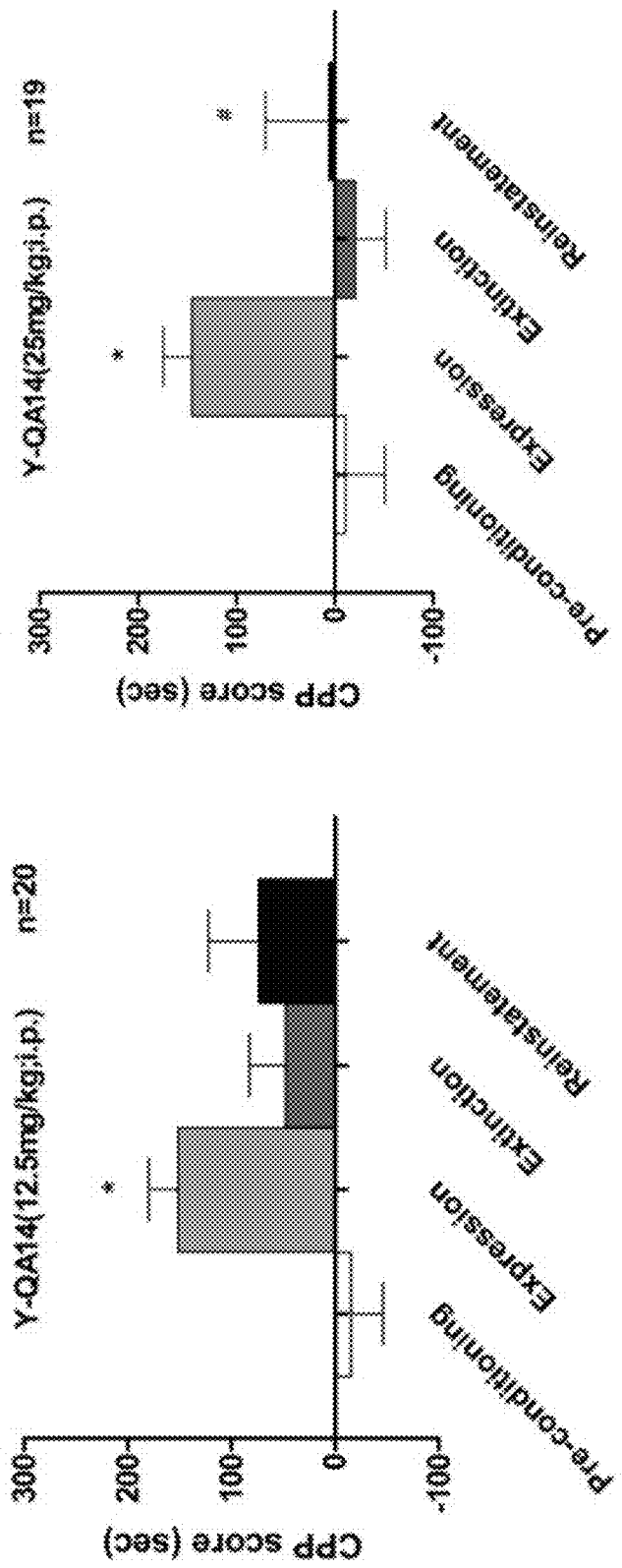

DOPAMINE D3 RECEPTOR LIGANDS AND PREPARATION AND MEDICAL USES OF THE SAME

TECHNICAL FIELD

The present invention relates to a novel piperazine derivative of formula I having dopamine D3 receptor (D3R) regulating activity, or stereoisomers, pharmaceutically acceptable salts and solvates of the same, to a process for preparing the same, to use thereof in the prevention or treatment of diseases associated with central nervous system disorders, such as Parkinson's disease, schizophrenia, drug addiction and relapse, as well as for kidney protection and immunoregulation, or use as a tool for researching D3R function and diseases associated with D3R dysfunction, and to a pharmaceutical composition comprising such compounds.

BACKGROUND ART

Dopamine (DA) is an important neuromediator in central nervous system. The disbalance of DA nerves in brain may result in schizophrenia, Parkinson's disease, drug addiction and relapse, attention deficit or sexual dysfunction.

In 1990, Sokoloff et al found dopamine D3 receptor (D3R), and found it has 50% amino acid sequence homology in comparison with D2R, and further identified the specific typing of dopamine receptor. D3R is selectively distributed in marginal brain area, such as nucleus accumbens, Callejia island, olfactory tubercle. Some current research reports show that D3R is closely associated with many neurosises, such as schizophrenia, Parkinson's disease, drug dependence (or drug addiction), any forms of stress, anxiety, and somnipathy. In addition, D3R is associated with physiologic functions such as kidney function and immunoregulation.

In investigating the physiological functions of D3R and its correlation with central diseases, kidney dysfunction and immunological disorders, the research of D3R ligands is also a hotspot of drug studying. D3R ligands can be divided into D3R preferential ligands and D3R selective ligands according to their selectivity, or divided into D3R agonists, D3R partial agonists and D3R antagonists.

Currently, D3R ligands having relatively high affinity and selectivity have been disclosed in many technical reports. According to their chemical structure, the present D3R ligands mainly include 2-aminoindanes (WO95/04713), 2-aminotetrahydronaphthalenes (EP-A286516), tetrahydroisoquinolines (WO 97/43262, WO98/06699, U.S. Pat. No. 6,465,485 B1), benzoazepines (CN 01821985.3), dihydroindolines (U.S. Pat. No. 6,521,638B1), aryl piperazine derivatives (FR2878524), heterocyclic amides (EP 1749529), sulfonamides (US2007054918), benzothiophenes (WO95/10513), isoxazole derivatives (U.S. Pat. No. 6,673,800B2), substituted imidazoles (U.S. Pat. No. 6,358,955B1), triazoles (U.S. Pat. No. 6,602,867B1, WO2007022936), pyrimidinylpiperazine derivatives (CA2574827), etc. In general, there are groups of arylformamides, bioisosteres with arylformamido group, and 1,2,3,4-tetrahydronaphthalene-2-amine and analogs thereof, in which the group of arylformamides is the biggest group, in which the aryl can be of various types, the amino moiety can be mainly piperazine or tetrahydroisoquinoline, and amino can be linked to the arylformamido via four methylene groups or an equivalent linking chain (YANG Rifang, YUN Liuhong, "Advance in research of dopamine D3 receptor selective ligands, *Progesses in Medicinal Chemistry* 5, Edited by PENG Sixun, Chemical Industry Press, Beijing, 2007, pp90-108).

Some D3R selective ligands show potential values for developing new drugs with D3R as the target in corresponding animal models and clinic trials. For example, Pramipexole (A Lieberman. *Acta Neurol Scand,* 2006, 113: 1), FAUC329 (F Boeckler, et al. *Biochem Phamacol,* 2003, 66(6): 1025), and BP897 (U.S. Pat. No. 5,872,119) disclose excellent neuroprotective effects in macaque model of Parkinson's disease; D3R preferential ligands 533138, A437203 (T Dubuffer, et al. *Bioorg Med Chem Lett,* 1999, 9(14): 2059; J F Joyce, M J Millan. *Drug Disc Today,* 2005, 10: 917) have entered phase II clinical test for treatment of schizophrenic; BP897 (C A Heidbreder. *Curr Psychiatry Rev,* 2005, 1: 45), SB277011A (C A Heidbreder, et al. *Brain Res Rev,* 2005, 49(1): 77) and NGB2904 (P Grundt, et al. *J Med Chem,* 2005, 48(13): 917) have beening drawing many attentions in studying of drug addiction mechanism and development of drugs for treatment of drug addiction and relapse, in which BP897 as smoking deterent is currently in phase II clinical test. Other reports mention that D3R agonist can be used for prevention of male sexual dysfunction (WO2003/051370, J Bragg, et al. *Bioorg Med Chem Lett,* 2007, 17: 6691).

Recent investigations indicate that D3R preferential ligands are more effective in prevention of drug abuse and relapse without exhibiting toxic and side effects of D2R ligands (Z-X Xi, et al. *Neuropharmacology,* 2007, 53: 771).

At present, there is still a need to search for novel compounds as dopamine D3 receptor ligands for clinical uses.

CONTENTS OF THE INVENTION

The inventors of the present invention found by research a compound of formula I having a function for regulating D3R, this compound can be used for prevention or treatment of schizophrenia, Parkinson's disease, drug dependence (or drug addiction) and relapse, various mental strain, anxiety, somnipathy and male sexual dysfunction, as well as kidney protection and immunoregulation. Some researches indicate that the compound of formula I has function of regulating D3R. Further synthesis and researches indicate that pharmaceutically acceptable salts of the derivatives of the present invention formed with a suitable inorganic acid or organic acid or with an inorganic base or organic base also have functions of regulating D3R. The present invention is completed based on the above findings.

SUMMARY OF THE INVENTION

The first aspect of the present invention relates to a compound of formula I having a function for regulating D3R,

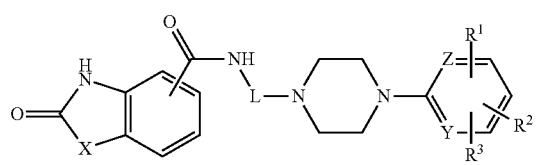

I or its tautomers, its racemates or optical isomers, its pharmaceutically acceptable salts or solvates, wherein:

L is $CH_2CH_2CH_2CH_2$, cis- or trans-$CH_2CH\!\!=\!\!CHCH_2$, or trans-cyclohexanyl-4-ethyl;

$R^1$, $R^2$, and $R^3$ each are independently H, halogen (F, Cl, Br, or I), alkyl, substituted alkyl, alkenyl, substituted alkenyl, phenyl, substituted phenyl, heteroaryl, substituted heteroaryl, $C_1$-$C_6$ alkyloxy, $C_5$-$C_{10}$ aryloxy, substituted aryloxy, $C_1$-$C_6$ alkylamino, $C_5$-$C_{10}$ arylamino, substituted arylamino, di-($C_1$-$C_6$ alkyl)amino, di-($C_5$-$C_{10}$aryl)amino, di-(substituted aryl)amino, $C_{1-10}$ hydrocarbonylacyloxy, $C_{6-10}$ arylacyloxy, $C_{1-10}$ hydrocarbonylamido, $C_{6-10}$ arylamido, carboxyl, $C_{1-10}$ hydrocarbonyloxyformyl, $C_{6-10}$ aryloxyformyl, carbamoyl, $C_{1-10}$ hydrocarbonylcarbamoyl, or $C_{6-10}$ arylcarbamoyl; wherein the heteroaryl ring is a monocyclic or condensed aromatic ring having 1-3 heteroatoms selected from N, O or S, the substituents of each group having substituents are independently selected from halogen, hydroxyl, cyano, nitro, $C_{1-6}$ alkyl, $C_{1-6}$ alkyloxy, $C_{1-6}$ alkylthio, mono-, di- or tri-halogen substituted $C_{1-6}$ alkyl, amino, $C_{1-6}$ alkylamino, $C_{1-10}$ hydrocarbonylacyloxy, $C_{1-10}$ hydrocarbonylamido, $C_{6-10}$ arylacyloxy or $C_{6-10}$ arylamido; or $R^1$ and $R^3$ are attached together to form a 5-, 6- or 7-membered ring;

X is O or S; Y and Z, the same or different, each are CH or N; and the formyl may be at 4-, 5-, 6-, or 7-position of oxazolin-2-one or thiazolin-2-one.

Specifically, the first aspect of the present invention provides a compound of formula I,

I or its tautomers, its racemates or optical isomers, its pharmaceutically acceptable salts or solvates, wherein:

L is —$CH_2CH_2CH_2CH_2$—, cis- or trans-$CH_2CH$=$CHCH_2$—, or trans-cyclohexyl-4-ethyl;

$R^1$, $R^2$, and $R^3$ each are independently H, halogen (F, Cl, Br, or I), $C_1$-$C_6$ alkyl, substituted $C_1$-$C_6$ alkyl, $C_1$-$C_6$ alkenyl, substituted $C_1$-$C_6$ alkenyl, phenyl, substituted phenyl, heteroaryl, substituted heteroaryl, $C_1$-$C_6$ alkyloxy, $C_5$-$C_{10}$ aryloxy, substituted $C_5$-$C_{10}$ aryloxy, $C_1$-$C_6$ alkylamino, $C_5$-$C_{10}$ arylamino, substituted arylamino, di-($C_1$-$C_6$ alkyl)amino, di-($C_5$-$C_{10}$aryl)amino, di-(substituted $C_5$-$C_{10}$aryl)amino, $C_{1-10}$hydrocarbonylacyloxy, $C_{6-10}$arylacyloxy, $C_{1-10}$hydrocarbonylamido, $C_{6-10}$arylamido, carboxyl, $C_{1-10}$ hydrocarbonyloxyformyl, $C_{6-10}$ aryloxyformyl, carbamoyl, $C_{1-10}$ hydrocarbonylcarbamoyl, or $C_{6-10}$ arylcarbamoyl; wherein the heteroaryl ring is a monocyclic or condensed aromatic ring having 1-3 heteroatoms selected from N, O or S, the substituents of each group having substituents are independently selected from halogen, hydroxyl, cyano, nitro, $C_{1-6}$ alkyl, $C_{1-6}$ alkyloxy, $C_{1-6}$ alkylthio, mono-, di- or tri-halogen substituted $C_{1-6}$ alkyl, amino, $C_{1-6}$ alkylamino, $C_{1-10}$hydrocarbonylacyloxy, $C_{1-10}$hydrocarbonylamido, $C_{6-10}$arylacyloxy or $C_{6-10}$arylamido; or $R^1$ and $R^3$ are attached together to form a 5-, 6- or 7-membered ring;

X is O or S;

Y and Z, the same or different, are each C or N;

The formyl may be at 4-, 5-, 6-, or 7-position of oxazolin-2-one or thiazolin-2-one.

The compound of formula I according to any one item of the first aspect of the present invention, or its tautomers, its racemates or optical isomers, its pharmaceutically acceptable salts or solvates, wherein L is —$CH_2CH_2CH_2CH_2$—, cis- or trans-$CH_2CH$=$CHCH_2$—, or trans-cyclohexyl-4-ethyl. In one embodiment of the first aspect of the present invention, L is —$CH_2CH_2CH_2CH_2$—, or cis- or trans-$CH_2CH$=$CHCH_2$—. In one embodiment of the first aspect of the present invention, L is —$CH_2CH_2CH_2CH_2$—. In one embodiment of the first aspect of the present invention, L is cis- or trans-$CH_2CH$=$CHCH_2$—.

The compound of formula I according to any one item of the first aspect of the present invention, or its tautomers, its racemates or optical isomers, its pharmaceutically acceptable salts or solvates, wherein $R^1$, $R^2$, and $R^3$ each are independently H, halogen (F, Cl, Br, or I), $C_1$-$C_6$ alkyl, substituted $C_1$-$C_6$ alkyl, $C_1$-$C_6$ alkenyl, substituted $C_1$-$C_6$ alkenyl, phenyl, substituted phenyl, heteroaryl, substituted heteroaryl, $C_1$-$C_6$ alkyloxy, $C_5$-$C_{10}$ aryloxy, substituted $C_5$-$C_{10}$ aryloxy, $C_1$-$C_6$ alkylamino, $C_5$-$C_{10}$ arylamino, substituted arylamino, di-($C_1$-$C_6$ alkyl)amino, di-($C_5$-$C_{10}$aryl)amino, di-(substituted $C_5$-$C_{10}$aryl)amino, $C_{1-10}$hydrocarbonylacyloxy, $C_{6-10}$arylacyloxy, $C_{1-10}$hydrocarbonylamido, $C_{6-10}$arylamido, carboxyl, $C_{1-10}$ hydrocarbonyloxyformyl, $C_{6-10}$ aryloxyformyl, carbamoyl, $C_{1-10}$ hydrocarbonylcarbamoyl, or $C_{6-10}$ arylcarbamoyl; wherein the heteroaryl ring is a monocyclic or condensed aromatic ring having 1-3 heteroatoms selected from N, O or S, the substituents of each group having substituents are independently selected from halogen, hydroxyl, cyano, nitro, $C_{1-6}$ alkyl, $C_{1-6}$ alkyloxy, $C_{1-6}$ alkylthio, mono-, di- or tri-halogen substituted $C_{1-6}$ alkyl, amino, $C_{1-6}$ alkylamino, $C_{1-10}$ hydrocarbonylacyloxy, $C_{1-10}$hydrocarbonylamido, $C_{6-10}$arylacyloxy or $C_{6-10}$ arylamido. In one embodiment of the first aspect of the present invention, $R^1$, $R^2$, $R^3$ each are independently H, halogen (F, Cl, Br, or I), $C_1$-$C_6$ alkyl, substituted $C_1$-$C_6$ alkyl, or $C_1$-$C_6$ alkyloxy; wherein the heteroaryl ring is a monocyclic or condensed aromatic ring having 1-3 heteroatoms selected from N, O or S, the substituents of each group having substituents are independently selected from halogen, hydroxyl, cyano, nitro, $C_{1-6}$ alkyl, $C_{1-6}$ alkyloxy, $C_{1-6}$ alkylthio, mono-, di- or tri-halogen substituted $C_{1-6}$ alkyl, amino, $C_{1-6}$ alkylamino, $C_{1-10}$ hydrocarbonylacyloxy, $C_{1-10}$hydrocarbonylamido, $C_{6-10}$arylacyloxy or $C_{6-10}$ arylamido. In one embodiment of the first aspect of the present invention, $R^1$, $R^2$, and $R^3$ each are independently H, F, Cl, Br, I, $C_1$-$C_6$ alkyl, or $C_1$-$C_6$ alkyloxy. In one embodiment of the first aspect of the present invention, $R^1$, $R^2$, and $R^3$ each are independently H, F, Cl, Br, I, $C_1$-$C_4$ alkyl, or $C_1$-$C_4$ alkyloxy. In one embodiment of the first aspect of the present invention, $R^1$, $R^2$, and $R^3$ each are independently H, F, Cl, methyl, ethyl, methyloxy, or ethyloxy.

The compound of formula I according to any one item of the first aspect of the present invention, or its tautomers, its racemates or optical isomers, its pharmaceutically acceptable salts or solvates, wherein X is O or S. In one embodiment of the first aspect of the present invention, X is O. In one embodiment of the first aspect of the present invention, X is S.

The compound of formula I according to any one item of the first aspect of the present invention, or its tautomers, its racemates or optical isomers, its pharmaceutically acceptable salts or solvates, wherein Y and Z each are independently C or N. In one embodiment of the first aspect of the present invention, Y is C. In one embodiment of the first aspect of the present invention, Z is C. In one embodiment of the first aspect of the present invention, both Y and Z are C.

The compound of formula I according to any one item of the first aspect of the present invention is selected from:
N-{4-[4-(5-chloro-2-methylphenyl)piperazinyl]butyl}-benzoxazolin-2-one-5-carboxamide;
N-{4-[4-(5-chloro-2-methylphenyl)piperazinyl]butyl}-benzoxazolin-2-one-6-carboxamide;

N-{4-[4-(2-methyloxyphenyl)piperazinyl]butyl}-benzoxazolin-2-one-5-carboxamide

N-{4-[4-(2-methyloxyphenyl)piperazinyl]butyl}-benzoxazolin-2-one-6-carboxamide

N-{4-[4-(5-chloro-2-methylphenyl)piperazinyl]-trans-2-buten-1-yl}-benzoxazolin-2-one-6-carboxamide;

N-{4-[4-(5-chloro-2-methylphenyl)piperazinyl]-cis-2-buten-1-yl}-benzoxazolin-2-one-5-carboxamide;

N-{4-[4-(2-methyloxyphenyl)piperazinyl]-trans-2-buten-1-yl}-benzoxazolin-2-one-5-carboxamide;

N-{4-[4-(2-methyloxyphenyl)piperazinyl]-trans-2-buten-1-yl}-benzoxazolin-2-one-6-carboxamide;

N-{4-[4-(2-methyloxyphenyl)piperazinyl]butyl}-benzothiazolin-2-one-6-carboxamide;

N-{4-[4-(5-chloro-2-methylphenyl)piperazinyl]butyl}-benzothiazolin-2-one-6-carboxamide;

N-{4-[4-(2-methyloxyphenyl)piperazinyl]-trans-2-buten-1-yl}-benzothiazolin-2-one-6-carboxamide;

N-{4-[4-(2-methyloxyphenyl)piperazinyl]butyl}-benzothiazolin-2-one-5-carboxamide; or N-{4-[4-(5-chloro-2-methylphenyl)piperazinyl]butyl}-benzothiazolin-2-one-5-carboxamide, or their tautomers, their racemates or optical isomers, their pharmaceutically acceptable salts or solvates.

The second aspect of the present invention relates to use of a compound of formula I according to any one item of the first aspect of the present invention, or its tautomers, its racemates or optical isomers, its pharmaceutically acceptable salts or solvates, in the manufacture of a medicament for the prevention or treatment of schizophrenia, Parkinson's disease, drug dependence (or drug addiction) and relapse, any forms of stress, anxieties, sleep disorders and male sexual dysfunction, as well as for kidney protection and immunoregulation, or as a tool for researching D3R function or diseases associated with D3R dysfunction.

The third aspect of the present invention provides use of a compound of formula I according to any one item of the first aspect of the present invention, or its tautomers, its racemates or optical isomers, its pharmaceutically acceptable salts or solvates, in the manufacture of a medicament having an activity for regulating dopamine D3 receptor.

The fourth aspect of the present invention provides a pharmaceutical composition, comprising a compound of formula I according to any one item of the first aspect of the present invention, or its tautomers, its racemates or optical isomers, its pharmaceutically acceptable salts or solvates, and a pharmaceutically acceptable carrier or excipient. According to this aspect, the present invention further provides use of the pharmaceutical composition in the manufacture of a medicament for the prevention or treatment of schizophrenia, Parkinson's disease, drug dependence (or drug addiction) and relapse, any forms of stress, anxieties, sleep disorders and male sexual dysfunction, as well as for kidney protection and immunoregulation, or as a tool for researching D3R function or diseases associated with D3R dysfunction.

The fifth aspect of the present invention provides a method for the prevention or treatment of a disease associated with D3R dysfunction, such as schizophrenia, Parkinson's disease, drug dependence (or drug addiction) and relapse, any forms of stress, anxieties, sleep disorders and male sexual dysfunction, as well as kidney dysfunction and immunological disorders, comprising administering to a subject in a need thereof a preventively and/or therapeutically effective amount of a compound of formula I according to any one item of the first aspect, or its tautomers, its racemates or stereoisomers, its pharmaceutically acceptable salts.

The sixth aspect of the present invention provides a process for preparing a compound of formula I according to any one item of the first aspect of the present invention, or its tautomers, its racemates or optical isomers, its pharmaceutically acceptable salts or solvates, comprising the following steps:

a) converting a carboxylic acid compound of formula II:

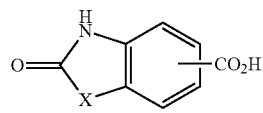

into an acyl chloride compound of formula IIa:

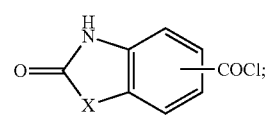

b) In the presence of a suitable base, reacting the acyl chloride compound of formula IIa obtained in the step a) with an amine compound of formula III:

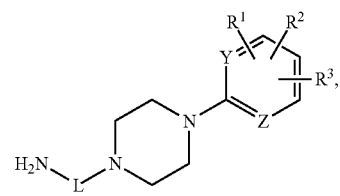

to obtain a compound of formula I:

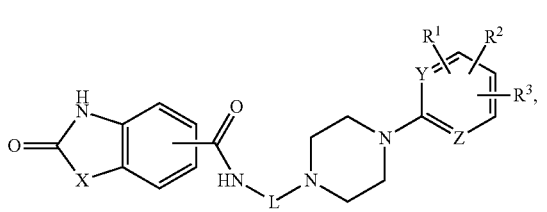

wherein the definitions of symbols are the same as given for the compound of formula I according to any one item of the first aspect of the present invention.

According to the method of the sixth aspect of the present invention, the carboxylic acid compound of formula II is obtained by reacting a carboxylic acid compound of formula IV:

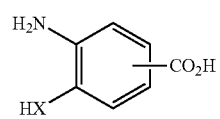

with a compound represented by $ClCO_2R$, wherein the definitions of symbols are the same as given for the compound of formula I according to any one item of the first aspect of the present invention.

According to the method of the sixth aspect of the present invention, the amine compound of formula III is obtained by reacting a compound of formula V:

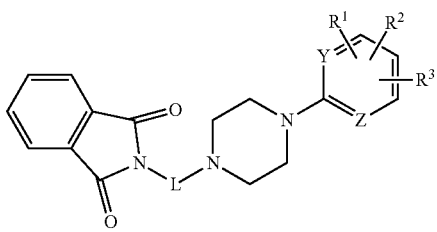

in the presence of a suitable agent (such as hydrazine hydrate), wherein the definitions of symbols are the same as given for the compound of formula I according to any one item of the first aspect of the present invention.

DETAILED DESCRIPTION OF THE INVENTION

All documents as cited in the present invention are incorporated in the description by reference, and if the meanings expressed in these documents are different from the present invention, the expressions in the present invention shall prevail.

In addition, the terms and phrases used in the present invention have common meanings as well known by those skilled in the art. Nevertheless, in the present invention, it is desired to further illustrate and explain these terms and phrases in a more detailed way, if the mentioned terms and phrases have meanings different from their common meanings, the meanings expressed in the present invention shall prevail.

In the present invention, the used terms "halogen", "halo", "Hal" or "halogeno" refers to fluorine, chlorine, bromine and iodine.

In the present invention, the used terms "alkyl", "alkenyl" and "alkynyl" have common meanings well known in the art, they are straight or branched hydrocarbonyl groups, such as but not limited to methyl, ethyl, propyl, isopropyl, n-butyl, sec-butyl, tert-butyl, allyl, propenyl, propinyl, and the "alkyl", "alkenyl" and "alkynyl" can also be collectively called "hydrocarbonyl" or "aliphatic hydrocarbonyl".

As used in the text, the term "substituted or unsubstituted $C_1$-$C_6$ alkyl" refers to substituted or unsubstituted alkyl having a designated number of carbon atoms, its examples include but are not limited to: methyl, ethyl, propyl, isopropyl, butyl, tert-butyl, pentyl, neopentyl, hexyl.

As for Y and Z in the compound of formula I, they can be independently C or N. Those skilled in the art would understand that Y and Z herein should meet the valence requirements of 6-membered ring. For example, when $R^1$, $R^2$, and $R^3$ are all hydrogen, if Y and Z are carbon, the 6-membered ring forms a beneze ring, so that Y or Z is —CH— atomic group; if Y is nitrogen, Z is carbon, the 6-membered ring forms a pyridine ring, so that Y is —N— atomic group, Z is —CH— atomic group. For another example, when Y is nitrogen and Z is carbon, if $R^1$ is halogen, and $R^2$ and $R^3$ are hydrogen, the halogen can be linked to Z to form a —CCl— atomic group.

According to the first aspect of the present invention, in the compound of formula I, $R^1$, $R^2$, and $R^3$ each are preferably H, F, Cl, Br, methyl, ethyl, methyloxy, ethyloxy, dimethylamino, diethylamino, carbamoyl, or phenyloxy;

L is preferably —$CH_2CH_2CH_2CH_2$—, or trans-$CH_2CH=CHCH_2$—;

X is preferably O or S; Y and Z each are preferably CH or N.

According to another aspect of the present invention, in the compound of formula I, $R^1$, $R^2$, and $R^3$ each are preferably 5-chloro-2-methyl, 2,3-dichloro, or 2-methyloxy;

L is preferably —$CH_2CH_2CH_2CH_2$—, or trans-$CH_2CH=CHCH_2$—;

X is preferably O; and Y and Z each are preferably N.

The compounds of formula I according to the present invention are preferably the compounds of the following examples.

In the preferable embodiments of the present invention, the compound is N-{4-[4-(5-chloro-2-methylphenyl)piperazinyl]butyl}-benzoxazolin-2-one-5-carboxamide and N-{4-[4-(5-chloro-2-methyl-phenyl)piperazinyl]butyl}-benzoxazolin-2-one-6-carboxamide.

According to the teaching of the present invention, the compound of formula I of the invention can be synthesized by known methods and technologies in the art.

In one embodiment of the process for preparing a compound of formula I, the compound is prepared by converting a corresponding carboxylic acid II into an acyl chloride, then reacting with a corresponding amine III in the presence of an deacidificating agent; or by a direct dehydration of a mixture of a corresponding carboxylic acid II and a corresponding amine III with a condensing agent such as carbodiimide (e.g., N,N'-dicyclohexylcarbodiimide) in the presence of 1-hydroxy-benzotriazole, in which the carboxylic acid II is obtained by a thermal cyclization reaction between a carboxylic acid IV with adjacently substituted amino and hydroxyl or mercapto and a chloroformic ester in the presence of a deacidifying agent; and the amine III is prepared by reacting a corresponding phthalimide V and hydrazine hydrate, wherein

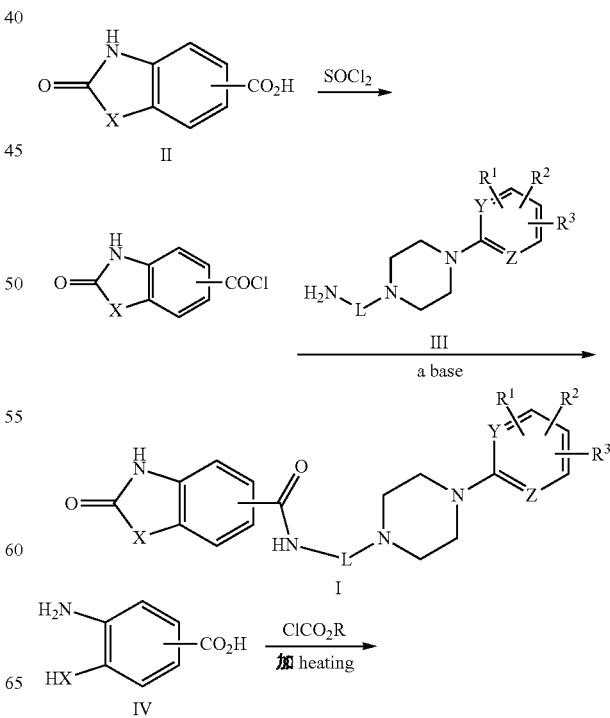

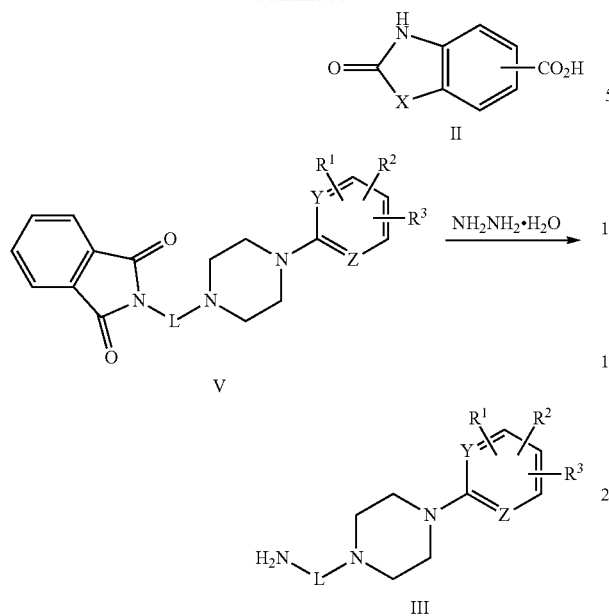

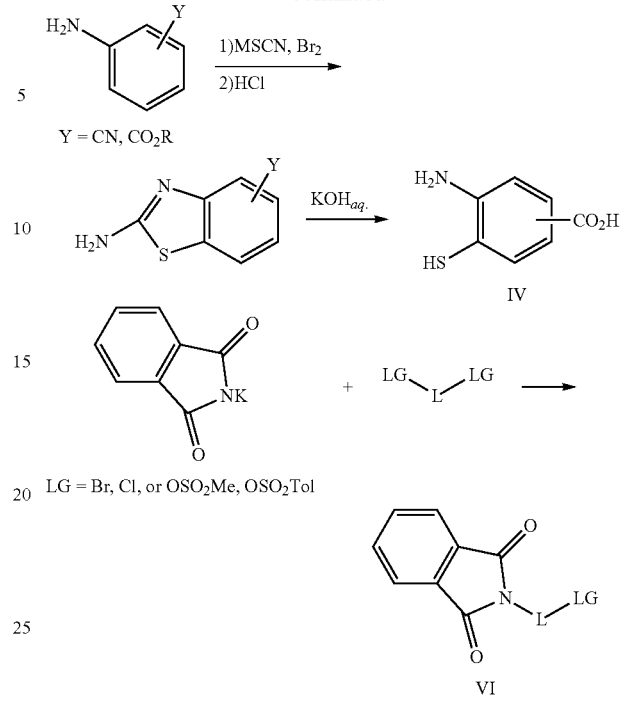

the carboxylic acid IV is prepared by nitrating a corresponding hydroxybenzoic acid, separating to obtain a benzoic acid adjacently substituted with nitro and hydroxy, then reducing to obtain a benzoic acid adjacently substituted with hydroxy and amino (IV); or by nitrating a corresponding chlorobenzoic acid, separating to obtain a benzoic acid adjacently substituted with chloro and nitro, then reducing and substituting with sodium sulfide to form a benzoic acid adjacently substituted with amino and mercapto (IV) (Tadayuki Suzuki et al, J. Pharmacy, 1974, 94:891-897); or by converting an aminobenzonitrile or aminobenzoic acid into a thiocyanobenzoic acid, cylizating to form 2-aminobenzothiazole, then hydrolyzing in the presence of a base to form a benzoic acid adjacently substituted with amino and mercapto (IV); while the phthalimide V is prepared by reacting a corresponding halide or active ester VI with a corresponding arylpiperazine, in which the halide or active ester VI can be synthesized by reacting pththalimide potassium salt with a corresponding dichloride or active ester.

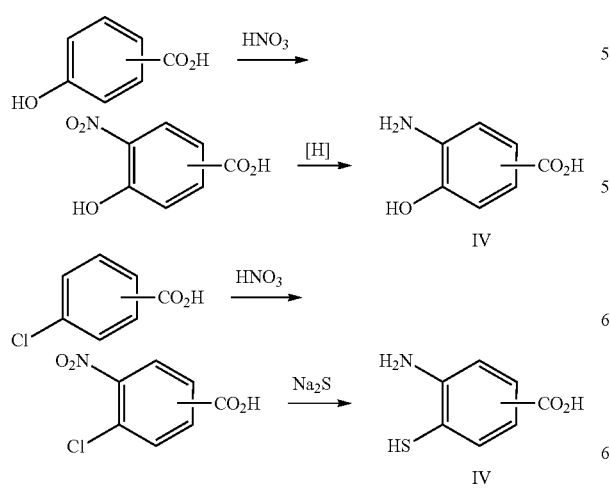

In the method for synthesizing a compound of formula I of the present invention, all used raw materials can be prepared according to the prior art, or prepared according to the methods known in the documents in the prior art, or commercially available. The intermediates, raw materials, reagents and reaction conditions used in the above reaction scheme all can be modified by those skilled in the art. In addition, those skilled in the art art can also synthesized other compounds of formula I not enumerated in the present invention according to the method of the second aspect of the present invention.

According to the present invention, the term "diseases associated with D3R function disorder" refers to diseases directly or indirectly caused by dopamine D3 receptor function disorder, such as schizophrenia, Parkinson's disease, drug abuse (or drug addiction) and relapse, any forms of stress, anxieties, sleep disorders and male sexual dysfunction, as well as disorders of kidney function or immunologic function induced thereby.

According to the present invention, the pharmaceutically acceptable salt of the compound of formula I can be an acid addition salt or a salt formed with a base. The examples of the acid addition salt can be inorganic salts such as but not limited to hydrochlorides, sulfates, phosphates, hydrobromides; or organic salts such as but not limited to acetates, oxalates, citrates, glyconates, succinates, tartrates, tosylates, mesylates, benzoates, lactates, maleates; the examples of the salt formed with the compound of formula I and a base can be alkaline metal salts such as but not limited to lithium salts, sodium salts and potassium salts; alkaline earth metal salts such as but not limited to calcium salts and magnesium salts; organic alkali salts such as but not limited to diethanolamine salts and choline salts; or chiral alkali salts such as but not limited to alkylphenylamine salts.

The solvates of the compound of the present invention can be hydrates or comprise other crystalline solvent such as alcohols such as ethanol.

According to the present invention, the compound of formula I can have cis/trans isomers. The present invention relates to these cis- and trans-isomers and mixtures thereof. If desired, a single stereoisomer can be prepared by conventional resolution of mixture, or by stereoselective synthesis. If there is a mobile hydrogen atom, the compound of formula I of the present invention can also be its tautomers.

According to the present invention, the compound of formula I or stereoisomers can be used in the manufacture of a medicament for prevention or treatment of diseases associated with D3R function disorder, such as schizophrenia, Parkinson's disease, drug abuse (or drug addiction) and relapse, any forms of stress, anxieties, sleep disorders and male sexual dysfunction, as well as disorders of kidney function or immunologic function induced thereby. The medicament can be applied to animals, preferably mammals, especially a human.

The present invention also relates to a pharmaceutical composition comprising an effective amount of at least one compound of the Formula I or pharmaceutically acceptable salts and/or stereoisomers thereof as an active ingredient and a conventional pharmaceutically acceptable excipient or adjuvant. Usually, the pharmaceutical composition of the present invention comprises 0.1-90 wt % of a compound of formula I and/or physiologically acceptable salt thereof. The pharmaceutical composition can be prepared by a known method in the art. If desired, an administration form or dosage form suitable for human use can be prepared by combining a compound of formula I and/or stereoisomer thereof with one or more solid or liquid pharmaceutically acceptable excipient and/or adjuvant.

The compound of formula I or a pharmaceutical composition comprising the same according to the present invention can be administered in unit dosage form via intestinal administration or parenteral administration, such as oral administration, intramuscular injection, subcutaneous injection, nasal administration, oral mucous administration, transdermal administration, intraperitoneal administration or rectal administration. The dosage form can be tablets, capsules, drop pills, aerosol, pills, powders, solutions, suspensions, emulsions, granules, liposomes, transdermal agents, buccal tablets, suppositories, lyophilized injection powder, can be normal preparations, sustained release preparations, controlled release preparations and various micropowder administration systems. In order to obtain tablets as unit dosage form, various carriers known in the art can be used. The examples of carriers are diluents and absorbents, such as starches, dextrins, calcium sulfates, lactose, mannitol, sucrose, sodium chloride, glucose, urea, calcium carbonate, kaolin, microcrystalline cellulose, aluminum silicate; wetting agents and binders, such as water, glycerol, polyethylene glycol, ethanol, propanol, starch paste, dextrin, syrup, honey, glucose solution, acacia mucilage, gelatin paste, carboxymethylcellulose sodium, shellac, methylcellulose, potassium phosphate, polyvinylpyrrolidone, disintegrating agents, such as dried starch, alginate, powdered agar, laminarin, sodium hydrogen carbonate and citric acid, calcium carbonate, polyoxyethylene sobitol fatty acid ester, sodium dodecyl sulfate, methylcellulose, ethylcellulose; disintegration inhibitors, such as sucrose, tristearin, cocoa butter, hydrogenated oil; absorption enhancers, such as quaternary ammonium salt, sodium dodecyl sulfate; lubricants, such as talc powder, silica, corn starch, stearates, boric acid, liquid paraffin, polyethylene glycol. The tablets can further form coated tablets, such as sugar coated tablets, film coated tablets, enteric-coated tablets, or bilayer tablets or multilayer tablets. In order to obtain pills as the unit dosage form, various carriers known in the art can be used. The examples of these carriers can be diluents and absorbents, such as glucose, lactose, starch, cocoa butter, hydrogenated vegetable oil, polyvinylpyrrolidone, Gelucire, kaolin, talc powder, etc.; binder such as gum arabic, tragacanth gum, gelatin, ethanol, honey, liquid sugar, rice paste or panada; disintegrating agents, such as powdered agar, dried starch, alginate, sodium dodecyl sulfate, methylcellulose, ethylcellulose. In order to obtain suppositories as the dosage form, various carriers known in the art can be used. The examples of these carriers can be polyethylene glycol, lecithine, cocoa butter, fatty alcohols, esters of fatty alcohols, gelatin, semi-synthesized glycerides. In order to obtain capsules as the dosage form, an effective amount of a compound of formula I or stereoisomer thereof is mixed with the above various carriers, and the resultant mixture is filled into hard gelatin capsules or soft capsules. An effective amount of a compound of formula I or stereoisomer thereof can also form microcapsules, be suspended in aqueous media to form suspensions, be filled in hard capsules, or form injections. In order to obtain injection preparations as unit dosage form, such as solutions, emulsions, lyophilized powder injection, and suspensions, conventional diluents in the art can be used, such as water, ethanol, polyethylene glycol, 1,3-propanediol, ethoxylated isooctadecanol, multi-oxidized isooctadecanol, polyoxyethylene sorbitol fatty acid esters. In addition, in order to obtain isotonic injection solutions, a suitable amount of sodium chloride, glucose or glycerol can be added to injection preparations. Further, other conventional solvents, buffers, pH regulators can also be added.

Moreover, if desired, other materials such as coloring agents, preservatives, flavoring agents, correctants, sweetening agents can also be added to these pharmaceutical preparations.

The dose of a compound of formula I or stereoisomer according to the present invention depends on many factors, such as nature and severity of diseases to be prevented or treated, gender, age, body weight and individual reactions of patients or animals, specific compound to be used, administration routes and frequency. The dose can be of single dose form, or multi-dose forms such as 2, 3 or 4 dose forms.

In the present invention, the term "composition" refers to a product comprising designated amounts of designated ingredients, and any products directly or indirectly obtained by combining various designated ingredients of designated amounts.

The actual dose level of various active ingredients in a pharmaceutical composition of the present invention can be varied so that the resultant amount of active compounds can lead to desired therapeutical reactions in specific patients, dosage forms and administration modes. The dose level must be determined according to the activity of specific compound, administration route, severity of disease to be treated, and conditions and past medical history of patients. However, a conventional method in the art is to increase gradually the dose of compound from a level lower than that for achieving desired therapeutical effects to a level enough to achieve the desired therapeutical effects.

In the aforementioned or other treatment and/or prophylaxis, a compound of the present invention in a therapeutically and/or prophylactically effective amount can be used in form of pure compound, or in form of pharmaceutically acceptable esters or predrugs thereof (if they exist). Alternatively, the compound can be administered via a pharmaceutical composition comprising the compound and one or more pharmaceutically acceptable excipients. The term a compound of the present invention in a "therapeutically and/or prophylactically effective amount" means that the compound is in an amount sufficient to achieve prophylactically and/or therapeutically reasonal ratio of effect/risk. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the used specific compound, the used specific composition, the age, body weight, general health status, gender and food of patient, the administration time and route and excretory rate of the used specific compound, the drug(s) administered in combination or simultaneously with the specific compound, and similar factors well known in the art of medicine. For example, it is a common method in the art to increase gradually the dose of compound from a level lower than that for achieving desired therapeutical effects to a level enough to achieve the desired therapeutical effects. In general, the dose of a compound of formula I for mammals especially a human can be 0.001-1000 mg/kg body weight per day, such as 0.01-100 mg/kg body weight per day, 0.01-10 mg/kg body weight per day.

The compound according to the present invention can be used for effective prophylaxis and/or treatment of various diseases and disorders as mentioned in the present invention.

BRIEF DESCRIPTION OF THE DRAWINGS

FIGS. 19A-B are graphs showing that chronic YQA14 pretreatment did not alter acquisition of METH-induced CPP.

FIGS. 20A-B are graphs showing that a single injection of YQA14 inhibits expression of METH-induced CPP.

FIGS. 21A-B are graphs showing that chronic YQA14 facilitates extinction of METH-induced CPP.

FIGS. 26A-D are graphs showing that YQA14 inhibited the reactivation of morphine-induced CPP in rats.

CONCRETE MODES FOR CARRYING OUT THE INVENTION

Examples

Figure 1:
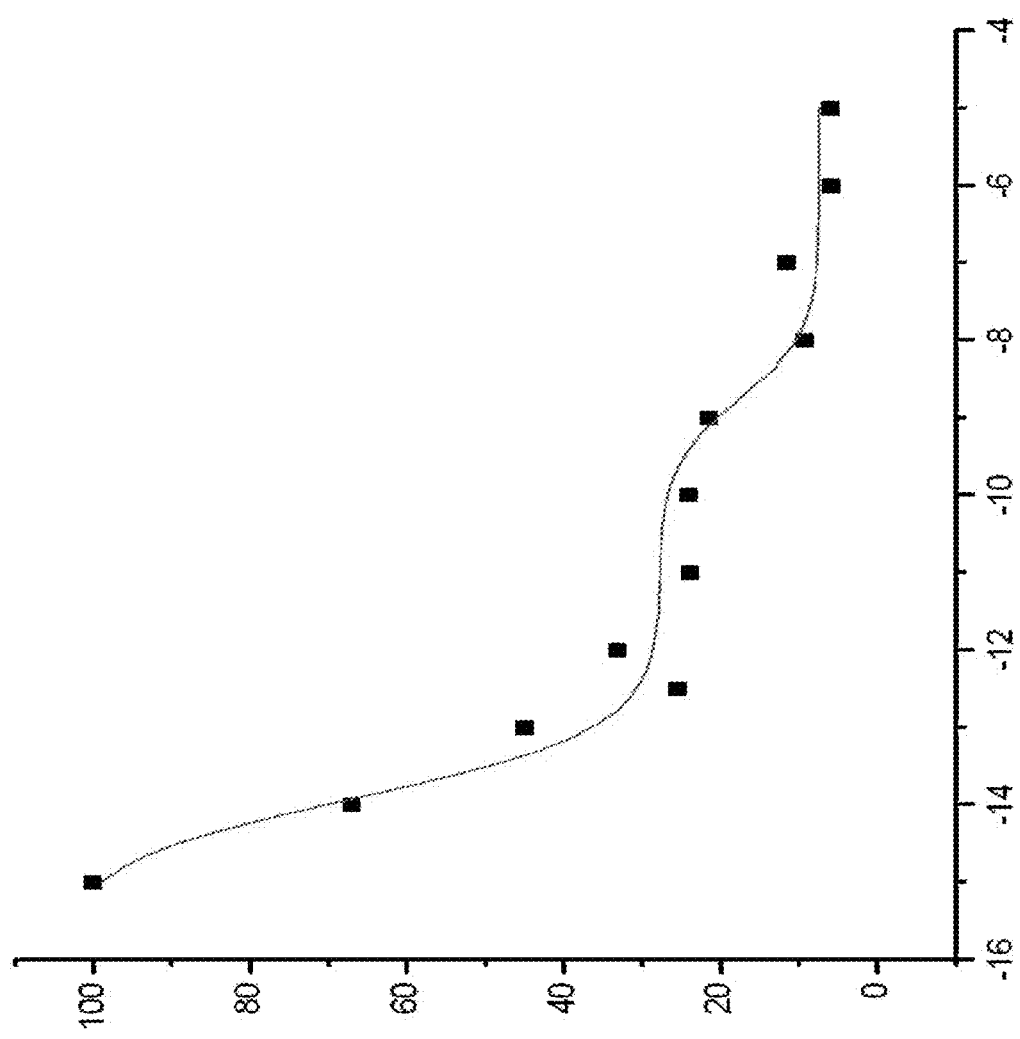
FIG. 1 is a competition-combination curve of Compound 1 of examples to D3R radioligand.

The present invention is further illustrated by the following examples, but these examples are not intended to restrict the present invention.

Example 1

Preparation of N-{4-[4-(5-chloro-2-methylphenyl)piperazinyl]butyl}-benzoxazolin-2-one-5-carboxamide (Compound 1, also called as Y-QA14)

(1) Benzoxazolin-2-one-5-carboxylic acid: 7.8 g (0.05 mol) of 3-amino-4-hydroxybenzoic acid was weighed, and added under stirring to 45 mL aqueous solution in which 8.5 g (0.08 mol) of anhydrous sodium carbonate was dissolved. The mixture was heated in a 45° C. oil bath, and added dropwise with 7.1 g of methyl chloroformate. After the addition, the reaction was carried out under stirring for 0.5 h, and then the temperature was elevated to 80° C. to keep the reaction overnight. In the next day, an acidification was carried out under cooling in an ice-water bath to pH 2-3, and a solid was filtered out, washed with a small amount of cold water, and dried to obtain a light brown powdery solid 7.5 g (83.3%), mp: 329-331° C. $^1$H-NMR (ppm, $d_6$-DMSO) δ: 7.385 (d, 1H, J=8.40 Hz, 7-H), 7.566 (d, 1H, J=1.68 Hz, 4-H), 7.74 (dd, 1H, J1=8.40 Hz, J2=1.68 Hz, 6-H), 11.868 (br-s, 1H, NH), 13.006 (br-s, 1H, CO2H).

(2) Benzoxazolin-2-one-5-formyl chloride: 0.5 g (2.80 mmol) benzoxazolin-2-one-5-carboxylic acid was weighed, dissolved in 30 ml 1,2-dichloroethane, and added dropwise with 0.67 g (5.6 mmol) thionyl chloride at room temperature. After addition, 10 drops of N,N-dimethylformamide was added as catalyst, and the reaction was heated to about 100° C. and carried out under reflux with stirring for 3 h, subjected to recovering solvent, transferred and dissolved in 15 ml anhydrous acetone for instant use.

(3) N-(4-bromobutyl)phthalimide: 93.6 g (0.43 mol) 1,4-dibromobutane was weighed, and added to 380 mL acetone. The mixture was added with 72.5 g (0.39 mol) phthalimide potassium salt and 2.1 g tetrabutylammonium iodide under stirring, subjected to refluxing for 18 h, cooled, filtrated to remove solid, and washed with acetone. All acetone solutions are combined, subjected to recovering the solvent under a reduced pressure, and added with petroleum ether for crystallization while the reaction mixture was hot. A solid was filtered out, washed with petroleum ether and dried to obtain a product 48.0 g (43.6%), mp 75~78° C. The mother liquor was concentrated to precipitate crystal, cooled in an ice-bath to obtain a solid 5.5 g (5.0%), mp 73~76° C.

(4) N-{4-[4-(5-chloro-2-methylphenyl)piperazinyl]butyl}phthalimide: N-(4-bromobutyl)phthalimide 7.0 g (0.025 mol) was weighed, and dissolved in 30 ml acetonitrile. The mixture was added with 4.2 g (0.02 mol) 5-chloro-2-methylphenyl-piperazine and dissolved under stirring, added dropwise with 5.05 g (0.05 mol) triethylamine after addition, heated to refluxing and reacted for 16 h. The reaction was subjected to recovering solvent under a reduced pressure after the end of reaction, washed with water, and extracted with ethyl acetate for 3 times. All organic layers were combined, dried with anhydrous sodium sulfate overnight, and subjected to recovering solvent to obtain a white viscous product, salified with hydrochloric acid ether to obtain a white solid product 7.55 g (78.0%), mp: 280-282° C. $^1$H-NMR (ppm, CDCl$_3$) δ: 1.60 (br-s, 2H), 1.76 (m, 2H), 2.23 (s, 3H), 2.45-2.60 (m, 4H), 2.88-2.96 (m, 6H), 3.75 (t, J=6.72 Hz, 2H), 6.95 (d, J=8.12 Hz, 2H), 7.08 (d, J=7.85 Hz, 1H), 7.72 (q, J=3.08 Hz, 2H), 7.84 (q, J=3.37 Hz, 2H).

(5) 4-[4-(5-chloro-2-methylphenyl)piperazinyl]-butylamine: N-{4-[4-(5-chloro-2-methylphenyl)piperazinyl]butyl}phthalimide hydrochloride 7.50 g (0.015 mol) was dissolved in 60 ml anhydrous ethanol. The mixture was added with 1.82 g (0.030 mol) hydrazine hydrate solution (content: 85%), heated to about 70° C., reacted under reflux with stirring for 4 h. After the completion of the reaction, ethanol was recovered under a reduced pressure, and the residual solid product was added with 15 ml 40% potassium hydroxide solution under stirring to dissolve. The solution was diluted with 30 mL water, and extracted with ethyl acetate for 3 times. All organic layers were combined, dried with anhydrous sodium sulfate overnight, and subjected to recovering solvent to obtain a light yellow oily product 3.83 g (88.2%). $^1$H-NMR (ppm, CDCl$_3$) δ: 1.56 (br-m, 4H), 2.24 (s, 3H), 2.42 (t, J=7.01 Hz, 2H), 2.60 (br-s, 4H), 2.76 (t, J=6.72 Hz, 2H), 2.92 (t, J=4.48 Hz, 4H), 6.94 (m, 2H), 7.06 (d, J=8.12 Hz, 1H).

(6) N-{4-[4-(5-chloro-2-methylphenyl)piperazinyl]butyl}-benzoxazolin-2-one-5-carboxamide: 0.73 g (2.60 mmol) 4-[4-(5-chloro-2-methylphenyl)piperazinyl]-butylamine was weighed, and added under stirring to 30 mL acetone solution in which 1.1 g (7.8 mmol) anhydrous potassium carbonate was dissolved. The mixture was added with the solution of benzoxazolin-2-one-5-formyl chloride (expressed as 2.80 mmol) as freshly prepared in step (2) in acetone, stirred at room temperature overnight, filtered under a reduced pressure in the next day, and washed sufficiently with acetone. The filtrates were collected, subjected to recovering acetone, washed with water, and extracted with dichloromethane for 3 times. All organic layers were combined, dried with anhydrous sodium sulfate, subjected to recovering dichloromethane, purified by column chromatography, and salified with hydrochloric acid ethyl ether to obtain a white solid product 0.89 g (78.1%), mp: 329-331° C. $^1$H-NMR δ (ppm, $d_6$-DMSO): 1.59 (br-s, 2H), 1.77 (br-s, 2H), 2.23 (s, 3H), 3.15 (br-m, 4H), 3.24 (br-m, 4H), 3.39 (q, J=7.00 Hz, 2H), 3.53 (d, J=12.05 Hz, 2H), 7.06 (m, 2), 7.23 (d, J=8.12 Hz, 1H), 7.37 (d, J=8.40 Hz, 1H), 7.58 (d, J=1.68 Hz, 1H), 7.67 (dd, J$_1$=8.40 Hz, J$_2$=1.68 Hz, 1H), 8.62 (br-s, 1H, NH), 10.57 (br-s, 1H, CO$_2$H). MS (ESI$^+$, m/z):443.2/445.3 (M+H$^+$, 3:1).

Example 2

Preparation of N-{4-[4-(5-chloro-2-methylphenyl)piperazinyl]-butyl}-benzoxazolin-2-one-6-carboxamide (Compound 2)

(1) Benzoxazolin-2-one-6-carboxylic acid: according to the method of Example 1, 4-amino-3-hydroxybenzoic acid and methyl chloroformate were heated for cyclization in the presence of sodium carbonate as deacidificating agent. The yield was 84.6%, mp: 312-316° C. $^1$H-NMR (ppm, $d_6$-DMSO) δ: 7.19 (d, 1H, J=8.12 Hz, 4-H), 7.74 (s, 1H, 7-H), 7.81 (dd, 1H, J$_1$=8.12 Hz, J$_2$=0.84 Hz, 5-H), 12.07 (br-s, 1H, NH), 12.85 (br-s, 1H, CO$_2$H).

(2) Preparation of N-{4-[4-(5-chloro-2-methylphenyl)-piperazinyl]butyl}-benzoxazolin-2-one-6-carboxamide: according to the method of Example 1, benzoxazolin-2-one-6-carboxylic acid was used to prepare benzoxazolin-2-one-6-formyl chloride, which then was reacted with 4-[4-(5-chloro-2-methylphenyl)piperazinyl]butylamine, and subjected to acylation in the presence of sodium carbonate as deacidficating agent to provide the product. The yield was 81.2%, mp: 205-209° C. $^1$H-NMR (ppm, CDCl$_3$) δ: 1.57-1.59 (s, br., 2H), 1.74 (s, br., 2H), 2.23 (s, 3H), 3.01 (m, 2H), 3.18 (br, 4H), 3.38 (br, 4H), 3.54 (d, J=10.92 Hz, 2H), 7.06 (m, 2H), 7.15 (d, J=8.2 Hz, 1H), 7.72-7.77 (m, 2H), 8.55 (s, 1H).

Example 3

Preparation of N-{4-[4-(2-methyloxyphenyl)piperazinyl]butyl}-benzoxazolin-2-one-5-carboxamide (Compound 3)

(1) 4-[4-(2-methyloxyphenyl)piperazinyl]butylamine: according to the method of claim 1, N-(4-bromobutyl)phthalimide and 2-methyloxyphenyl-piperazine was used in reaction to produce N-{4-[4-(2-methyloxyphenyl)piperazinyl]butyl}phthalimide, which was then reacted with hydrazine hydrate. The yield was: 84.3%. Hydrochloride salt had a mp: 173-175° C.

(2) N-{4-[4-(2-methyloxyphenyl)piperazinyl]butyl}-benzoxazolin-2-one-5-carboxamide: according to the method of Example 1, benzoxazolin-2-one-5-formyl chloride and 4-[4-(2-methyloxyphenyl)piperazinyl]butylamine were subjected to acylation in the presence of sodium carbonate as deacidficating agent to procide the product. Yield: 79.2%, mp: 208-212° C. $^1$HNMR (ppm, CDCl$_3$) δ: 1.53 (m, 4H), 2.36 (m, 2H), 2.94 (s, br., 4H), 3.27 (m., 2H), 3.35 (m, 4H), 3.76 (s, 3H), 6.85 (m, 2H), 6.94 (m, 2H), 7.34 (d, J=8.4 Hz, 1H), 7.55 (d, J=1.4 Hz, 1H), 7.55 (dd, J$_1$=1.4 Hz, J$_2$=8.4 Hz, 2H), 8.51 (t, J=5.6 Hz, 1H).

Example 4

Preparation of N-{4-[4-(2-methyloxyphenyl)piperazinyl]butyl}-benzoxazolin-2-one-6-carboxamide (Compound 4)

According to the method of Example 3, 4-[4-(2-methyloxyphenyl)piperazinyl]butylamine and benzoxazolin-2-one-6-formyl chloride were subjected to acylation in the presence of sodium carbonate as deacidficating agent to obtain the product. Yield: 71.2%. mp: 175-177° C. $^1$HNMR (ppm, DMSO-d$_6$) δ: 1.53 (m, 4H), 2.36 (m, 2H), 2.50 (s, br., 4H), 2.94 (s, br., 4H), 3.28 (m, 2H), 3.76 (s, 3H), 6.86 (m, 2H), 6.93 (m, 2H), 7.15 (d, J=8.1 Hz, 1H), 7.70-7.74 (m, 2H), 8.42 (t, J=5.6 Hz, 1H).

Example 5

Preparation of N-{4-[4-(5-chloro-2-methylphenyl)piperazinyl]-trans-2-butyl}-benzoxazolin-2-one-6-carboxamide (Compound 5)

(1) Trans-4-[4-(5-chloro-2-methylphenyl)piperazinyl]-2-buten-1-amine: according to the method of Example 1, phthalimide potassium salt was reacted with trans-1,4-dihydro-2-butene to obtain N-(trans-4-chloro-2-buten-1-yl)phthalimide, mp: 108-110° C.; which was then reacted with 5-chloro-2-methylphenylpiperazine to obtain N-{4-[4-(5-chloro-2-methylphenyl)piperazinyl]-trans-2-buten-1-yl}phthalimide, which was then reacted with hydrazine hydrate to obtain the product. Yield: 89.3%. Hydrochloride mp: 140-142° C. $^1$HNMR (ppm, CDCl$_3$) δ: 1.46 (br-s, 4H), 2.25 (s, 3H), 2.61 (br-s, 2H, NH$_2$), 2.93 (m, 4H), 3.10 (d, J=7.0 Hz), 3.39 (d, J=6.72 Hz, 2H), 5.58 (m, 1H), 5.71 (m, 1H), 6.96 (m, 2H), 7.06 (d, J=7.84, 1H).

(2) N-{4-[4-(5-chloro-2-methylphenyl)piperazinyl]-trans-2-buten-1-yl}-benzoxazolin-2-one-6-carboxamide: according to Example 2, benzoxazolin-2-one-6-formyl chloride and trans-4-[4-(5-chloro-2-methylphenyl)piperazinyl]-2-buten-1-amine were subjected to acylation in the presence of sodium carbonate as deacidficating agent to provide the product. Yield: 88.6%, mp: 250-252° C. $^1$HNMR δ (ppm, DMSO-d$_6$): 2.19 (s, 3H), 2.83 (br-s, 4H), 3.31 (s, br., 2H), 3.88 (s, br., 4H), 3.91 (d, J=1.15 Hz, 2H), 5.67 (m, 2H), 6.97 (t, J=1.96 Hz, 2H), 7.16 (q, J=4.48 Hz, 2H), 7.75 (m, 2H), 8.63 (br-s, 1H).

Example 6

Preparation of N-{4-[4-(5-chloro-2-methylphenyl)piperazinyl]-cis-2-buten-1-yl}-benzoxazolin-2-one-5-carboxamide (Compound 6)

(1) Cis-4-[4-(5-chloro-2-methylphenyl)piperazinyl]-2-buten-1-amine: according to the method of Example 5, phthalimide potassium salt was reacted with cis-1,4-dihydro-2-butene to obtain N-(cis-4-chloro-2-buten-1-yl)phthalimide; which was then reacted with 5-chloro-2-methylphenylpiperazine to obtain N-{4-[4-(5-chloro-2-methylphenyl)piperazinyl]-cis-2-buten-1-yl}phthalimide, which was then reacted with hydrazine hydrate. Yield: 85.7%. Hydrochloride mp: 127-129° C. $^1$HNMR (ppm, CDCl$_3$) δ: 1.56 (br-s, 4H), 2.23 (s, 3H), 2.71 (br-s, 2H, NH$_2$), 2.96 (m, 4H), 3.12 (d, J=7.0 Hz), 3.41 (d, J=6.72 Hz, 2H), 5.60 (m, 1H), 5.73 (m, 1H), 6.96 (m, 2H), 7.08 (d, J=7.84, 1H).

(2) N-{4-[4-(5-chloro-2-methylphenyl)piperazinyl]-cis-2-butyl}-benzoxazolin-2-one-5-carboxamide: according to the method of Example 5, benzoxazolin-2-one-5-formyl chloride and cis-4-[4-(5-chloro-2-methylphenyl)piperazinyl]-2-butenyl-1-amine were subjected to acylation in the presence of sodium carbonate as deacidficating agent to obtain the product. Yield: 86.3%, mp: 251-253° C. $^1$H-NMR (ppm, CDCl$_3$) δ: 2.20 (s, 3H), 2.49 (m, 4H), 2.84 (br-s, 4H), 3.12 (d, J=6.44 Hz, 2H), 3.97 (t, J=5.60, 2H), 5.62 (m, 2H), 6.99 (m, 2H), 7.17 (d, J=9.1 Hz, 1H), 7.36 (d, J=8.4 Hz 1H), 7.66 (m, 2H).

Example 7

Preparation of N-{4-[4-(2-methyloxyphenyl)piperazinyl]-trans-2-buten-1-yl}-benzoxazolin-2-one-5-carboxamide (Compound 7)

(1) Trans-4-[4-(2-methyloxyphenyl)piperazinyl]-2-buten-1-yl-amine: according to the method of Example 5, N-(trans-4-chloro-2-buten-1-yl)phthalimide was reacted with 1-(2-methyloxyphenyl)piperazine to obtain N-{4-[4-(2-methyloxy-phenyl)piperazinyl]-trans-2-buten-1-yl}phthalimide, which was then reacted with hydrazine hydrate. Yield: 85.6%, hydrochloride mp: 178-180° C.

(2) N-{4-[4-(2-methyloxyphenyl)piperazinyl]-trans-2-buten-1-yl}-benzoxazolin-2-one-5-carboxamide: according to the method of Example 1, benzoxazolin-2-one-5-formyl chloride and trans-4-[4-(2-methyloxyphenyl)piperazinyl]-2-buten-1-amine were subjected to acylation in the presence of sodium carbonate as deacidficating agent to provide the product. Yield: 85.6%, mp: 208-212° C. $^1$H-NMR (ppm, DMSO-d$_6$) δ: 2.99 (m, 4H), 3.09 (m, 2H), 3.78 (s, br., 4H), 3.79 (s, 3H), 3.96 (t, J=5.6 Hz, 2H), 5.73 (m, 1H), 6.02 (m, 1H), 6.92 (m, 2H), 6.98 (m, 2H), 7.36 (d, J=8.4 Hz, 1H), 7.58 (d, J=1.4 Hz, 1H), 7.66 (dd, J$_1$=1.4 Hz, J$_2$=8.4 Hz, 2H), 8.81 (t, J=5.5 Hz, 1H).

Example 8

Preparation of N-{4-[4-(2-methyloxyphenyl)piperazinyl]-trans-2-buten-1-yl}-benzoxazolin-2-one-6-carboxamide (Compound 8)

According to the method of Example 7, trans-4-[4-(2-methyloxyphenyl)piperazinyl]-2-buten-1-yl-amine and benzoxazolin-2-one-6-formyl chloride were subjected to acylation in the presence of sodium carbonate to obtain the product. Yield: 87.5%. mp: 200-202° C. $^1$HNMR (ppm, DMSO-$d_6$) δ: 2.50 (m, 4H), 2.96 (s, br., 4H), 3.31 (m, 2H), 3.75 (s, 3H), 3.89 (t, 2H), 5.62-5.67 (m, 2H), 6.86 (m, 2H), 6.91 (m, 2H), 7.14 (d, J=8.2 Hz, 1H), 7.73-7.77 (m, 2H), 8.63 (t, J=5.6 Hz, 1H).

Example 9

Preparation of N-{4-[4-(2-methyloxyphenyl)piperazinyl]butyl}-benzothiazolin-2-one-6-carboxamide (Compound 9)

(1) 4-amino-3-thiocyano-benzonitrile: 10.0 g (0.08 mol) p-aminobenzonitrile, 13.0 g (0.17 mol) ammonium thiocyanate were dissolved in 100 ml glacial acetic acid, added dropwise with a glacial acetic acid solution in which 4 mL was dissolved under cooling in an ice-water bath. After the addition, the reaction was performed under stirring for 3 h, and continued at room temperature for 30 min. After the end of reaction, the reaction mixture was added with water to promote precipitation, stood overnight, filtered to collect the precipitate, washed with a small amount of water, dried out to obtain an orange-yellow solid product 13.2 g (89.7%). mp 168-170° C. $^1$H-NMR δ (ppm, $d_6$-DMSO): 6.68 (d, J=8.68 Hz, 1H), 6.96 (br-s, 2H, NH$_2$), 7.58 (dd, J$_1$=8.70 Hz, J$_2$=1.68 Hz, 1H), 7.96 (d, J=1.60 Hz, 1H).

(2) 2-amino-benzo[d]thiazole-6-carboxylic acid: 13.0 g (0.07 mol) 4-amino-3-thiocyano-benzonitrile was weighed, dissolved in 120 ml water, stirred uniformly, added with 60 ml concentrated hydrochloric acid, reacted under refluxing and stirring at about 100° C. for 6 h. After the reaction, the reaction mixture was stood, filtered to obtain a precipitated solid, and dried out to obtain a light yellow solid product 8.5 g (59.0%). mp 280-282° C. $^1$H-NMR (ppm, $d_6$-DMSO) δ: 7.45 (d, J=8.40 Hz, 1H), 7.67 (dd, J$_1$=8.40 Hz, J$_2$=1.68 Hz, 1H), 8.22 (d, J=1.68 Hz, 1H), 8.51 (br-s, 2H, NH$_2$).

(3) 4-amino-3-thio-benzoic acid: 25.0 g potassium hydroxide was weighed, dissolved in 50 ml water, slightly cooled, added with 8.3 g (0.04 mol) 2-amino-benzo[d]thiazole-6-formic acid under nitrogen gas protection, reacted under refluxing and stirring for 24 h, after the end of reaction, cooled with ice bath, added with hydrochloric acid for acidification, stood and filtered to obtain a white solid product 5.2 g (67.9%). mp 280-284° C. $^1$H-NMR δ (ppm, $d_6$-DMSO): 6.75 (d, J=8.69 Hz, 1H), 7.46 (d, J=1.96 Hz, 1H), 7.63 (dd, J$_1$=1.96 Hz, J$_2$=8.40 Hz, 1H), 12.13 (br-s, 1H, CO$_2$H).

(4) benzothiazolin-2-one-6-carboxylic acid: 5.0 g (0.03 mol) 4-amino-3-mercapto-benzoic acid was weighed, added under stirring to 40 mL aqueous solution in which 5.3 g (0.05 mol) anhydrous sodium carbonate was dissolved, under protection of nitrogen gas, heated in 45° C. oil bath, added dropwise with 4.3 g (0.04 mol) methyl chloroformate, after addition, reacted under stirring for 0.5 h, then heated to 80° C. for reaction overnight. On the next day, acidification was carried out under ice-water to pH2-3, a solid was obtained by filtration, washed with a small amount of cold water, dried to obtain a white powdery solid 4.8 g (82.2%), mp 322-328° C. $^1$H-NMR δ (ppm, $d_6$-DMSO): 7.1 (d, J=8.40 Hz, 1H), 7.8 (dd, J$_1$=8.40 Hz, J$_2$=1.68 Hz, 1H), 8.18 (d, J=1.68 Hz, 1H), 12.25 (br-s, 1H, NH), 12.89 (br-s, 1H, CO$_2$H). MS (ESI$^-$, m/z): 194.2 (M−1).

(5) N-{4-[4-(2-methyloxyphenyl)piperazinyl]butyl}-benzothiazolin-2-one-6-carboxamide: according to the method of Example 3, benzothiazolin-2-one-6-carboxylic acid was used to prepare benzothiazolin-2-one-6-formyl chloride, which was then reacted with 4-[4-(2-methyloxyphenyl)piperazinyl]butylamine, and acylated in the presence of sodium carbonate as deacidificating agent. Yield: 81.0%. mp: 154-159° C. $^1$H-NMR (ppm, CDCl$_3$) δ: 1.58 (m, 4H), 1.72 (m, 2H), 2.79 (br., 4H), 3.11 (br., 4H), 3.49 (m, 2H), 3.85 (s, 3H), 6.86 (m, 2H), 6.98 (m, 2H), 7.08 (d, J=8.4 Hz, 1H), 7.62 (dd, J$_1$=1.7 Hz, J$_2$=8.4 Hz, 1H), 7.83 (d, J=1.7 Hz, 1H).

Example 10

Preparation of N-{4-[4-(5-chloro-2-methylphenyl)piperazinyl]-butyl}-benzothiazolin-2-one-6-carboxamide (Compound 10)

According to the method of Example 1, 4-[4-(5-chloro-2-methylphenyl)piperazinyl]butylamine and benzothiazolin-2-one-6-formyl chloride were subjected to acylation in the presence of sodium carbonate as deacidificating agent to obtain a product. Yield: 79.6%. mp: 216-220° C. $^1$H-NMR (ppm, DMSO-$d_6$) δ: 1.51 (m, 2H), 1.73 (m, 2H), 2.04 (s, 3H), 2.19 (s, br., 4H), 3.13 (br, 4H), 3.35 (m, 2H), 7.13 (m, 2H), 7.15 (m, 2H), 7.17 (d, J=8.2 Hz, 1H), 7.76 (dd, J$_1$=1.7 Hz, J$_2$=8.2 Hz, 1H), 8.05 (d, J=1.7 Hz, 1H).

Example 11

Preparation of N-{4-[4-(2-methyloxyphenyl)piperazinyl]-trans-2-buten-1-yl}-benzothiazolin-2-one-6-carboxamide (Compound 11)

According to the method of Example 7, trans-4-[4-(2-methyloxyphenyl)piperazinyl]-2-butenylamine reacted with benzothiazolin-2-one-6-formyl chloride for acylation in the presence of sodium carbonate to obtain a product. Yield: 80.7%. mp: 160-164° C. $^1$H-NMR (CDCl$_3$) δ: 2.76 (s, br., 4H), 3.13 (s, br., 6H), 3.85 (s, 3H), 4.08 (t, J=5.3 Hz, 2H), 5.79 (m, 2H), 6.84 (m, 2H), 6.90 (m, 2H), 7.05 (d, J=8.2 Hz, 1H), 7.63 (dd, J$_1$=1.7 Hz, J$_2$=8.2 Hz, 1H), 7.78 (d, J=1.7 Hz, 1H).

Example 12

Preparation of N-{4-[4-(2-methyloxyphenyl)piperazinyl]butyl}-benzothiazolin-2-one-5-carboxamide (Compound 12)

(1) 3-amino-4-mercaptobenzoic acid: 100 g (0.53 mol) 4-chloro-3-nitrobenzoic acid was suspended in 400 mL water, added as one batch to 300 mL aqueous solution in which 300 g (1.25 mol) sodium sulfide was dissolved, the reaction liquid reacted under stirring and refluxing for 7 h, cooled, neutralized with acetic acid to pH7.5, decolorized with active carbon, filtered, acidificated with acetic acid again to pH4.5, a solid was obtained by filtration, washed with water, crystallized with methanol-water to obtain a yellow solid 62.5 g (62.5%), mp: 185° C. (dec.).

(2) benzothiazolin-2-one-5-carboxylic acid: it was synthesized by referring to the process for preparing benzothiazolin-2-one-6-carboxylic acid, yield 78.5%, mp: >320° C.

(3) N-{4-[4-(2-methyloxyphenyl)piperazinyl]butyl}-benzothiazolin-2-one-5-carboxamide: 4-[4-(2-methyloxyphenyl)piperazinyl]butylamine 2.70 g (0.010 mol) was dissolved in 60 mL dichloromethane, added under stirring with 2.00 g (0.010 mol) benzothiazolin-2-one-6-carboxylic acid, added with supplementary 15 mL acetone, then added with 1.38 g (0.010 mol) 1-hydroxy-benzotriazole and 2.25 g (0.011 mol) N,N'-dicyclohexylcarbodiimide, added with supplementary 3 mL anhydrous methanol, reacted under stirring overnight. On the next day, the reaction mixture was filtered to remove solid, washed with dichloromethane, organic layers were combined, added with supplementary 4 mL ethanol, added with water, layered, dried, subjected to silica gel column chromatography to obtain a fraction with maximum polarity, concentrated to obtain a viscous product, which was salified with hydrochloric acid-ethyl ether to obtain the target product 3.50 g (73.4%), mp: 135-138° C. $^1$H-NMR (CDCl$_3$) δ: 1.81 (m→br, 2H), 2.05 (m→br, 2H), 3.25 (m→br, 2H), 3.49-3.74 (m, 6H), 4.031 (s, 3H), 4.20 (m→br, 2H), 4.77 (m→br, 2H), 7.044 (d, J=8.12 Hz, 2H), 7.172 (s, 1H), 7.41 (m, 2H), 7.50 (m→br, 1H), 7.604 (d, J=7.00 Hz), 7.977 (br-s, 1H), 8.511 (s, 1H), 12.914 (br-s, 1H).

Example 13

Preparation of N-{4-[4-(5-chloro-2-methylphenyl)piperazinyl]-butyl}-benzothiazolin-2-one-5-carboxamide (Compound 13)

According to the method of Example 12, 4-[4-(5-chloro-2-methylphenyl)piperazinyl]butylamine was used to replace 4-[4-(2-methyloxyphenyl)piperazinyl]butylamine in the synthesis, yield 78.5%, mp: 130-133° C. $^1$H-NMR (ppm, DMSO-d$_6$) δ: 1.59 (m, 2H), 1.78 (m, 2H), 2.231 (s, 3H), 3.10-3.25 (m, 8H), 3.12 (m, 2H), 3.53 (m, 2H), 4.819 (br, 2H), 7.04 (d, J=1.96 Hz, 1H), 7.07 (dd, J$_1$=1.96 Hz, J$_2$=8.12 Hz, 1H), 7.22 (d, J=8.12 Hz, 1H), 7.606 (s, 1H), 7.665 (s, 2H), 8.675 (t, J=5.32 Hz, 1H), 10.838 (br-s, 1H), 12.187 (s, 1H).

The present invention is further illustrated by the following biological activity experiments.

Biological Effect Experiment 1:

Experiment of Binding a Target Compound to Radioligands of Dopamine D3 and D2 Receptor (D2R)

Experimental materials: stably transfected CHO-D3R cell strains and CHO-D2R cell strains, $^3$H-Spiperone, purchased from GE Company, Haloperidol, Quinpirole, purchased from Sigma Company, $^{35}$S-GTPγS purchased from PE Company, GTP-γS, GDP, Tris, EDTA-Na$_2$, EGTA, HEPES, PMSF, PPO and POPOP purchased from Sigma Company, NaCl, KCl, KH$_2$PO$_4$, CaCl$_2$, Glucose, MgSO$_4$, MgCl$_2$ and CaCl$_2$, analytically pure, purchased from Beijing Chemical Reagent Company, dioxane, naphthalene and ethylene glycol, purchased from Beijing Chemical Reagent Company, GF/C filter paper purchase from Whatman Company, the compounds were obtained by the above methods.

Experimental steps: the compounds were weighed separately, when cells reached fusion degree of 90%, the cells were digested, centrifuged at 4° C. under 2000 rpm for 5 min. Supernatant was discarded, and precipitation was performed in 5 mM Tris, 5 mM EDTA.2Na and 5 mM EGTA lysate (pH 7.4), stood on ice for 30 min, subjected to passing through syringe needle (4# needle, 0.45×13 mm disposable syringe) under ice-bast for 5-10 times, 4° C., and centrifuged under 40000 g for 20 min. Supernatant was discarded, precipitate was suspended again in ice-cooled 50 mM Tris-HCl (pH 7.4) buffer solution, subjected to passing through needle for 5-10 times, and centrifuged under 4° C., 40000 g for 20 min. Protein concentration was measured by Coomassie brilliant blue G-250 method. Ice-bath was used for adding to reaction system. The used reaction buffer solution was 50 mM Tris-HCl (pH 7.4) buffer solution comprising 1.5 mM CaCl$_2$, 4 mM MgCl$_2$, 1 mM EDTA, 5 mM KCl and 120 mM NaCl. Radioligand $^3$H-Spiperone with a concentration of 0.15-4.8 nM, membrane protein 25-30 μg/tube were used; non-specific binding tube further comprised Haloperidol 10 μM, various other compounds had a final concentration of 1 μM or 50 nM, the total reaction volume was 0.2 mL, the reaction was carried out under 25° C. water bath for 60 min, filtered under a reduced pressure, loaded with scintillation fluid 1 mL, cpm was measured after a night. The results were shown in Table 1 and Table 2.

TABLE 1

Comparative results of selectivity screening of the target compounds at a concentration of 10$^{-6}$ M on D3R and D2R

| No. | D2R inhibition percentage (%) | D3R inhibition percentage (%) |
| --- | --- | --- |
| NGB2904 | 7.67 ± 9 | 85.88 ± 11 |
| Compound 1 | 56.97 ± 17 | 91.00 ± 11 |
| Compound 6 | 63.60 ± 1 | 68.43 ± 4 |

TABLE 2

Comparative results of affinity and selectivity screening of the target compounds at a concentration of 50 nM on D3R and D2R

| No. | D3R inhibition (%) | D2R inhibition (%) |
| --- | --- | --- |
| NGB2904 | 51.8 ± 6 | 3.87 ± 3 |
| Compound 1 | 67.07 ± 12 | 3.9 ± 3.4 |
| Compound 2 | 86 | 5 |
| Compound 5 | 72 | 0 |
| Compound 6 | 24.4 ± 6 | 2.1 ± 10 |

The compounds of other examples of the present invention also had similar experimental results as the example compounds of the present invention in Table 1 and Table 2.

Biological Effect Experiment 2:

Experiment of Competitive Inhibition Constant Ki for Compound 1 (Y-QA14) to D3R and D2R The experimental method and steps were identical to those of the biological effect experiment 1, the tested compound Y-QA14 had concentrations from 10$^{-16}$ to 10$^{-5}$M, increasing by 10 times from 10$^{-16}$M, including 12 concentrations for the experiment, the obtained data were treated with competitive inhibition curve analysis of OriginPro 7.0 software to calculate K$_i$ values.

Figure 2:
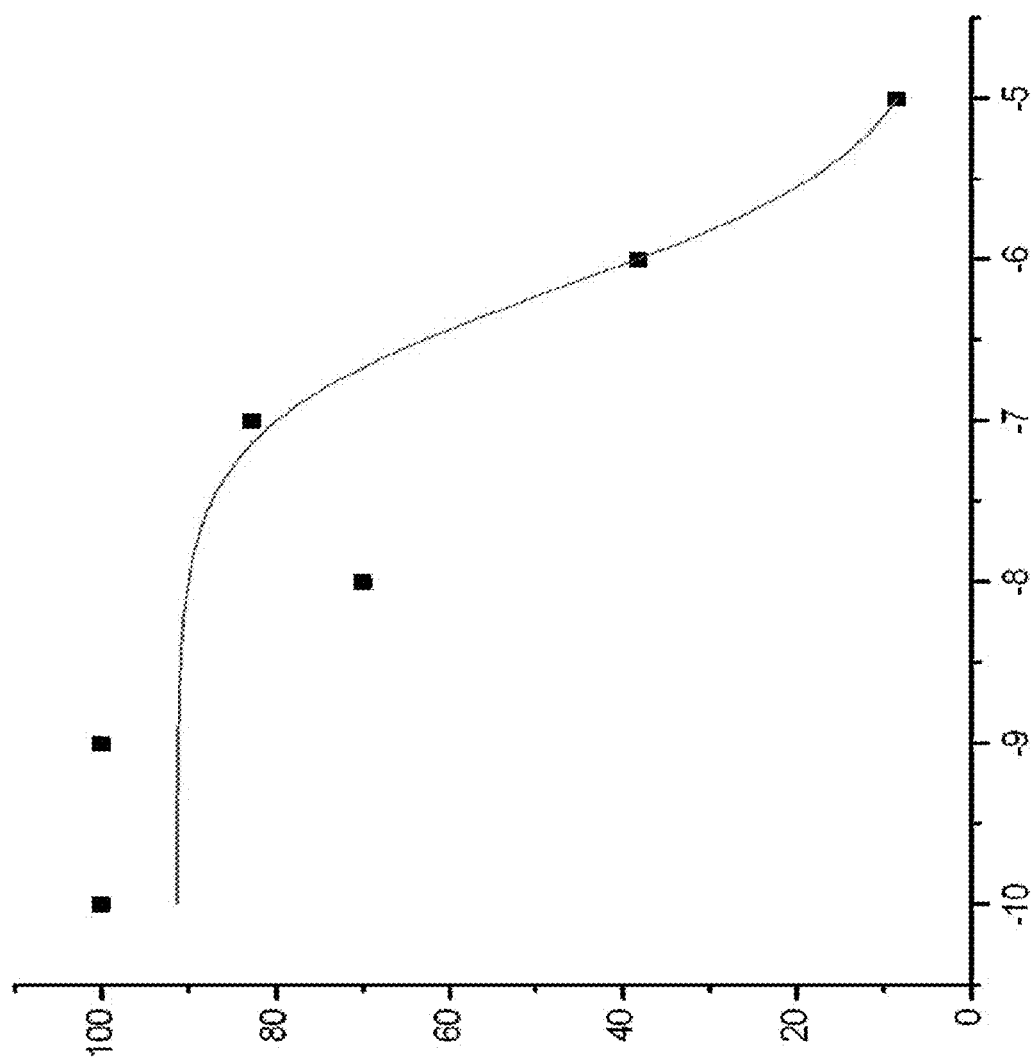
FIG. 2 is a competition-combination curve of Compound 1 of examples to D2R radioligand.

The results were shown in FIG. 1 and FIG. 2. The results indicate that Compound 1 (Y-QA14) has two binding sites at D3R, their Ki values separately are Ki$_H$=0.052±0.003 pM, Ki$_L$=2.03±0.4 nM; while Compound 1 has only one binding site at D2R, Ki is 134.5±10.2 nM. By comparison, it can be seen that Compound 1 has a selectivity of 10$^6$ and 66 times respectively to D3R and D2R, and its value to the high affinity binding site is higher than the D3R compound with high selective in the art by about 1000 times.

Biological Effect Experiment 3:

Studying on Intrinsic Activity of Compound 1 (Y-QA14)

Figure 3:
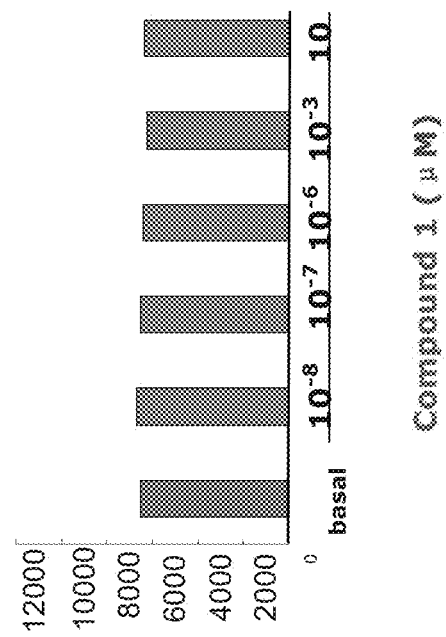
FIG. 3 is a diagram showing the effects of Compound 1 of examples on activity of $^{35}$S-GTPγS binding D3R, in which "basal" represents basis.
Figure 4:
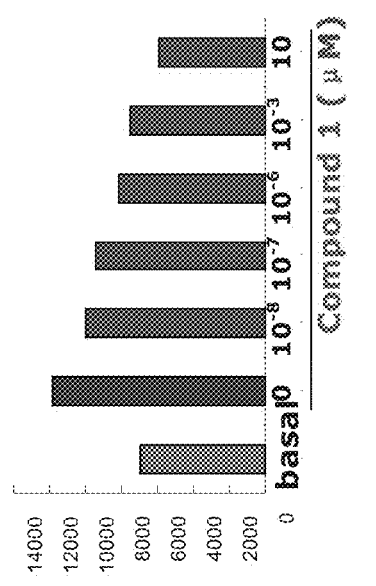
FIG. 4 is a diagram showing the effects of Compound 1 of examples on activity of quinpirole activated $^{35}$S-GTPγS binding D3R, in which "basal" represents basis.

Experimental method: Membrane protein was added to the reaction system under ice-water bath. The reaction buffer was 50 mM Tris-HCl (pH 7.4) buffer, comprising 3 mM MgCl$_2$, 100 mM NaCl and 10 μMGDP. Radioligand $^{35}$S-GTPγS was of 0.17 nM, membrance protein was 40-45 μg/tube; irritant drugs were pre-incubated with protein at 30° C. for 30 min (not adding $^{35}$S-GTPγS), then added with $^{35}$S-GTPγS and incubated at 30° C. for 30 min. Non-specific binding tube further comprised GTPγS 40 μM. The total reaction volume was 0.5 mL, the reaction was terminated with ice-water bath. The reaction liquid was filtrated under a reduced pressure by Whatman-GF/C filter paper, and washed 5 times with cold buffer solution 50 mM Tris-HCl (pH 7.4) containing 5 mM MgCl$_2$ and 50 mM NaCl. The filter paper was dried and placed in 1.5 mL Ep tubes, added with 1 mL scintillation fluid, placed in a scintillation disc, and β liquid scintillation counter was used to record intensity of radiation (cpm). Specific binding amount=total binding amount—non-specific binding amount, multiple tubes were used for each binding site. The data were analyzed by Logistic formula of OriginPro 7.0 software. The results are shown in FIG. 3 and FIG. 4. The results show that in the $^{35}$S-GTPγS binding experiment, single Y-QA14 cannot activate D3R coupling G protein, but it can inhibit the agitation activity of D3R agonist in a concentration dependent way.

Biological Effect Experiment 4:

Influence of Compound 1 (Y-QA14) on Conditioned Place Preference Caused by Morphine in Rats Experimental mechanism: Conditioned Place Preference (CPP) experiment is a classical experimental model in the art currently used for evaluating psychological dependence of drug, in which test animals (rats, mice) are placed in the white viewing area of a conditioned place preference experimental box, administrated with morphine as psychological dependent drug, then the activities of animals in the black and white viewing areas of the conditioned place preference experimental box are observed, the animals are free to move through small doors among black area, white area and grey area. Every time when the animals are in the administration area, they are rewarded with drug to generate a place preference to black or white area, which degree relates to the psychological dependence of the drug.

Experimental materials: animal: wistar rats, male, body weight 180-220 g; reagent: morphine hydrochloride (Qinghai Pharmaceutical Factory); Compound Y-QA14 was synthesized by the inventors.

Instruments: Conditioned Place Preference Instrument for Rats

Preparation of drugs:

Morphine: 10 mg/kg, dissolving 1 mg morphine in 1 mL double-distilled water;

Y-QA14: 1.0 mg/kg, dissolving 0.1 mg Y-QA14 in DMSO, then adding double-distilled water to reach 1 mL; 5.0 mg/kg, dissolving 0.5 mg Y-QA14 in DMSO, then adding double-distilled water to reach 1 mL; 10.0 mg/kg, dissolving 1 mg Y-QA14 in DMSO, then adding double-distilled water to reach 1 mL.

Experimental steps: comprising 3 stages: pre-test stage, training stage and test stage, and operating for consecutive 13 days for completion.

1) Pre-Test Session

In the 1st to 3rd day, the clapboards between two boxes was withdrawn, rats were placed in the middle box, the rats were allowed to run freely in 3 boxes for 15 min, the dwell time of animals in each of the two boxes was measured in order to determine the natural preference to black and white boxes. The box with shorter dwell time for animals was used as drug-box, the white box usually was the drug-box; while the one with longer dwell time was preference box, used as non-drug box.

2) Training Session

In the 4th to 12th day, the clapboards were inserted so that the animals could not move freely between boxes. The experiment was performed every day between 8:30 am and 14:30 am. The animals were trained with saline and drug separately once per day for consecutive 7 days. The animals of 3 Y-QA14 dose groups were abdominally administered with various doses of Y-QA14, after 20 min, subcutaneously injected with morphine 10 mg/kg and then placed immediately in the white box (drug box) for 45 min, or subcutaneously injected with saline and then placed immediately in the black box (non-drug box) for 45 min, circulated once per day. The animals of the solvent group were abdominally administered with saline, after 30 min, subcutaneously injected with solvent and then placed immediately in the white box, subcutaneously injected with saline and then placed immediately in the black box (non-drug box) for 45 min, circulated once per day.

3) Test Session

On the 13th day, the clapboards were withdrawn between two boxes, the mice were placed in the middle box, and allowed to run freely in the 3 boxes from 15 min, and the dwell time of the mice in the white box (drug box) was recorded by computer.

Five groups were used in the experiment: (1) solvent+physiological saline; (2) morphine+solvent; (3) morphine+Y-QA14 1.0 mg/kg; (4) morphine+Y-QA14 5.0 mg/kg; (5) morphine+Y-QA14 10.0 mg/kg.

Figure 5:
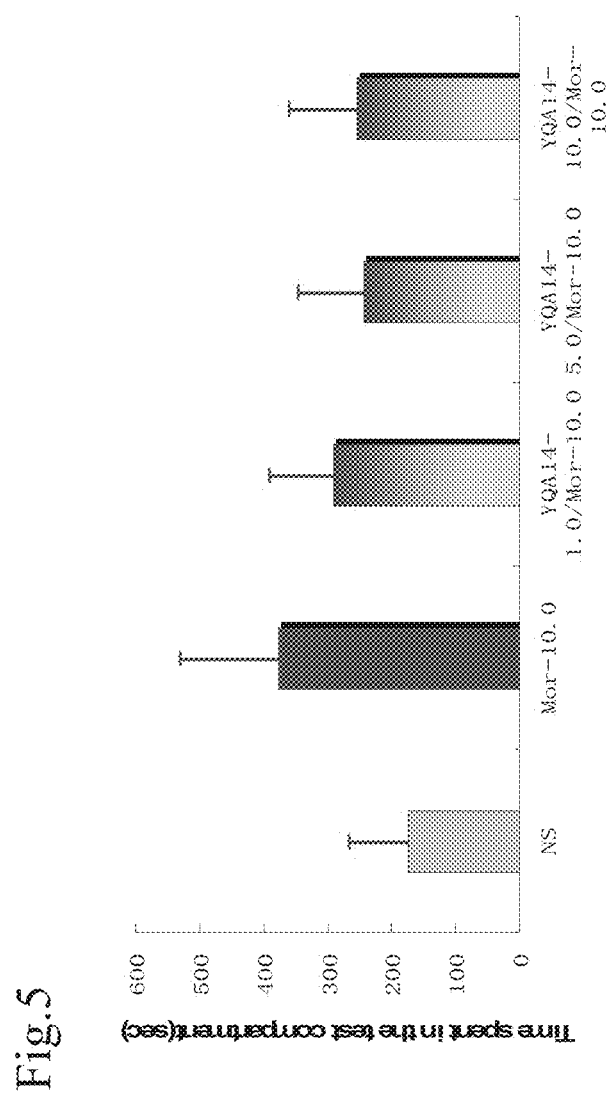
FIG. 5 is a diagram showing the effects Compound 1 (Y-QA14) of examples on the conditioned place preference caused by morphine in rats, in which as compared to the saline group, **P<0.005; as compared to the morphine group, #P<0.02; mean±SD; n=10; and "Time spent in the test compartment (sec)" of the ordinate represents the time (s) spending in the test interval zone.

Experimental results: the dwell times of mice of various groups in the drug box were compared; the data were statistically analyzed by single factor multi-level variance analysis. The results were shown in FIG. 5. The experimental results show that in the experiment of conditioned place preference caused by morphine in rats, Y-QA14 at two dose levels 5 mg/kg and 10 mg/kg can significantly inhibit the occurrence of conditioned place preference caused by morphine.

Biological Effect Experiment 5:

Observation of Compound 1 (Y-QA14) Against Mental Diseases

Experimental object: two pharmacological experimental methods for representing center dopamine functions and behaviors were used, using typical antipsychotic drug haloperidol as reference, preliminarily discussing the possibility of using Y-QA14 as potential antipsychotic drug.

Experimental materials: animals: Kunming mice, male, body weight 20-30 g; reagents: amfetamine (SIGMA); apomorphine (SIGMA); haloperidol (the Institute of Toxicology and Pharmacology, the Academy of Military Medical Sciences); Compound Y-QA14 was synthesized by the inventors.

Preparation of drugs: amfetamine was prepared with distilled water; apomorphine and haloperidol were prepared by dissolving in 0.5N hydrochloric acid and adding with 5% DMSO aqueous solution; Y-QA14 was dissolved in DMSO and diluted with water.

Experimental Method:

1) Apomorphine Mice Climbing Test

Mice were subcutaneously injected with apomorphine 2 mg/kg as dopamine agonist, placed in a metal wire cage, apparent climbing behavior occurred in the animals after 5 min, animals which climbed cage wall and suspended without limbs in contact with the ground for consecutive 20s or more were positive animals, the action peak was reached after 15-30 min in the injected model animals. Antipsychotic drug haloperidol and Y-QA14 were intraperitoneally injected before 30 min of apomorphine administration. The climbing rates of positive animals measured after 15 min and 30 min of apomorphine administration in each group were recorded and compared, the higher one was used in calculation (see: Moore N A et al. J Clin Psychiatry 1997, 58 (Suppl 10): 37-44).

2) Test of Hyperactivity in Amfetamine Mice

Mice which was subcutaneously injected with 6 mg/kg amfetamine after 15 min showed an increase in spontaneous activity, and placed in an infrared spontaneous activity instrument (Institute of Materia Medica, Chinese Academy of Medical Sciences), each in one box, the activity number in 10 min was recorded. Antipsychotic drug and Y-QA14 were intraperitoneally injected before 15 min of amfetamine administration. The average spontaneous activity numbers of the groups were recorded and compared (see: Moore N A et al. J Clin Psychiatry 1997, 58 (Suppl 10): 37-44).

Experimental Results:

1) Apomorphine Mice Climbing Test

Apomorphine 2 mg/kg, sc caused 87% animals appearing climbing behavior, after being inhibited with haloperidol 0.1 mg/kg, only 25% animals appeared climbing behavior, after being inhibited with haloperidol 0.2 mg/kg, the animals appearing climbing behavior were further reduced to 12.5%. Intraperitoneal injection of Y-QA14 20 mg/kg did not show significant inhibition effect, 30 mg/kg showed partial inhibition, while 40 mg/kg showed significant inhibition, no animal appeared climbing behavior as shown in Table 3.

TABLE 3

Antagonistic effect of intraperitoneal injection of Y-QA14 on apomorphine mice climbing behaviors

| Drug | Dose (mg/kg) | Route | Animal Number | Climbing rate |
|---|---|---|---|---|
| Apomorphine control | 2 | sc | 8 | 7/8 |
| Haloperidol | 0.1 | ip | 8 | 2/8* |
|  | 0.2 | ip | 8 | 1/8** |
| Y-QA14 | 20 | ip | 8 | 8/8 |
|  | 30 | ip | 8 | 6/8 |
|  | 40 | ip | 8 | 0/8** |

Note:
as compared to the control group,
*P < 0.05,
**P < 0.01.

2) Test of Hyperactivity in Amfetamine Mice

Amfetamine 6 mg/kg, sc caused an increase of the number of animals with spontaneous activity by more than 2 times, haloperidol 0.1 mg/kg showed significant inhibition effect, the number of animals with spontaneous activity was reduced to 12%, haloperidol 0.2 mg/kg showed more significant inhibition, the number of animals with spontaneous activity was only 6%, lower than that of normal animals. As for Y-QA14 20 and 30 mg/kg, the number of animals with spontaneous activity was about 75% of the model animals, the number for the 40 mg/kg group was 60% of the model animals, all showed significant inhibition (see Table 4).

TABLE 4

Effects of YQA by intraperitoneal injection on hyperactivity in amfetamine mice

| Drug | Dose (mg/kg) | Route | Animal Number | Number with spontaneous activity (M ± SD) |
|---|---|---|---|---|
| Solvent control |  | ip | 8 | 358.5 ± 51.8 |
| Amfetamine control | 6 | sc | 8 | 953.8 ± 139.9# |
| Haloperidol | 0.1 | ip | 8 | 115.1 ± 65.6** |
|  | 0.2 | ip | 8 | 65.6 ± 111.7** |
| Y-QA14 | 20 | ip | 8 | 728.2 ± 225.6* |
|  | 30 | ip | 8 | 734.1 ± 202.1* |
|  | 40 | ip | 8 | 545.6 ± 221.6** |

Note:
activity increase as compared to the control,
P < 0.05; activity decrease as compared to amfetamine,
*P < 0.05,
**P < 0.01.

The experimental results showed that Y-QA14 can significantly inhibit the climbing behavior caused by apomorphine in mice and the hyperactivity caused by amfetamine in mice, showing Y-QA14 would have potential therapeutic effects on mental diseases.

In the above biological experiments 2-5, the compounds of other examples of the present invention also showed experimental results essentially similar to those of the compound Y-QA14.

Biological Effect Experiment 6:

Effects of YQA14 on cocaine-enhanced brain stimulated reward in rats (Song et al., "Blockade of D3 Receptors by YQA14 Inhibits Cocaine's Rewarding Effects and Relapse to Drug-Seeking Behavior in Rats. Neuropharmacology, 2014 February; 77:398-405, Epub 2013 Oct. 28).

Brain stimulated reward is a highly sensitive experimental procedure to assess whether a substance is rewarding/pleasurable or aversive/dysphoric.

Experiment Materials and Methods:

Male Long-Evans rats weighing 250-300 g were used. Cocaine HCl was dissolved in physiological saline. YQA14 was synthesized by the inventors and dissolved in vehicle, i.e., 25% 2-hydroxypropyl-β-cyclodextrin.

Experiment Apparatus:

The experiments were conducted in standard Med Associates operant chambers. Each operant chamber had a lever located 6.5 cm above the floor, connected to an electrical stimulator.

Experiment Procedure:

Set up the BSR threshold ($\theta_0$) which was defined as the minimum frequency at which the animal responded for rewarding stimulation. Once a baseline $\theta_0$ value was achieved (<15% variation over 5 continuous days), the effects of cocaine and/or YQA14 on BSR were assessed. On test days, animals randomly received one of three different doses of YQA14 (12.5, 25 mg/kg i.p.) or vehicle (1 ml 25% 2-hydroxypropyl-β-cyclodextrin) 30 min prior to a cocaine injection (2 mg/kg i.p.). After each test, animals received an additional 5-7 days of BSR re-stabilization until a new baseline $\theta_0$ was established. The order of testing for various doses of YQA14 was counterbalanced. The effect of YQA14 on cocaine enhanced BSR was evaluated by comparing cocaine-induced alterations in $\theta_0$ value in the presence or absence of each dose of YQA14 pretreatment.

Figure 6A:
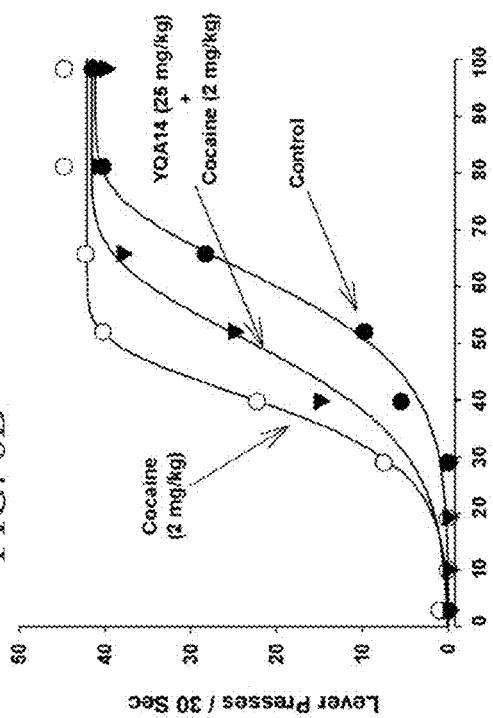
FIGS. 6A-D are graphs showing that YQA14 decreased the cocaine-enhanced brain stimulated reward in rats.
Figure 6B:
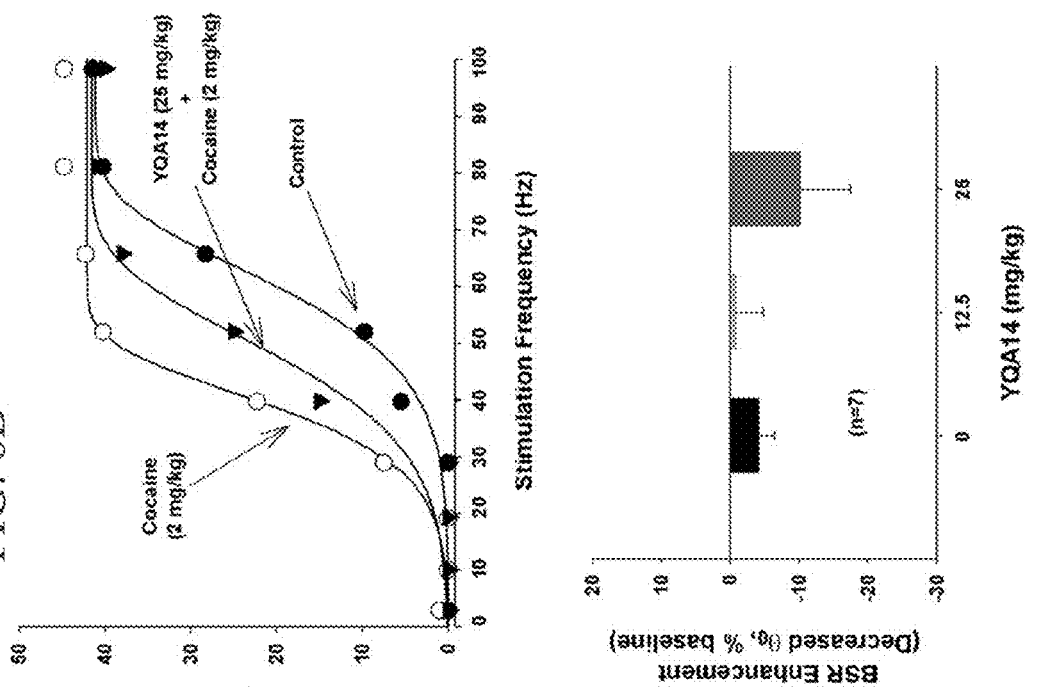
Figure 6C:
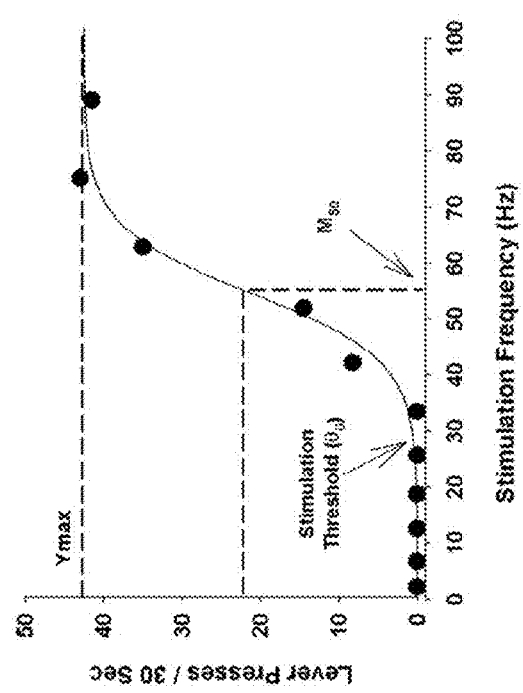
Figure 6D:
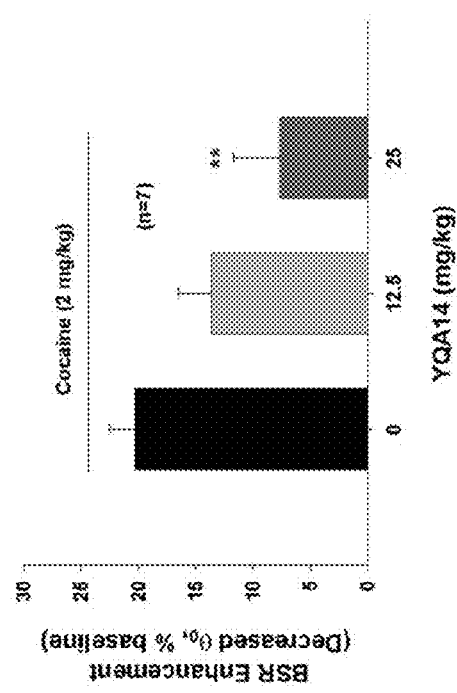

Experiment Results:

YQA14 decreased the cocaine-enhanced brain stimulated reward in rats. Systemic administration of cocaine (1, 2, and 10 mg/kg, i.p.) produced significant and dose dependent enhancement of BSR indicated by a decrease in BSR threshold ($\theta_0$ value) (FIGS. 6A and B). In the present research, we chose the median dose of 2 mg/kg cocaine, which produced a significant decrease in BSR threshold in rats (FIG. 6B). Pretreatment with YQA14 (12.5, 25 mg/kg, i.p.) significantly inhibited the enhanced BSR produced by 2 mg/kg of cocaine (FIG. 6C). YQA14 alone (12.5, 25 mg/kg, i.p.) had no effect on BSR (FIG. 6D). However, one way-ANOVA for the data shown in FIG. 6C revealed a significant YQA14 treatment main effect on cocaine enhanced BSR. Individual group comparisons revealed a statistically significant reduction in cocaine enhanced BSR after 25 mg/kg YQA14 when compared to vehicle group.

Biological Effect Experiment 7:

Effects of YQA14 on cocaine self-administration in rats. (Song et al., "YQA14: A novel dopamine D3 receptor antagonist that inhibits cocaine self-administration in rats and mice, but not in D3-knockout mice," Addiction Biology, 2012, 17 (2):259-73.)

The drug self-administration model presents the most obvious and face-relevant model of addiction.

Experiment Materials and Methods:

Male Long-Evans rats weighing 250-300 g were used. Cocaine HCl was dissolved in physiological saline. YQA14 was synthesized by the inventors and dissolved in vehicle, i.e., 25% 2-hydroxypropyl-β-cyclodextrin. SB-277011A (Trans-N-[4-[2-(6-cyano 1,2,3,4-tetrahydroisoquinolin-2-yl)ethyl]cyclohexyl]-4-quinolinecarboxamide) was synthesized at MegaPharma Kft., Budapest, Hungary.

Experiment Apparatus:

Intravenous cocaine self-administration experiments were conducted in operant response test chambers (32×25×33 cm) (Med Associates, Saint Albans, Vt., USA). Each test chamber had two levers located 6.5 cm above the floor, one active and one inactive.

Experiment Procedure:

1. Fixed-ratio reinforcement schedule: After 5-7 days of recovery from surgery, each rat was placed into a test chamber and allowed to lever-press for i.v. cocaine (1.0 mg/kg/infusion) infusion on a fixed-ratio (FR1) reinforcement schedule until stable cocaine self-administration was established. The initial cocaine dose of 1 mg/kg per infusion was chosen as our previous experience showed that this dose produces rapid and facile acquisition of cocaine self-administration behavior. After transition from FR1 reinforcement, subjects were allowed to continue cocaine (0.5 mg/kg per infusion) self-administration under FR2 reinforcement (7-10 days) until the following criteria for stable cocaine maintained responding were met: less than 10% variability in inter-response interval and less than 10% variability in number of presses on the active lever for at least 3 consecutive days. The range of cocaine (0.031, 0.0625, 0.125, 0.25, 0.5 and 1.0 mg/kg per infusion) in a single session. The session consisted of five sequential 20-minute components, each preceded by a 20-minute timeout period for changing the cocaine dose. The infusion volumes and durations of each component were identical except that cocaine concentrations for corresponding unit cocaine doses differed. There was a 30-minute extinction period (0 mg/kg cocaine) before each daily cocaine self-administration session. Testing continued until stable cocaine-maintained responding was achieved (i.e. a minimum of 10 mg/kg cocaine infusions per session, with less than 10% variation in total number of cocaine injections for 3 consecutive days, and at least fivefold higher maximal response rates compared with those maintained during extinction). Then, each rat randomly received one of three doses of YQA14 (6.25, 12.5 or 25 mg/kg, i.p.) or vehicle (25% 2-hydroxypropyl-β-cyclodextrin) 20 minutes prior to the test session. Additional rats were used to observe the effects of SB-277011A (12.5 or 25 mg/kg i.p.) on cocaine self-administration using the same procedure as described above. Animals then received an additional 5-7 days of self-administration of cocaine alone until baseline response was re-established prior to testing the next dose of YQA14 or SB-277011A. The order of testing for the various doses of drug or vehicle was counterbalance.

2. Progressive ratio reinforcement schedule: After stable cocaine self-administration under FR2 reinforcement was established, subjects were switched to cocaine self-administration (0.5 mg/kg per injection) under PR reinforcement, during which the work requirement (lever presses) needed to receive a single i.v. cocaine infusion was progressively raised within each test session according to the following PR series: 1, 2, 4, 6, 9, 12, 15, 20, 25, 32, 40, 50, 62, 77, 95, 118, 145, 178, 219, 268, 328, 402, 492 and 603 until the break-point was reached. The break point was defined as the maximal workload (i.e. number of lever presses) completed for the last cocaine infusion prior to a 1-hour period during which no infusions were obtained by the animal. Animals were allowed continuing daily sessions of cocaine self-administration under PR reinforcement conditions until day-to-day variability in break-point fell within 1-2 ratio increments for 3 consecutive days. Once a stable break-point was established, subjects were assigned to seven subgroups. Then, each group randomly received vehicle (25% 2-hydroxypropyl-β-cyclodextrin), one of three doses YQA14 (1.00, 6.25 or 12.5 mg/kg, i.p.), or one of three doses of SB-277011A (6, 12 or 25 mg/kg, i.p.) 20 minutes prior to the test session.

Experiment Results:

1. YQA14 Attenuated the Cocaine Self-Administration Under Fixed-Ratio2 (FR2) Reinforcement.

Figure 7A:
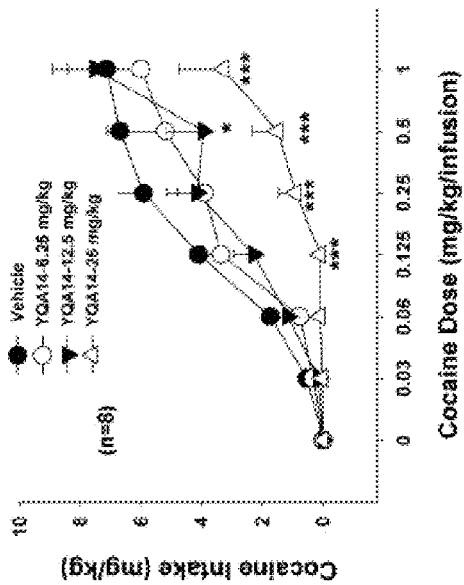
FIGS. 7A-D are graphs showing that YQA14 attenuated the cocaine self-administration under Fixed-Ratio2 (FR2) reinforcement.
Figure 7B:
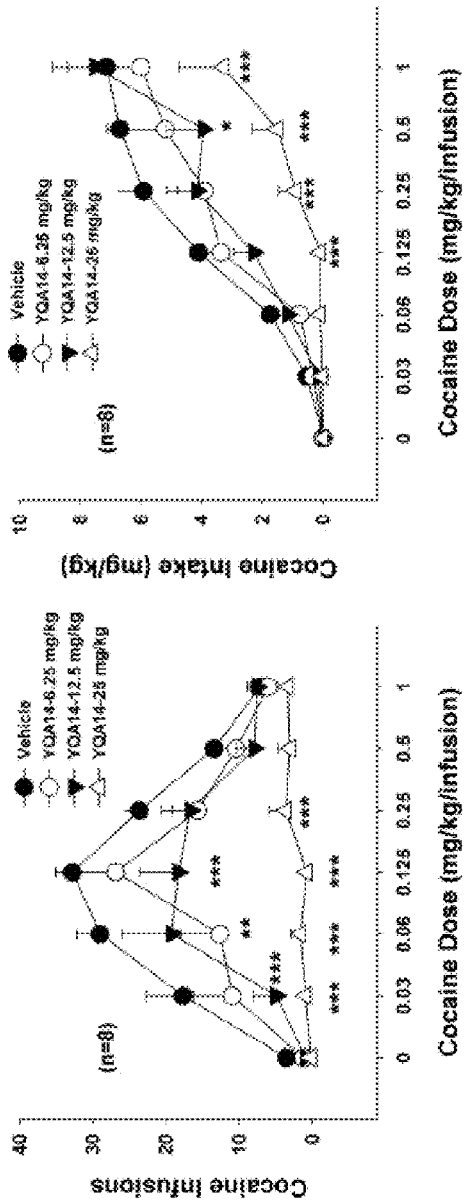
Figure 7C:
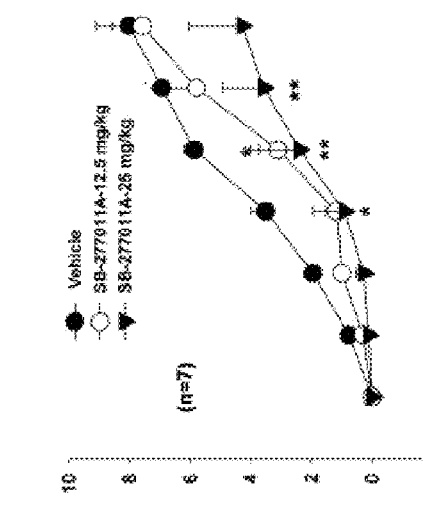
Figure 7D:
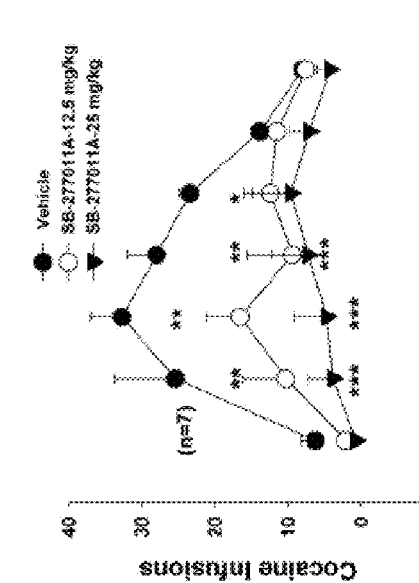

YQA14 (12.5 or 25 mg/kg, i.p.) significantly and dose-dependently inhibited cocaine self administration and shifted the cocaine dose-response self administration curve downward (FIG. 7A) and shifted cocaine intake dose-response curve downward and to the right (FIG. 7B). Two-way ANOVA for repeated measures over cocaine dose revealed a significant treatment (vehicle versus YQA14) main effect (FIG. 7A), significant cocaine dose main effect (FIG. 7A) and a significant treatment X dose interaction (FIG. 7). Individual group comparisons revealed a statistically significant reduction in cocaine self-administration maintained by lower doses (0.03-0.25 mg/kg per infusion) of cocaine after 6.25 mg/kg, 12.5 mg/kg or 25 mg/kg (FIG. 7A, FIG. 7B) YQA14, when compared to the vehicle control group. FIGS. 9C and 9D illustrate that the same doses of SB-277011A also produced a dose dependent inhibition of cocaine self-administration. Two-way ANOVA for repeated measures over cocaine dose revealed a significant treatment (vehicle versus SB-277011A) main effect (FIG. 9C, FIG. 9D), significant cocaine dose main effect (FIG. 7C; FIG. 7D) and a significant treatment×dose interaction (FIG. 7C; FIG. 7D). Individual group comparisons revealed a statistically significant reduction in cocaine self-administration maintained by lower doses (0.03-0.25 mg/kg per infusion) of cocaine after 12.5 mg/kg (FIG. 7C) or 25 mg/kg (FIG. 7C; FIG. 7D) SB-277011A, when compared to the vehicle control group.

2. YQA14 Attenuated the Cocaine Self-Administration Under Progressive-Ratio (PR) Reinforcement.

Figures 8A, 8B:
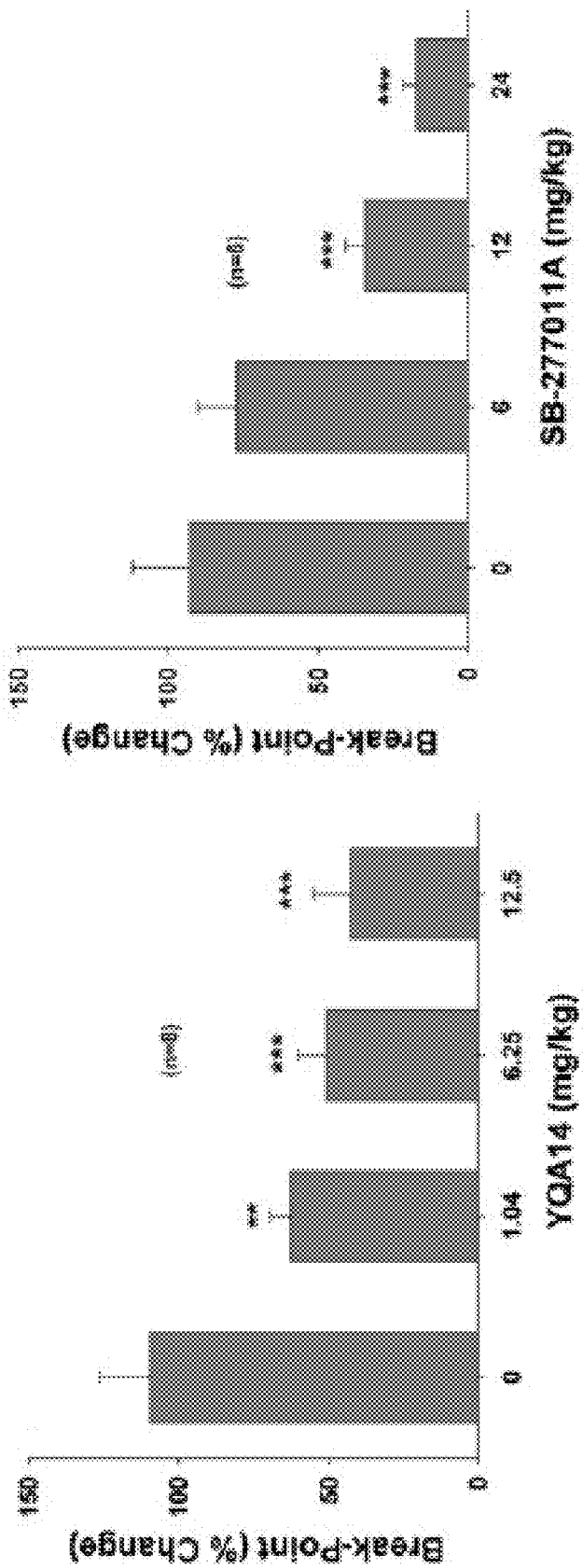
FIGS. 8A-B are graphs showing that YQA14 attenuated the cocaine self-administration under progressive-ratio (PR) reinforcement.

To determine whether the YQA14-induced reduction in cocaine self-administration was due to a reduction in cocaine's rewarding efficacy, we further observed the effects of YQA14 on i.v. cocaine self-administration under progressive-ratio (PR) reinforcement. FIG. 8 shows that systemic administration of YQA14 (1.04, 6.25 and 12.5 mg/kg) or SB-277011A (6, 12 and 24 mg/kg) significantly and dose-dependently lowered break-point for cocaine self-administration (shown as % change).

Biological Effect Experiment 8:

Effects of YQA14 on cocaine-triggered reinstatement of drug-seeking behavior in rats. (Song et al., "Blockade of D3 Receptors by YQA14 Inhibits Cocaine's Rewarding Effects and Relapse to Drug-Seeking Behavior in Rats," *Neuropharmacology*, 2014 February; 77:398-405. doi: 10.1016/j.neuropharm. 2013.10.010. Epub 2013 Oct. 28.)

The drug self-administration model presents the most obvious and face-relevant model of addiction.

Experiment Materials and Methods:

Male Long-Evans rats weighing 250-300 g were used. Cocaine HCl was dissolved in physiological saline. YQA14 was synthesized by the inventors and dissolved in vehicle, i.e., 25% 2-hydroxypropyl-β-cyclodextrin.

Experiment Apparatus:

Intravenous cocaine self-administration experiments were conducted in operant response test chambers (32×25×33 cm) (Med Associates, Saint Albans, Vt., USA). Each test chamber had two levers located 6.5 cm above the floor, one active and one inactive.

Experiment Procedure:

After stable cocaine self-administration was established, additional groups of animals were exposed to the extinction conditions, in which cocaine was replaced by saline, and the cocaine-associated cue-light and tone were turned off. Active lever pressing led only to saline infusion. Daily 3 h extinction sessions for each rat continued until lever presses <10 times per 3 h session for at least 3 consecutive days. On the reinstatement test day, each group of rats received either the vehicle (25% 2-hydroxypropyl-β-cyclodextrin) or one dose of YQA14 (12.5 and 25 mg/kg i.p.). At 30 min after vehicle or YQA14 administration, all rats were given a priming injection of cocaine (10 mg/kg i.p.) immediately before reinstatement testing begun in the same self-administration chambers. During the reinstatement test, lever-pressing responses did not lead to either cocaine infusions or presentation of the conditioned cues. Reinstatement test sessions lasted 3 h. Cocaine-induced lever-pressing responses were recorded and compared between different dose groups of rats.

Experiment Results:

YQA14 inhibited the drug-induced cocaine-seeking behavior.

Figures 9A, 9B:
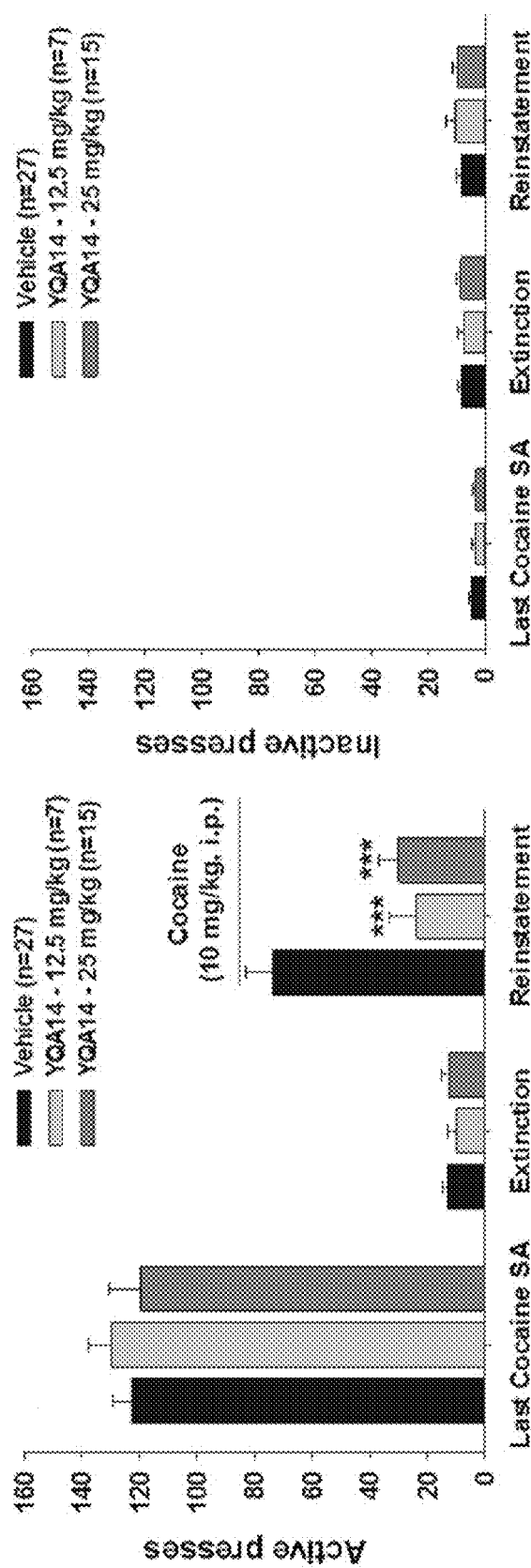
FIGS. 9A-B are graphs showing that YQA14 inhibited the drug-induced cocaine-seeking behavior.

FIG. 9 shows total numbers of active lever presses observed during the last session of cocaine self-administration, the last session of extinction, and the reinstatement test session in two different YQA14 dose groups. A single non-contingent cocaine prime (10 mg/kg) evoked robust reinstatement of cocaine-seeking behavior in rats extinguished from previous cocaine self-administration (FIG. 4A). Pretreatment with YQA14 (12.5, 25 mg/kg) significantly attenuated cocaine-triggered reinstatement of drug-seeking behavior by w60% (FIG. 9A). Individual group comparisons revealed a statistically significant reduction in cocaine-seeking behavior after 12.5 mg/kg YQA14 or 25 mg/kg YQA14, when compared to vehicle control group. In contrast, YQA14 pretreatment did not alter inactive lever response under the same experimental conditions (FIG. 9B), suggesting a specific effect on cocaine-induced drug-seeking behavior.

Biological Effect Experiment 9:

Effects of YQA14 on cue-triggered reinstatement of drug-seeking behavior in rats. (Song et al., "Blockade of D3 Receptors by YQA14 Inhibits Cocaine's Rewarding Effects and Relapse to Drug-Seeking Behavior in Rats," *Neuropharmacology*, 2014 February; 77:398-405. doi: 10.1016/j.neuropharm. 2013.10.010. Epub 2013 Oct. 28.)

The drug self-administration model presents the most obvious and face-relevant model of addiction.

Experiment Materials and Methods:

Male Long-Evans rats weighing 250-300 g were used. Cocaine HCl was dissolved in physiological saline. YQA14 was synthesized by the inventors and dissolved in vehicle, i.e., 25% 2-hydroxypropyl-β-cyclodextrin.

Experiment Apparatus:

Intravenous cocaine self-administration experiments were conducted in operant response test chambers (32×25×33 cm) (Med Associates, Saint Albans, Vt., USA). Each test chamber had two levers located 6.5 cm above the floor, one active and one inactive.

Experiment Procedure:

After stable cocaine self-administration was achieved, additional groups of rats were used to assess contextual cue-induced cocaine-seeking behavior. After 14 days of withdrawal from cocaine self-administration, animals were divided into 3 dose groups (0, 12.5, 25 mg/kg YQA14). At 30 min after injection on the test day, the rats were re-placed into the same self-administration chambers, and contextual cue-induced cocaine-seeking behavior was assessed under extinction conditions during which cocaine and the cocaine-associated cue light and tone were unavailable, and therefore, lever pressing did not result in any consequence. Each reinstatement test lasted for 3 h.

Experiment Results:

YQA14 Inhibited the Cue-Induced Cocaine-Seeking Behavior.

Figures 10A, 10B:
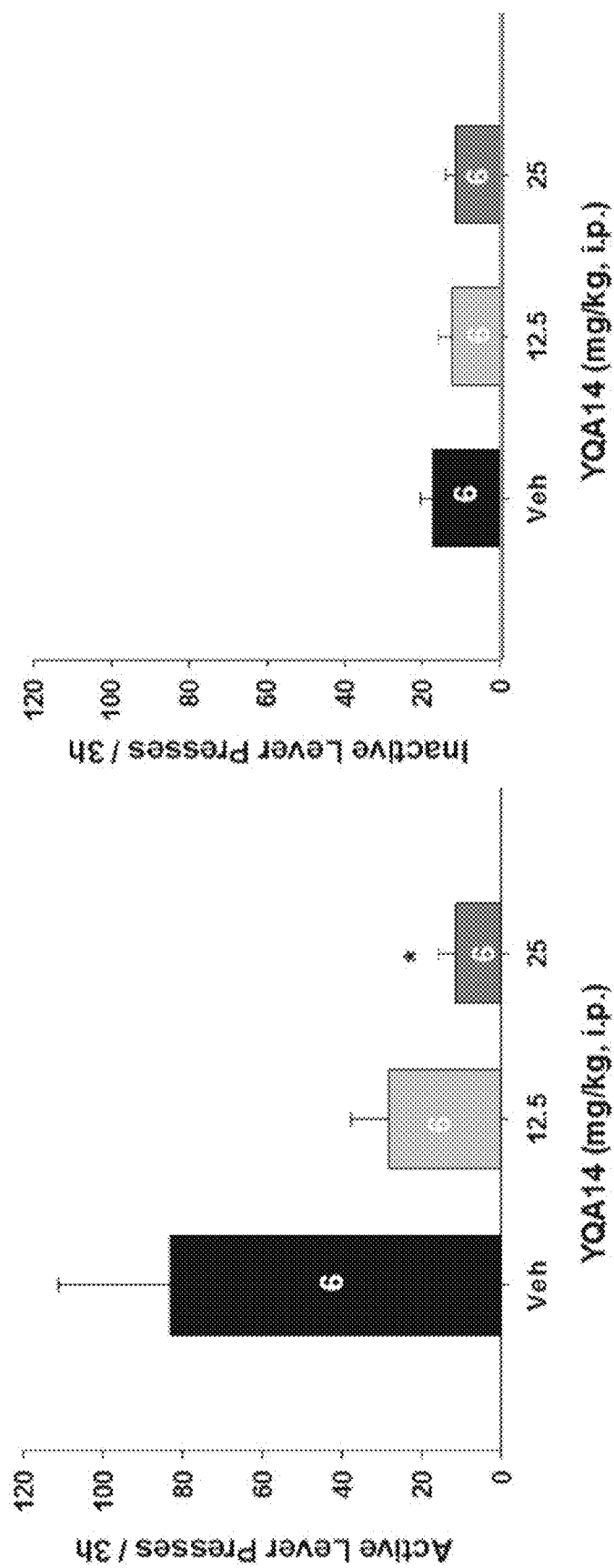
FIGS. 10A-B are graphs showing that YQA14 inhibited the cue-induced cocaine-seeking behavior.

FIG. 10 shows lever responses on both active and inactive levers in rats after 14 days of withdrawal from cocaine self-administration. Pretreatment with YQA14 (12.5, 25 mg/kg) on the test day significantly and dose-dependently attenuated contextual cue-induced cocaine-seeking behavior. One-way ANOVA revealed a statistically significant YQA14 treatment main effect on active lever presses (FIG. 10A). Individual group comparisons revealed a significant reduction in active lever pressing after 25 mg/kg, when compared to vehicle control group. In contrast, systemic administration of YQA14 did not alter inactive lever responses (FIG. 10B).

Biological Effect Experiment 10:

Effects of YQA14 on cocaine-induced behavior sensitization in rats. (Song et al., "Blockade of D3 Receptors by YQA14 Inhibits Cocaine's Rewarding Effects and Relapse to Drug-Seeking Behavior in Rats," *Neuropharmacology*, 2014 February; 77:398-405. doi: 10.1016/j.neuropharm. 2013.10.010. Epub 2013 Oct. 28.)

Locomotor hyperactivity is one of the most commonly used paradigms to study drug's acute rewarding and psychostimulating effects. Behavioral sensitization has been proposed as a useful paradigm to learn the mechanism of psychostimulant addiction.

Experiment Materials and Methods:

Male Long-Evans rats weighing 250-300 g were used. Cocaine HCl was dissolved in physiological saline. YQA14 was synthesized by the inventors and dissolved in vehicle, i.e., 25% 2-hydroxypropyl-β-cyclodextrin.

Experiment Apparatus:

The locomotor detection chamber (Accuscan, Columbus, Ohio, USA)

Experiment Procedure:

Before receiving cocaine or YQA14, rats were placed in a locomotor detection chamber (Accuscan, Columbus, Ohio, USA) for habituation for 1 h per day for 3 days. Rats were then divided into three groups. One group of rats were used to study the effects of daily administration of YAQ14 (0, 12.5, 25 mg/kg/day, 20 min prior to cocaine, n=8 per group) on acquisition of cocaine (15 mg/kg/day×7 days)-induced locomotor sensitization. The second group of rats were used to study the effects of a single injection of YQA14 (0, 12.5, 25 mg/kg, n ¼9e12 per dose group) on expression of cocaine-induced locomotor sensitization in rats 7 days after the last cocaine injection. The third groups of rats were used to study the effects of repeated administration of YQA14 (25 mg/kg×7 days) alone on basal locomotor activity. On the test day, rats were placed into the locomotion detection chambers to measure locomotion immediately after received 10 mg/kg cocaine or YQA14. Total distance counts were used to evaluate the effect of YQA14 on basal and cocaine-induced behavioral sensitization.

Experiment Results:

Chronic Injection of YQA14 Inhibited the Development of Cocaine Induced Behavior Sensitization.

Figures 11A, 11B:
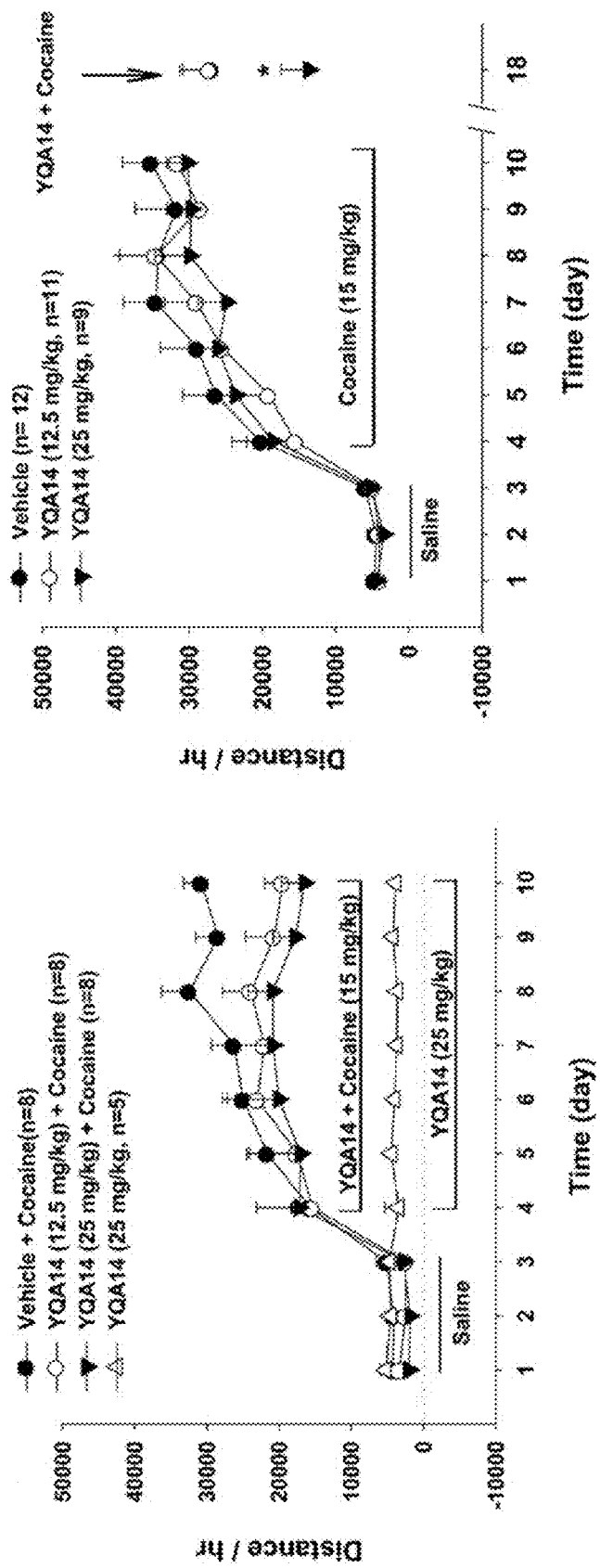
FIGS. 11A-B are graphs showing that chronic injection of YQA14 inhibited the development of cocaine induced behavior sensitization.

FIG. 11A shows that pretreatment with YQA14 (12.5, 25 mg/kg), administered 20 min prior to each cocaine injection for 7 days, did not produce a statistically significant inhibitory effect on acquisition of repeated cocaine-induced locomotor sensitization. Two-way ANOVA for repeated measures over time revealed a statistically significant time main effect, but non-significant YQA14 treatment main effect nor treatment×time interactions. Repeated administration of YQA14 alone failed to alter spontaneous locomotion when compared to the basal levels of locomotion after saline injection (FIG. 11A). FIG. 11B shows that pretreatment with YQA14 significantly inhibited the expression of cocaine-induced locomotor sensitization measured 7 days after the last cocaine injection.

Biological Effect Experiment 11:

Effects of YQA14 on cocaine-induced conditioned place preference in mice. (Song et al., "Dopamine D3 receptor deletion or blockade attenuates cocaine-induced conditioned place preference in mice," *Neuropharmacology*, 2013, (7) 82-87.)

Conditioned Place Preference (CPP) experiment is a classical experimental model in the art currently used for evaluating psychological dependence of drug, in which test animals (rats, mice) are placed in the white viewing area of a conditioned place preference experimental box, administrated with morphine as psychological dependent drug, then the activities of animals in the black and white viewing areas of the conditioned place preference experimental box are observed, the animals are free to move through small doors among black area, white area and grey area. Every time when the animals are in the administration area, they are rewarded with drug to generate a place preference to black or white area, which degree relates to the psychological dependence of the drug.

Experiment Materials and Methods:

Male wild-type (WT) and $D_3R$ knockout ($D_3^{-/-}$) mice with C57BL/6J genetic backgrounds were bred at the National Institute on Drug Abuse (NIDA) from three $D_3^{+/-}$ breeding pairs purchased from the Jackson Laboratory (Bar Harbor, Me., USA). Cocaine HCl was dissolved in physiological saline. YQA14 was synthesized by the inventors and dissolved in vehicle, i.e., 25% 2-hydroxypropyl-β-cyclodextrin.

Experiment Apparatus:

The CPP apparatus (MED-CPP-3013, Med Associates, Georgia, Vt., USA) composed of two large compartments (17.4×12.7×12.7 cm³) and a center corridor (11.7×12.7×12.7 cm³).

Experiment Procedure:

Pre-Conditioned Phase:

On days 1-3, mice were placed in the center corridor and provided free access to the other two compartments for 20 min daily. The time spent in each compartment was recorded. This habituation was to eliminate biased mice (defined operationally as spending over 800 sec in either compartment).

Cocaine-Conditioning Phase:

On each of the next 10 days (days 4-13) mice received vehicle (saline) or one dose of cocaine (5, 10, 20 mg/kg, i.p.) on alternating days in 4 separate groups of mice corresponding to the four cocaine doses, after which each mouse was confined to a randomly designated treatment-appropriate CPP compartment for 15 min.

YQA14-Conditioning Phase:

We used additional two groups of mice (n=12 per group) to determine whether YQA14 alone produces CPP or CPA. After pre-conditioning, mice received vehicle (25% β-cyclodextrin) or one dose of YQA14 (25, 30 mg/kg, i.p.) on each of the next 10 days (days 4-13) on alternating days. Then each mouse was confined to a randomly designated treatment-appropriate CPP compartment for 15 min.

Test Phase:

On day 14, the mice were again placed in the center corridor and provided free access to the other two compartments for 15 min. In this phase, no cocaine or saline was given. The computer recorded the time spent in the each chamber. The preference (i.e., CPP score) was assessed by time (sec) spent in the cocaine- or YQA14-paired compartment minus time spent in the vehicle-paired compartment.

1. Effects of YQA14 on Acquisition of Cocaine-Induced CPP in WT and $D_3^{-/-}$ Mice We then investigated whether blockade of $D_3R$ by YQA14 alters cocaine-induced CPP, as seen by $D_3R$ deletion. Three groups of WT mice (n=9-12 per group, between-subjects design) and three groups of $D_3^{-/-}$ mice (n=6-12 per group) were used to study the effects of chronic daily YQA14 administration on acquisition of cocaine-induced CPP. During the 10 days of conditioning, each mouse was given vehicle (25% 2-hydroxypropyl-β-cyclodextrin) or one dose of YQA14 (25 or 50 mg/kg) 30 min prior to the daily cocaine or saline injection. The cocaine dose was 20 mg/kg, and each animal received a total of 10 daily YQA14 injections. On the test day, CPP was measured in the absence of any drug treatment (no YQA14, no vehicle, no cocaine, and no saline).

2. Effects of YQA14 on Expression of Cocaine-Induced CPP in WT and $D_3^{-/-}$ Mice Three groups of WT mice (n=7-8 per group) and three groups of $D_3^{-/-}$ mice (n=7-9 per group) were used to study the effects of a single injection of YQA14 on expression of cocaine-induced CPP on the CPP test day. The cocaine dose was 20 mg/kg. YQA14 (25 or 50 mg/kg i.p.) was given 30 min prior to testing on the test day in the absence of cocaine or saline injection.

Figure 12B:
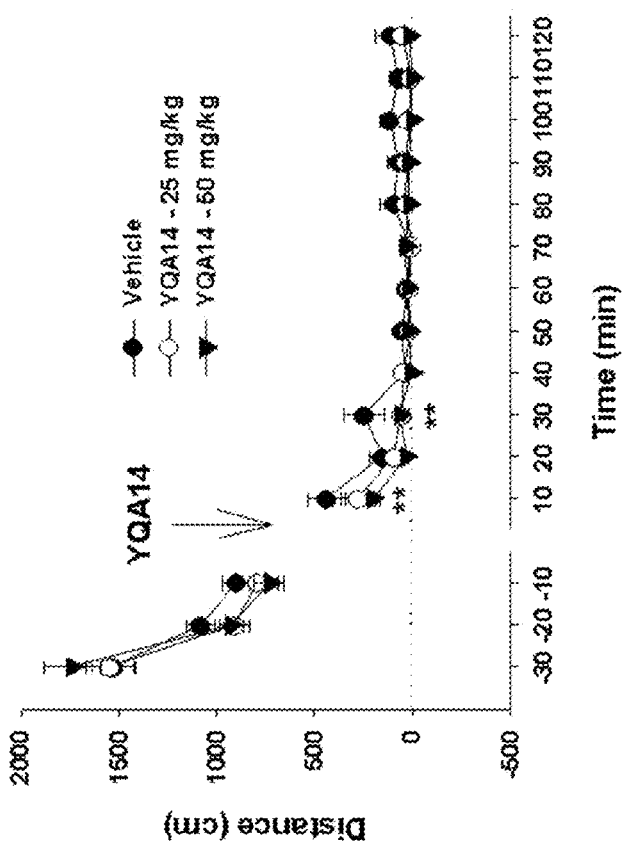
FIGS. 12A-B are graphs showing that YQA14 itself failed to produce CPP or CPA in WT mice, but moderately inhibited locomotor behavior.
Figure 12A:
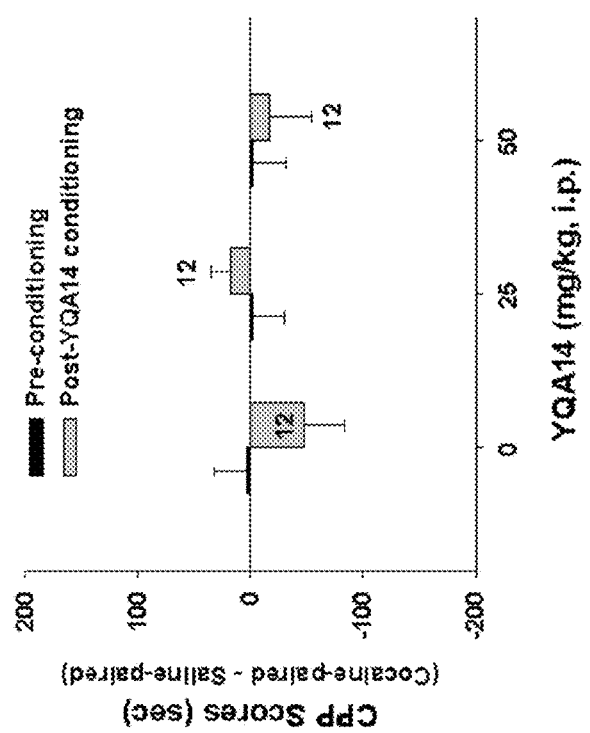

Experiment Results:

1. YQA14 Itself Failed to Produce CPP or CPA in WT Mice, but Moderately Inhibited Locomotor Behavior Firstly, to determine whether such a reduction in cocaine-induced CPP was due to YQA14-induced CPA or locomotor inhibition, we used the same CPP procedures as those for cocaine to measure YQA14-induced CPP/CPA and locomotion. We found that YQA14 did not produce CPP or CPA by itself (FIG. 12A: 25 mg/kg YQA14, t=0.15, P>0.05; 50 mg/kg YQA14, t=0.15, P>0.05, compared to pre-test). However, an acute single injection of YQA14 produced an immediate, moderate reduction in locomotion ($F_{2,25}$=6.135, P<0.01), an effect that lasted for about 30 min.

Figures 13A, 13B:
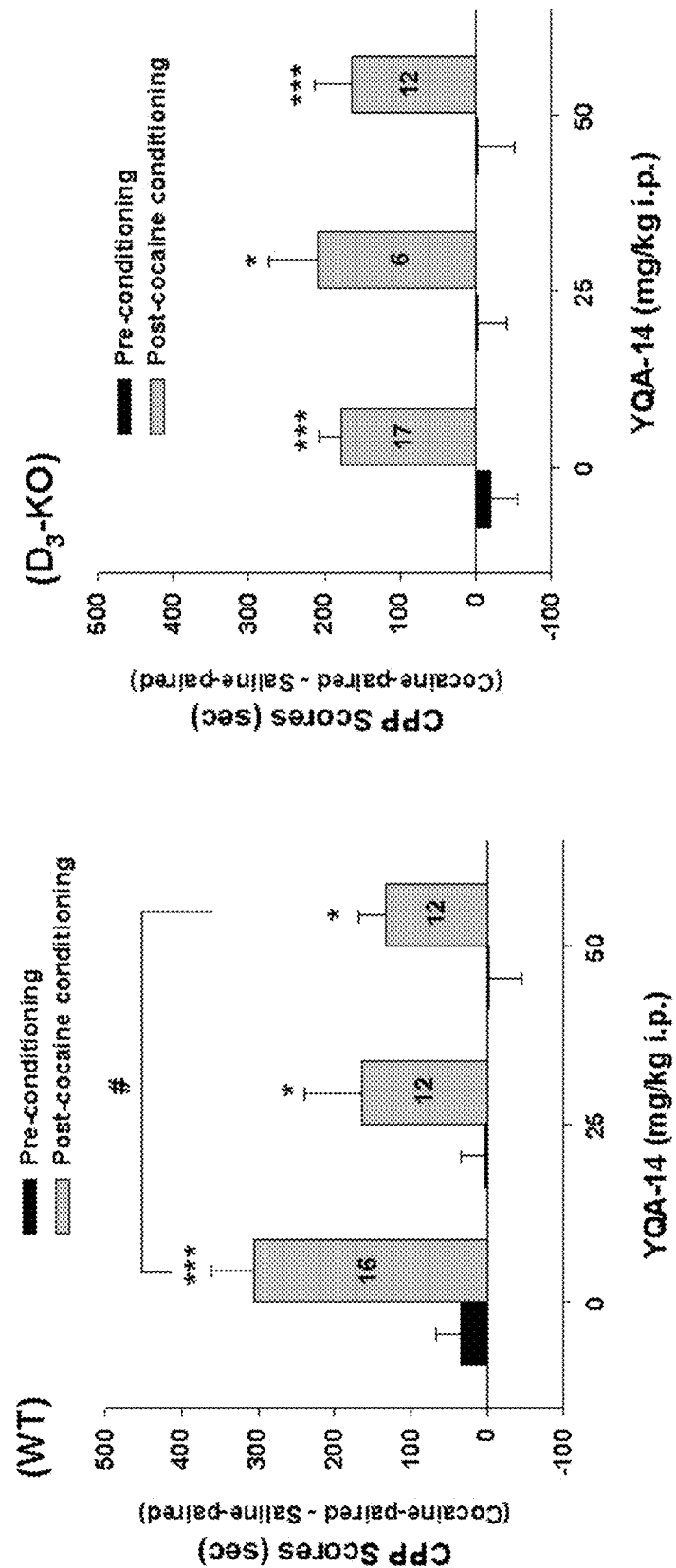
FIGS. 13A-B are graphs showing that chronic YQA14 pretreatment inhibits acquisition of cocaine-induced CPP in WT mice, but not in D3$^{-/-}$ mice.

2. Chronic YQA14 Pretreatment Inhibits Acquisition of Cocaine-Induced CPP in WT Mice, but not in $D3^{-/-}$ Mice FIG. 13 illustrates that repeated YQA14 (25 or 50 mg/kg, i.p., for 10 days) pretreatment significantly inhibited acquisition of cocaine-induced CPP in a dose-dependent manner in WT mice (one-way ANOVA, $F_{2,37}$=3.85, P<0.05), but not in $D_3^{-/-}$ mice ($F_{2,32}$=0.20, P>0.05). Post-hoc individual group comparisons revealed a statistically significant reduction in cocaine-induced CPP in WT mice after 50 mg/kg (t=6.04, P<0.05), but not 25 mg/kg (t=2.49, P>0.05), YQA14, compared to vehicle. However, in $D_3^{-/-}$ mice, 20 mg/kg cocaine produced similar levels of CPP response in the absence or presence of either dose of YQA14 pretreatment.

Figure 14B:
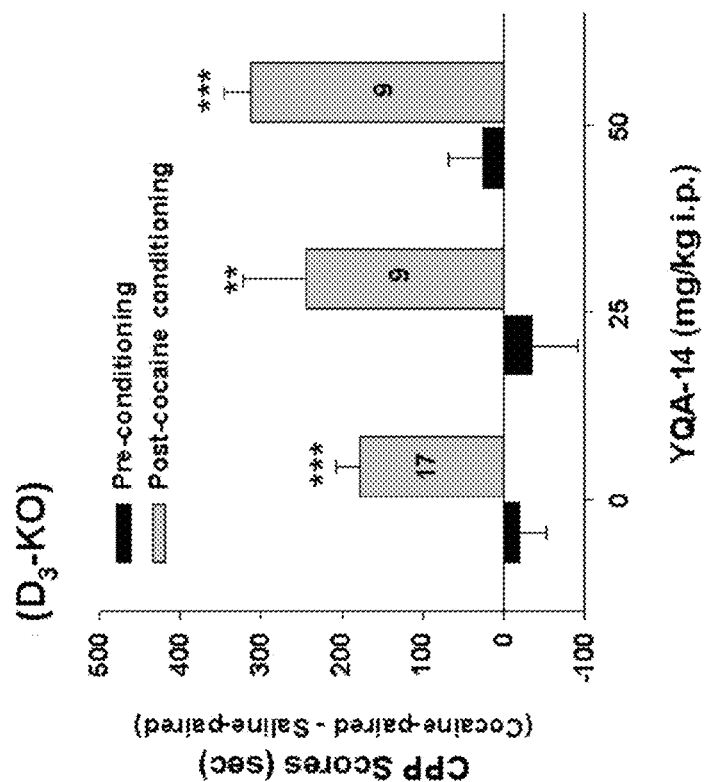
FIGS. 14A-B are graphs showing that acute YQA14 pretreatment inhibits expression of cocaine-induced CPP in WT mice, but not in D3$^{-/-}$ mice.
Figure 14A:
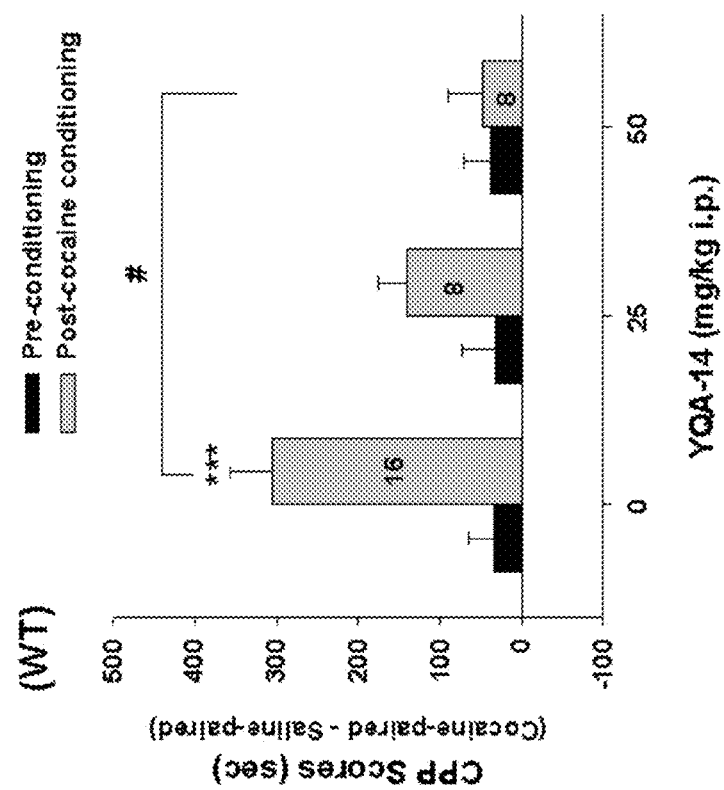

3. Acute YQA14 Pretreatment Inhibits Expression of Cocaine-Induced CPP in WT Mice, but not in $D_3^{-/-}$ Mice Then, we examined whether an acute single injection of YQA14 on the test day alters expression of cocaine-induced CPP in the two mouse strains. FIG. 14 illustrates that YQA14 (25, 50 mg/kg, 20 min before test) pretreatment significantly inhibited expression of cocaine-induced CPP only in WT (FIG. 9A, $F_{2,29}$=4.90, P<0.05), but not in $D_3^{-/-}$ mice (FIG. 9B: $F_{2,32}$=2.55, P>0.05). Cocaine, at 20 mg/kg, still produced a statistically significant increase in CPP in the presence of either dose of YQA14 pretreatment in $D_3^{-/-}$ mice.

Biological Effect Experiment 12:

Effects of YQA14 on methamphetamine-induced self-administration in rats.

The drug self-administration model presents the most obvious and face-relevant model of addiction.

Experiment Materials and Methods:

Male SD rats weighing 250-300 g were used. METH was dissolved in physiological saline. YQA14 was synthesized by the inventors and dissolved in vehicle, i.e., 25% 2-hydroxypropyl-β-cyclodextrin.

Experiment Apparatus:

Intravenous cocaine self-administration experiments were conducted in operant response test chambers (32×25×33 cm) (Med Associates, Saint Albans, Vt., USA). Each test chamber had two levers located 6.5 cm above the floor, one active and one inactive.

Experiment Procedure:

The protocol is the same as the cocaine self-administration. The doses of METH are 0.00625, 0.0125, 0.025, 0.05, 0.1 mg/kg/infusion. (See the details in the part 3: Effects of YQA14 on cocaine-induced self-administration in rats.)

Experiment Results:

1. YQA14 Inhibited METH Self-Administration Under FR2 Reinforcement in Rats

Figures 15A, 15B:
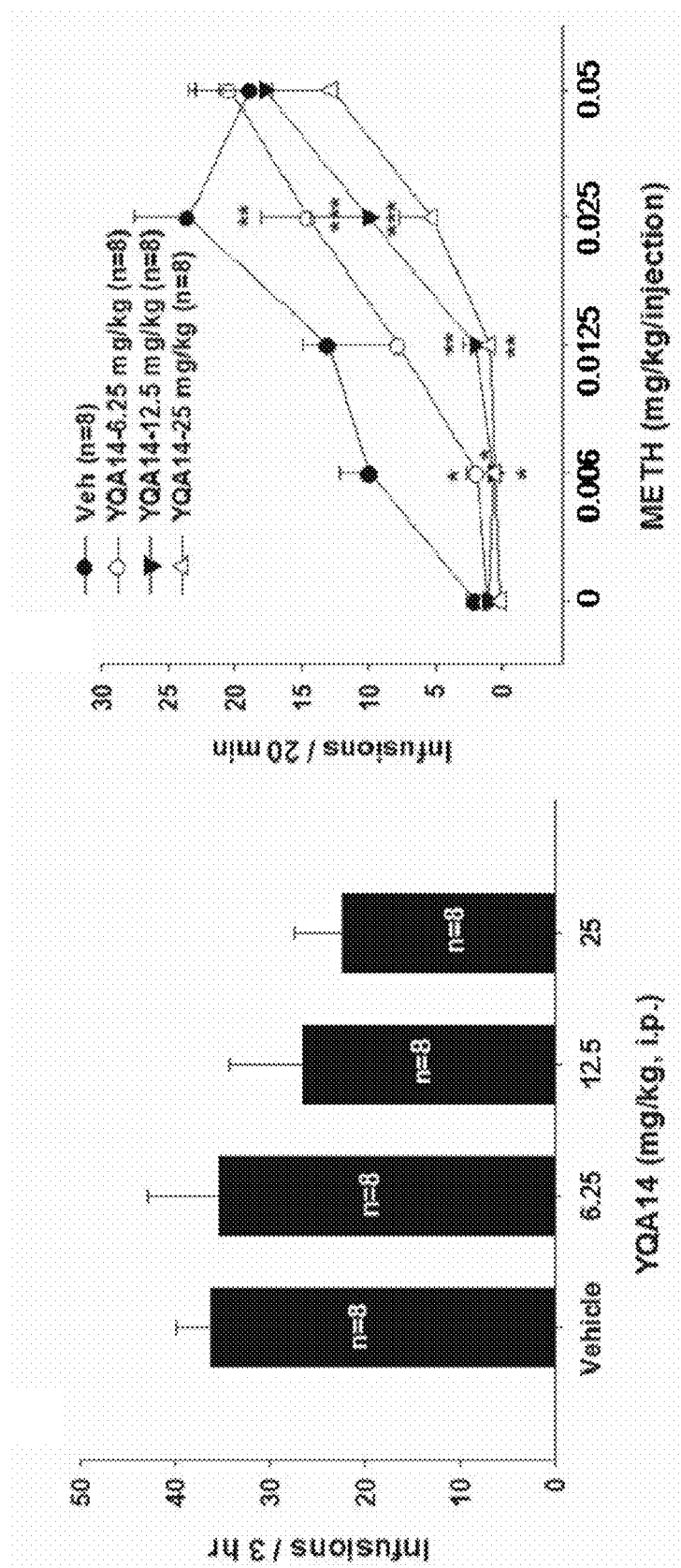
FIGS. 15A-B are graphs showing that YQA14 inhibited METH self-administration under FR2 reinforcement in rats.

FIG. 15A illustrates that systemic administration of YQA14 (6.25, 12.5, 25 mg/kg, i.p.) reduced METH self-administration behavior by 0.05 mg/kg METH, but had no significant difference ($F_{3, 31}$=1.408, P>0.05). FIG. 15B shows that YQA14, at 6.25, 12.5 or 25 mg/kg, significantly and dose-dependently attenuated METH self-administration maintained by lower doses of METH (0.006, 0.0125, 0.025 mg/kg/injection). Two-way ANOVA for repeated measures over METH dose revealed a significant treatment (vehicle vs. YQA14) main effect ($F_{3,21}$=12.282, P<0.001), significant METH dose main effect ($F_{4, 28}$=23.355, P<0.001) and a significant treatment×dose interaction ($F_{12, 159}$=1.964, P<0.05). Individual group comparisons using the Student-Newman-Keuls test revealed a statistically significant reduction in METH self-administration maintained by lower doses (0.00625, 0.0125, 0.025 mg/kg/infusion) of METH after 6.25 mg/kg (q=3.69, P<0.05), 12.5 mg/kg (q=6.122, P<0.001) or 25 mg/kg (q=8.148, P<0.001) YQA14, when compared to the vehicle control group.

2. YQA14 Inhibited METH Self-Administration Under PR Reinforcement in Rats

Figures 16A, 16B:
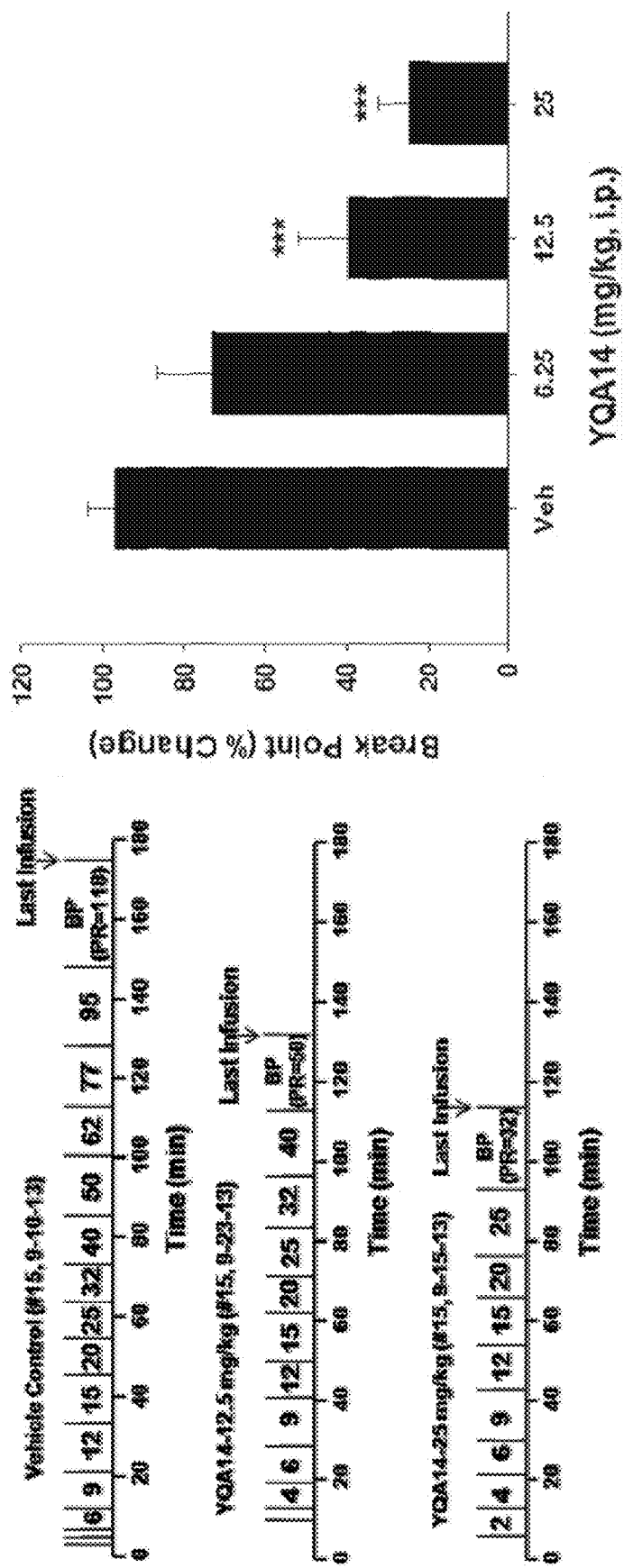
FIGS. 16A-B are graphs showing that YQA14 inhibited METH self-administration under PR reinforcement in rats.

To determine whether YQA14-induced reduction in METH self-administration was due to a reduction in METH's rewarding efficacy, we further observed the effects of YQA14 on i.v. METH self-administration under progressive-ratio (PR) reinforcement. FIG. 16A shows a representative record of one experiment animal's break point for i.v. METH under PR schedule following pretreatment with vehicle and 12.5 and 25 mg/kg of YQA14. Each vertical line indicates a METH infusion (0.05 mg/kg per infusion). The number between the vertical lines indicates the last number of PR break-point which is that active responses (PR ratio) required for a subsequent METH infusion. FIG. 16A shows reduction in PR breakpoint from 118 after pretreatment with vehicle (25% 2-hydroxypropyl-β-cyclodextrin, i.p.; upper trace) to a breakpoint of 50 and 32 following pretreatment with YQA14 (12.5, 25 mg/kg i.p. respectively, lower trace). FIG. 16B illustrates pretreatment with YQA14 significantly decreases the PR break-point (shown as % change) in a dose-related manner ($F_{3, 35}$=12.688, P<0.001, one-way ANOVA). Individual group comparisons using the Bonferroni test revealed a statistically significant reduction in break-point levers after 12.5 mg/kg (t=4.582, *P<0.001) and 25 mg/kg (t=5.503, *P<0.001) YQA14, when compared to the vehicle treated group.

Biological Effect Experiment 13:

Effects of YQA14 on Methamphetamine-triggered reinstatement of drug-seeking behavior in rats.

The drug self-administration model presents the most obvious and face-relevant model of addiction.

Experiment Materials and Methods:

Male SD rats weighing 250-300 g were used. METH was dissolved in physiological saline. YQA14 was synthesized by the inventors and dissolved in vehicle, i.e., 25% 2-hydroxypropyl-β-cyclodextrin.

Experiment Apparatus:

Intravenous cocaine self-administration experiments were conducted in operant response test chambers (32×25×33 cm$^3$) (Med Associates, Saint Albans, Vt., USA). Each test chamber had two levers located 6.5 cm above the floor, one active and one inactive.

Experiment Procedure:

The protocol is the same as the cocaine-triggered reinstatement of drug-seeking behavior in rats. The intravenous dose of METH is 0.05 mg/kg/infusion, the systemic injection of METH is 0.5 mg/kg for i.p. (See the details in the part 4: Effects of YQA14 on cocaine-triggered reinstatement in rats.)

Experiment Results:

YQA14 Inhibited the Drug-Induced METH-Seeking Behavior.

Figure 17A:
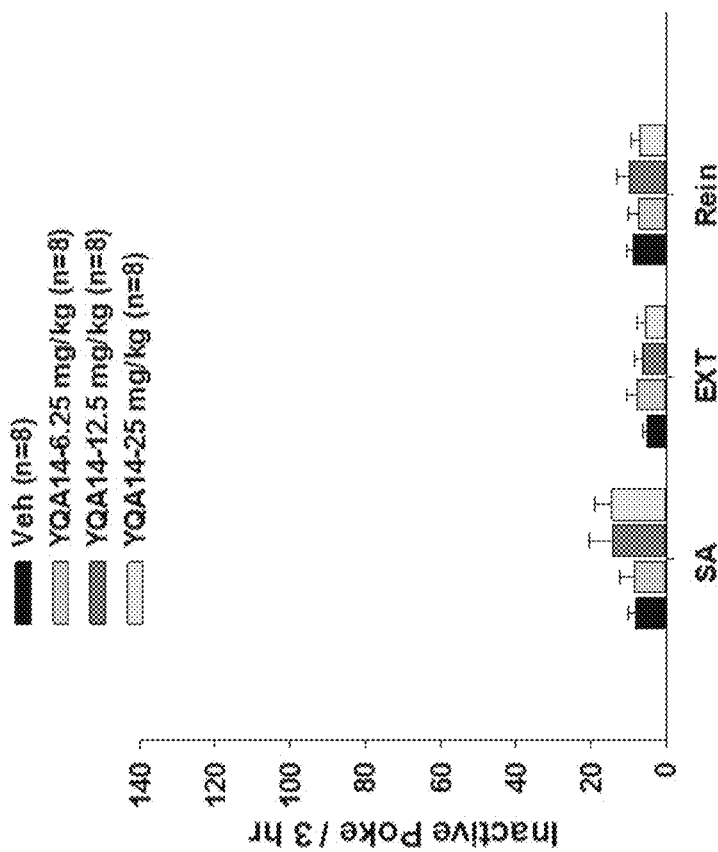
FIGS. 17A-B are graphs showing that YQA14 inhibited the drug-induced METH-seeking behavior.
Figure 17B:
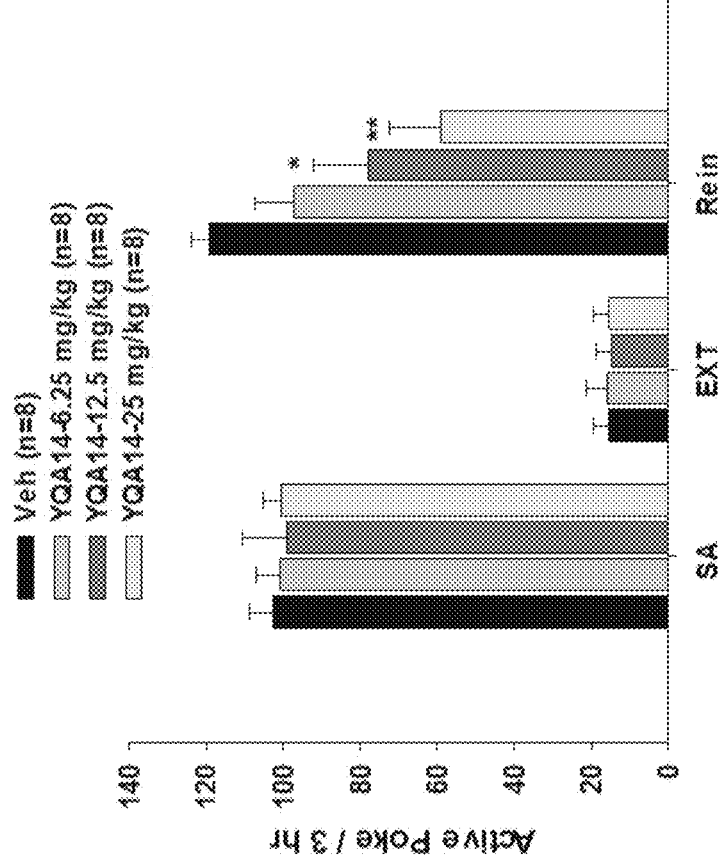

FIG. 17A illustrated the total number of active observed during the last session of METH self-administration, the last session of extinction, and the reinstatement test session in the three different YQA14 dose groups. A single, non-contingent METH prime (1 mg/kg, i.p.) evoked robust reinstatement of METH-seeking behavior in rats extinguished from previously reinforced by i.v. METH infusions. Pretreatment with YQA14 (6.25, 12.5 and 25 mg/kg, i.p.) significantly decreased METH-triggered reinstatement of drug-seeking behavior by ~50%. One-way ANOVA revealed a significant main effect of YQA14 on METH-triggered reinstatement ($F_{3, 31}$=6.068, P<0.01). Individual group comparisons indicated a statistical significant reduction in active responses during reinstatement test following pretreatment with 12.5 mg/kg YQA14 (t=3.942, *P<0.05, n=8) or 25 mg/kg YQA14 (t=5.746, **P<0.01, n=8), when compared with the vehicle pretreatment. In contrast, YQA14 pretreatment did not alter inactive lever response under the same experimental conditions (FIG. 17B, $F_{3, 31}$=0.32, P>0.05), suggesting a specific effect on METH-induced drug-seeking behavior.

Biological Effect Experiment 14:

Effects of YQA14 on Cue-triggered reinstatement of methamphetamine-seeking behavior in rats.

The drug self-administration model presents the most obvious and face-relevant model of addiction.

Experiment Materials and Methods:

Male SD rats weighing 250-300 g were used. METH was dissolved in physiological saline. YQA14 was synthesized by the inventors and dissolved in vehicle, i.e., 25% 2-hydroxypropyl-β-cyclodextrin.

Experiment Apparatus:

Intravenous cocaine self-administration experiments were conducted in operant response test chambers (32×25×33 cm$^3$) (Med Associates, Saint Albans, Vt., USA). Each test chamber had two levers located 6.5 cm above the floor, one active and one inactive.

Experiment Procedure:

The protocol is the same as the cue-triggered reinstatement of cocaine-seeking behavior in rats. (See the details in the part 5: Effects of YQA14 on cue-induced cocaine-seeking behavior in rats.)

Experiment Results:

YQA14 Inhibited the Cue-Induced METH-Seeking Behavior.

Figure 18B:
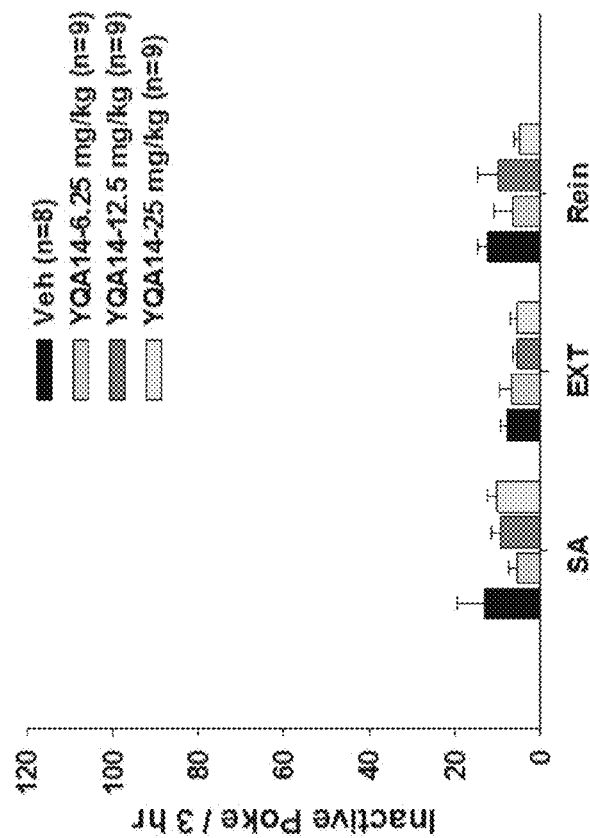
FIGS. 18A-B are graphs showing that YQA14 inhibited the cue-induced METH-seeking behavior.
Figure 18A:
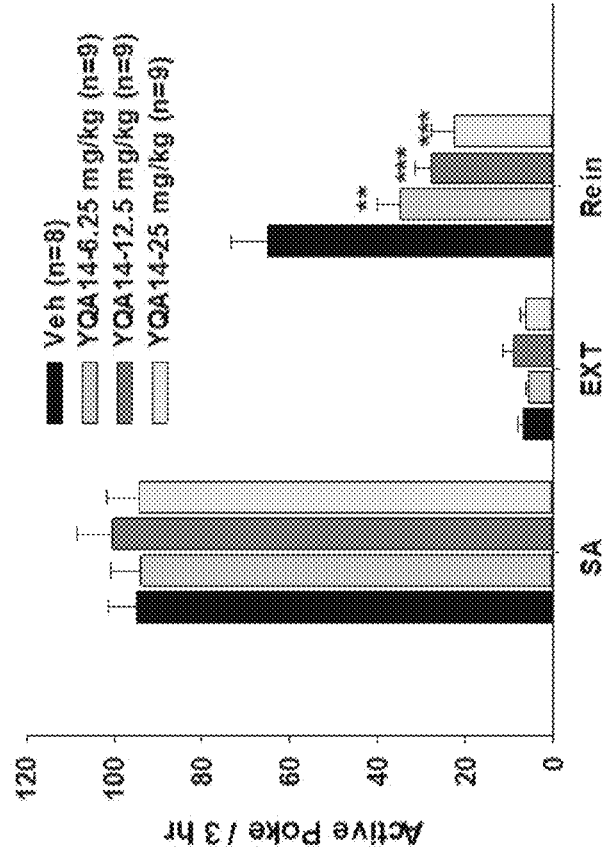

FIG. 18A shows the total number of active observed during the last session of METH self-administration, the last session of extinction, and the cue-induced reinstatement test session in the three different YQA14 dose groups. Pretreatment with YQA14 (6.25, 12.5, 25 mg/kg) on the test day significantly and dose-dependently attenuated cue-induced METH-seeking behavior. One-way ANOVA revealed a statistically significant YQA14 treatment main effect on active lever presses (FIG. 18A, $F_{3, 34}$=11.343, P<0.001). Individual group comparisons revealed a significant reduction in active lever pressing after 6.25 mg/kg (t=3.82, P<0.01), 12.5 mg/kg (t=4.722, *P<0.001) and 25 mg/kg (t=5.385, ***P<0.001), when compared to vehicle control group. In contrast, systemic administration of YQA14 did not alter inactive lever responses (FIG. 18B, $F_{3, 34}$=1.07, P>0.05), suggesting a specific effect on cue-induced drug-seeking behavior.

Biological Effect Experiment 15:

Effects of YQA14 on methamphetamine-induced conditioned place preference in mice.

Experiment Materials and Methods:

Male Kun-Ming mice (Beijing Animal Center, Beijing, China), weighting 18-20 g. Methamphetamine was dissolved in physiological saline. YQA14 was synthesized by the inventors and dissolved in vehicle, i.e., 25% 2-hydroxypropyl-β-cyclodextrin.

Experiment Apparatus:

A conventional conditioned place preference apparatus (CPP-VR01, Ningbo, China) was used. The apparatus had two equal-size compartments (25×35×64 cm$^3$) and a central tunnel (15×35×64 cm$^3$). One compartment is black with a stainless steel grid rod floor consisting of (0.3×0.3 cm$^2$) rods placed on (1.5×1.5 cm$^2$) centers. The other compartment is white with a (28.5×22.5 cm$^2$) spaced stainless steel mesh floor. The center corridor was painted black on floor and white on two laterals. Each compartment had a LED light and a camera on the top.

Experiment Procedure:

Pre-Conditioning Phase (Days 1-3):

The mice were first placed in the center corridor and allowed free access to other two compartments for 15 min daily. The time spent in each compartment was recorded. This habituation was used to eliminate the biased mice which spent over 800 sec in either compartment from this study.

METH-Induced CPP (Days 4-12):

METH conditioning was conducted for 8 days (4 drug sessions and 4 saline sessions). Each animal received METH (1 mg/kg, s.c.) or saline (10 ml/kg, i.p.) injections alternatively on each other day, and then were immediately confined in drug- or saline-paired compartments for 60 min. To observe the effects of YQA14 on acquisition of METH-induced CPP, animals were received vehicle or YQA14 (6.25, 12.5 and 25 mg/kg, i.p.) 20 min prior to each METH (1 mg/kg, i.p.) or saline (1 ml/kg, s.c.) injection during METH conditioning phase. CPP test was conducted 24 hours after the last METH injection. There was no any drug treatment on the test day. To observe the effects of YQA14 on expression of METH-induced CPP, vehicle or YQA14 (6.25, 12.5 and 25.0 mg/kg, i.p.) were given 20 min prior to CPP test in additional groups of mice without receiving chronic YQA14 treatment during METH conditioning. The mice were placed in the center corridor and were allowed free access to other two compartments for 15 min. The preference (i.e. CPP score) was calculated by subtracting the time spent in the saline-paired compartment from the time spent in the drug-paired compartment.

CPP Extinction (Days 13-22):

After the establishment of METH-induced CPP, animals underwent daily extinction training for 10 days in additional groups of mice, in which the mice received saline or YQA14, but not METH, injection, and then were confined in the previous drug-paired compartment for 60 min. The effects of chronic YQA14 on extinction response to METH-induced CPP were evaluated on day 16 and day 21 after each four-day of extinction training (FIG. 10A).

Reinstatement Test (Day 23):

After the completion of the above extinction tests, all mice received an injection of METH (0.5 mg/kg, s.c.) priming to observe METH-induced reinstatement of the CPP response after chronic vehicle or YQA14 treatment during the extinction described above.

Experiment Results:

1. Chronic YQA14 Pretreatment Did not Alter Acquisition of METH-Induced CPP

We then further examined whether repeated administration of YQA14 altered acquisition of METH-induced CPP in mice. FIG. 20 shows that METH produced robust place preference in the presence or absence of YQA14 treatment (*P<0.001, P<0.01, *P<0.05), indicating that chronic administration of YQA14 had no significant effect on the acquisition of METH-induced CPP compared with the vehicle treatment group ($F_{3, 44}$=0.109, P>0.05).

2. A Single Injection of YQA14 Inhibits Expression of METH-Induced CPP

Then, we further examined of the effect of YQA14 on expression of METH-induced CPP. FIG. 20B shows that YQA14 (6.25, 12.5, and 25 mg/kg, i.p., 20 min prior to test) pretreatment significantly attenuated METH-induced CPP in a dose-dependent manner ($F_{3, 74}$=3.34, #P<0.05). Post-hoc individual group comparisons revealed a statistically significant reduction in CPP after 12.5 mg/kg or 25 mg/kg YQA14 administration P<0.05).

3. Chronic YQA14 Facilitates Extinction of METH-Induced CPP

Before extinction training, mice did not receive any YQA14 pretreatment. METH (1 mg/kg, s.c.) produced significant CPP in the vehicle or YQA14 treatment groups compared to the responses in the pre-conditioning phase. During the extinction phase, the mice were treated daily with vehicle or YQA14 immediately before being placed into the former METH-paired compartment. FIG. 21 illustrated that repeated YQA14 pretreatment dose-dependently decreased reward-seeking during extinction, i.e., the time spent in the METH-paired compartment on the first extinction test day, compared to the vehicle treatment group ($F_{3, 90}$=2.959, P<0.05).

4. Chronic YQA14 Inhibits METH-Induced Reinstatement of METH-Induced CPP

Given that the CPP response was not completely extinguished in the first test day, we continued daily extinction with vehicle or YQA14 treatment for additional 4 days. And then, we observed the effects of chronic YQA14 treatment on METH-induced reinstatement of reward-seeking behavior.

After 8 days of extinction training, METH-induced CPP was almost completely extinguished in all vehicle or YQA14 treatment groups. On the test day METH (0.5 mg/kg, s.c.) priming induced robust reinstatement of METH-induced CPP (t=6.368, ***P<0.001), which was significantly attenuated by YQA14 (6.25, 12.5, and 25 mg/kg, i.p.) in a dose-dependent manner ($F_{3, 93}$=6.847, P<0.001). Individual group comparisons revealed a statistically significant reduction after 6.25, 12.5 and 25 mg/kg YQA14 (FIG. 21B).

Biological Effect Experiment 16:

Effects of YQA14 on methamphetamine-induced behavioral sensitization in mice.

Locomotor hyperactivity is one of the most commonly used paradigms to study drug's acute rewarding and psychostimulating effects. Behavioral sensitization has been proposed as a useful paradigm to learn the mechanism of psychostimulant addiction.

Experiment Materials and Methods:

Male Kun-Ming mice (Beijing Animal Center, Beijing, China), weighting 18-20 g. Methamphetamine was dissolved in physiological saline. YQA14 was synthesized by the inventors and dissolved in vehicle, i.e., 25% 2-hydroxypropyl-β-cyclodextrin.

Experiment Procedure:

The general procedure for sensitization was the same as described previously. Briefly, the apparatus (JLBehv-LAG-9, Shanghai, China) is a locomotor activity monitor chamber. Before receiving drug treatment, mice were placed in locomotor detection chambers for habituation for half an hour per day for 3 days. Then, mice were divided into two groups. One group of mice were used to study the effects of chronic YQA14 administration (vehicle, 6.25, 12.5, 25 mg/kg/day for 10 days, 20 min prior to METH, n=12 per dose group) on acquisition of METH (1 mg/kg/day×10 days)-induced locomotor sensitization. The second group of mice were used to study the effects of a single dose of YQA14 (0, 6.25, 12.5, 25 mg/kg, n=12 per dose group) on expression of METH (0.5 mg/kg)-induced locomotor sensitization in mice 7 days after the last METH injection. After each METH injection, animals were immediately placed into the locomotion chambers to record locomotor behavior for 2 hours. All data were recorded via a computerized video tracking system (Jiliang Software Co. Ltd., Shanghai, China). The travel distance was used to evaluate the effects of YQA14 on locomotor behavior.

Experiment Results:

1. Chronic YQA14 Inhibits Acquisition of METH-Induced Behavioral Sensitization

Figure 22A:
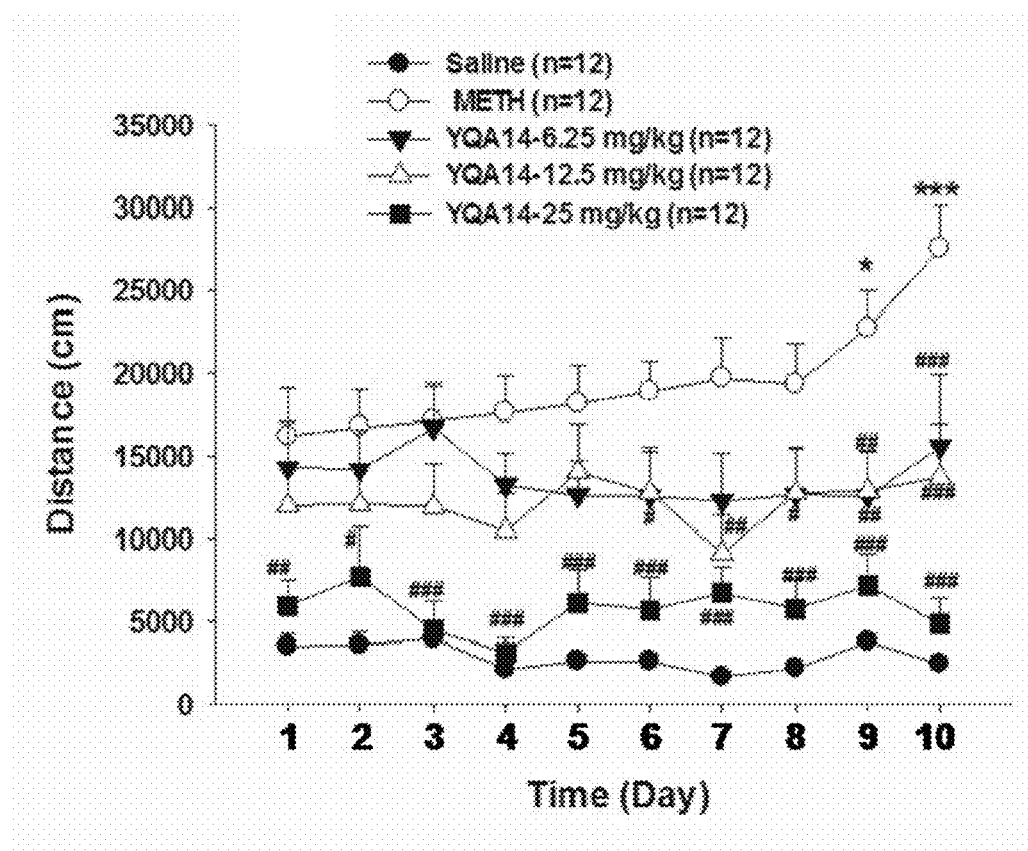
FIGS. 22A-B are graphs showing that chronic YQA14 inhibits acquisition of METH-induced behavioral sensitization.
Figure 22B:
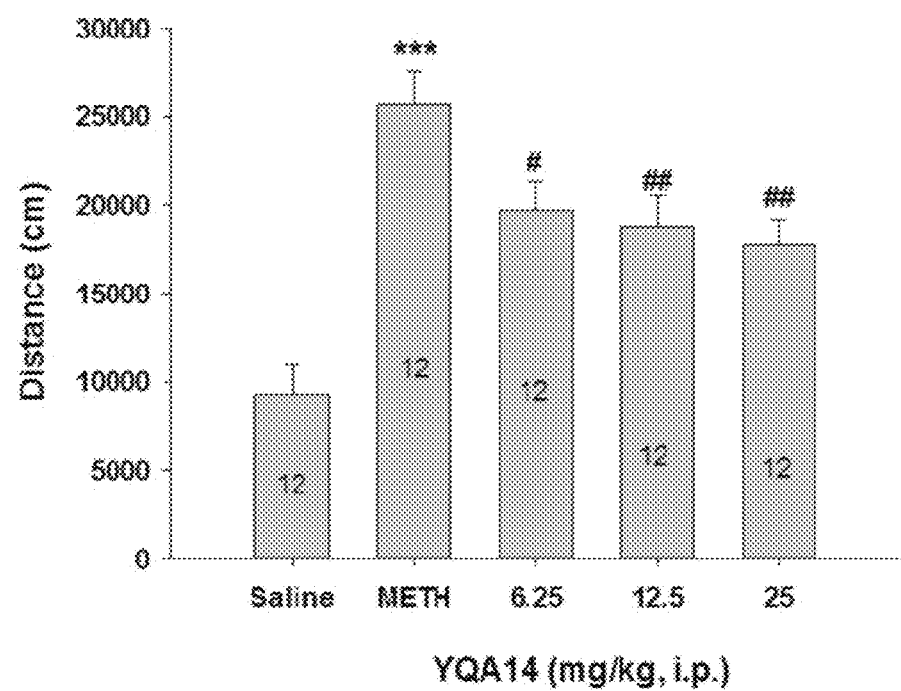

FIG. 22B shows the effects of repeated METH administration (1 mg/kg, s.c.) on locomotor behavior in the presence or absence of YQA14, illustrating that chronic METH treatment produced significant behavioral sensitization (*P<0.05, *P<0.001, compared with day 1) in METH group mice. Chronic YQA14 treatment significantly attenuated the acquisition of METH-induced behavioral sensitization. Two-way ANOVA for repeated measures revealed a significant YQA14 treatment main effect ($F_{4, 54}$=14.22, P<0.001), time main effect ($F_{9, 486}$=2.83, P=0.003), and treatment×time interactions ($F_{36, 589}$=1.998 P<0.001). Post-hoc individual group comparisons revealed a significant difference between YQA14 and vehicle treatment groups at each time point (#P<0.05, ##P<0.01, ###P<0.001). FIG. 6C shows, on the challenge day, METH (0.5 mg/kg, s.c.) produced a significantly increase in locomotion only in METH group, but not in any YQA14 treatment groups (*P<0.001, compare with saline group). One-way ANOVA measures revealed a significant YQA14 treatment main effect ($F_{4, 44}$=4.752, P<0.01), Post-hoc individual group comparisons revealed a significant difference between YQA14 and METH treatment group at each dose (#P<0.05, ##P<0.01).

Figure 23B:
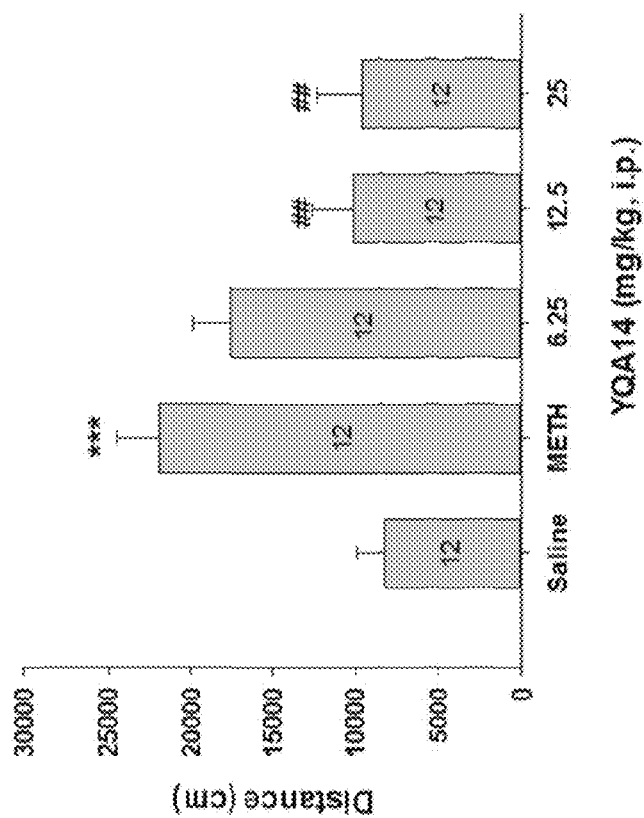
FIGS. 23A-B are graphs showing that YQA14 inhibits expression of METH-induced behavioral sensitization.
Figure 23A:
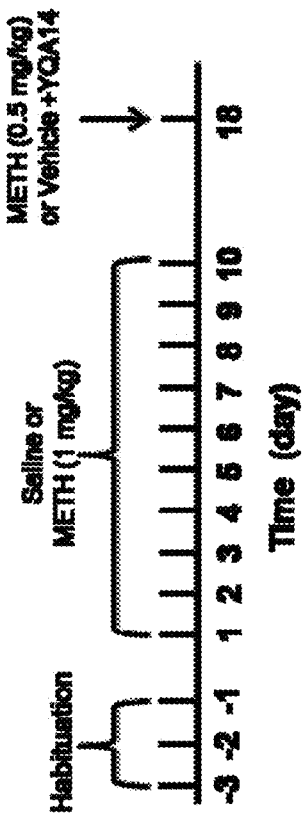

2. A Single Injection of YQA14 Inhibits Expression of METH-Induced Behavioral Sensitization FIG. 23B showed that METH (0.5 mg/kg, s.c.) priming produced a significantly enhanced locomotor response in the vehicle treatment group (t=4.699, ***P<0.001).

However, a single administration of YQA14 pretreatment significantly attenuated expression of METH-induced locomotor sensitization ($F_{3, 44}$=6.454, *P<0.001) in a dose-dependent manners. Individual group comparisons revealed a statistically significant reduction after 12.5 mg/kg or 25 mg/kg YQA14 (P<0.01).

Biological Effect Experiment 17:

Effects of YQA14 on morphine-induced conditioned place preference in rats. (Hu et al., "YQA14: dopamine D3 receptor antagonist that inhibits the expression and drug-primed reactivation of morphine-induced conditioned place preference in rats," European Journal of Pharmacology, 2013 Oct. 24. pii: S0014-2999 (13)00782-6. doi: 10.1016/j.ejphar.2013.10.026. [Epub ahead of print])

Experiment Materials and Methods:

Male Sprague-Dawley rats (Beijing Animal Center, Beijing, China) that weighted 200-250 g. Morphine hydrochloride (Qinghai Pharmaceutical Factory, Xining, China), was dissolved in physiological saline. YQA14 was synthesized by the Beijing Institute of Pharmacology and Toxicology, and was dissolved in vehicle, i.e. 2-hydroxypropyl-β-cyclodextrin (Xi'an Deli Biologic & Chemical Industry Co., Ltd. Xi'an, China).

Experiment Apparatus:

Conditioned place preference procedure. A conventional CPP apparatus (CPP-VR01, AniLab Instrument Co., Ltd, Ningbo, China) was used in this study. The apparatus had two compartments of equal-size (25 cm×35 cm×64 cm) and a central tunnel (15 cm×35 cm×64 cm) that was connected to the two compartments via a guillotine baffle. One compartment was black with a stainless steel grid rod floor consisting of rods (0.3 mm diameter) placed 1.5 cm apart. The other compartment was white with a 28.5 cm×22.5 cm spaced stainless steel mesh floor. The center corridor had a black on floor and white walls. Each compartment had a LED light and a camera on the top. All data were recorded via a computerized video tracking system (AniLab v 2.43, AniLab Software & Instrument Co. Ltd., Ningbo, China).

Experiment Procedure:

Pre-Conditioning Phase (Day 1-Day 3).

The rats were given free access to all compartments of the apparatus for 15 min. Drug or saline-paired compartments and treatments were assigned in a counterbalanced manner within each group.

Conditioning Training and Test Phase (Day 4-Day 12).

Conditioning training was conducted for 8 days (4 drug sessions and 4 saline sessions). Rats received morphine (10 mg/kg, subcutaneous, s.c.) or saline (10 ml/kg, s.c.) injections and were confined in drug- or saline-paired compartments for 45 min. The CPP test was conducted on day 12. The rats were placed in the center corridor and were provided free access to the other two compartments for 15 min. The preference (i.e., the CPP score) was assigned a value based by subtracting the time spent in the saline-paired compartment from the time spent in the drug-paired compartment.

Extinction Training and Test Phase (Day 13-Day 21).

The extinction and test phase was conducted for another 9 days (4 drug replacement sessions, 4 saline sessions, and a test session). In the extinction training session, the rats received an injection of saline or YQA14 to replace morphine training and were confined in the previous drug-paired compartment for 45 min. The test was conducted 24 hours after the last trial (day 21). The process was as the same as the conditioning test.

Reactivation Test Phase (Day 22).

After extinction training, all the rats were given an injection of morphine (5 mg/kg, s.c.) and were immediately placed in the central tunnel with free access to the other chambers for 15 min.

1. To test the effect of YQA14 on the acquisition of morphine-induced CPP, naive rats received a vehicle injection (n=12) or YQA14 (12.5, 25.0 and 50.0 mg/kg, i.p., n=8-11 per dose) injection 20 min before the administration of morphine (10 mg/kg, s.c.) or saline (10 ml/kg, s.c.) in conditioning training. The CPP test was conducted 24 hours after the last training trial. On the test day, the rats did not receive any injections.

2. To investigate the effect of YQA14 on the expression of morphine-induced CPP, naive rats received morphine (10 mg/kg, s.c.) or saline (10 ml/kg, s.c.) injections and were confined in the drug- or saline-paired compartments for 45 min alternating days for 8 days. On the test day, the trained rats were divided into four groups, including vehicle (n=16) or YQA14 (6.25, 12.5 and 25.0 mg/kg, i.p., n=13-15 per dose) injections were administered 20 min before the CPP test.

3. To examine the effects of YQA14 on reactivation of morphine-induced CPP, naive rats received conditioning training for 8 days, and extinction training was conducted after CPP testing. During the extinction trials, all the rats were given a vehicle injection (1 ml/kg, i.p.) 20 min before being placed in a saline-paired compartment. The rats were injected with vehicle (n=12) or YQA14 injection (6.25, 12.5 and 25 mg/kg, i.p., n=19-22 per dose) 20 min before being placed in a morphine-paired compartment. Tests for extinction and reactivation were conducted. In the reactivation test, the rats only receive morphine (5 mg/kg, s.c.) and no YQA14 pretreatment.

Figure 24:
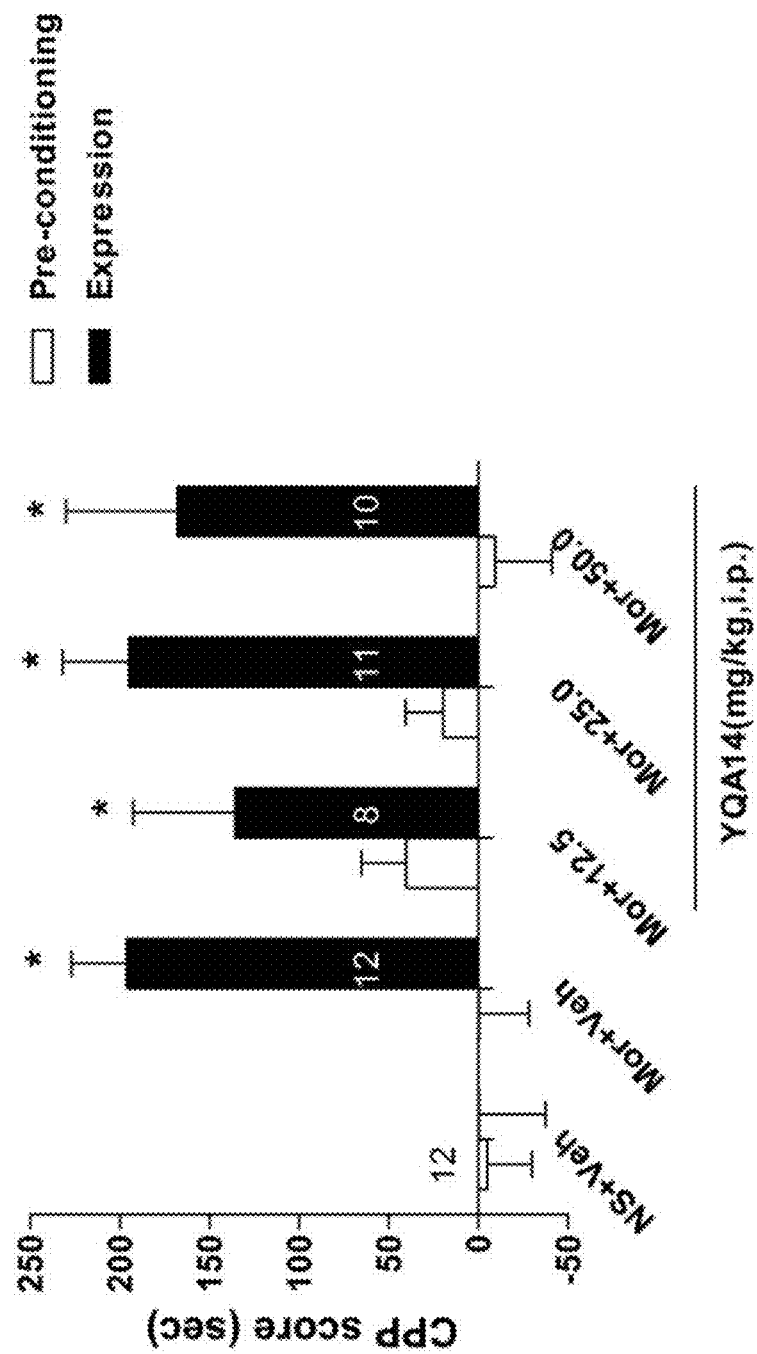
FIG. 24 is a graph showing that YQA14 had no effect on the acquisition of morphine-induced CPP in rats.

Experiment Results:

1. YQA14 had no effect on the acquisition of morphine-induced CPP in rats. We investigated whether repeated YQA14 (12.5, 25 and 50 mg/kg, i.p., for 4 days) pretreatment on the conditioning days altered the acquisition of morphine-induced CPP. FIG. 24 shows that morphine (10 mg/kg, s.c.) robustly induced preference in the morphine group compared with the saline group (t=4.071, P=0.0005); however, the chronic administration of YQA14 did not significantly influence the acquisition of morphine-induced CPP compared with morphine group (F3, 74=0.207, P=0.891).

Figure 25:
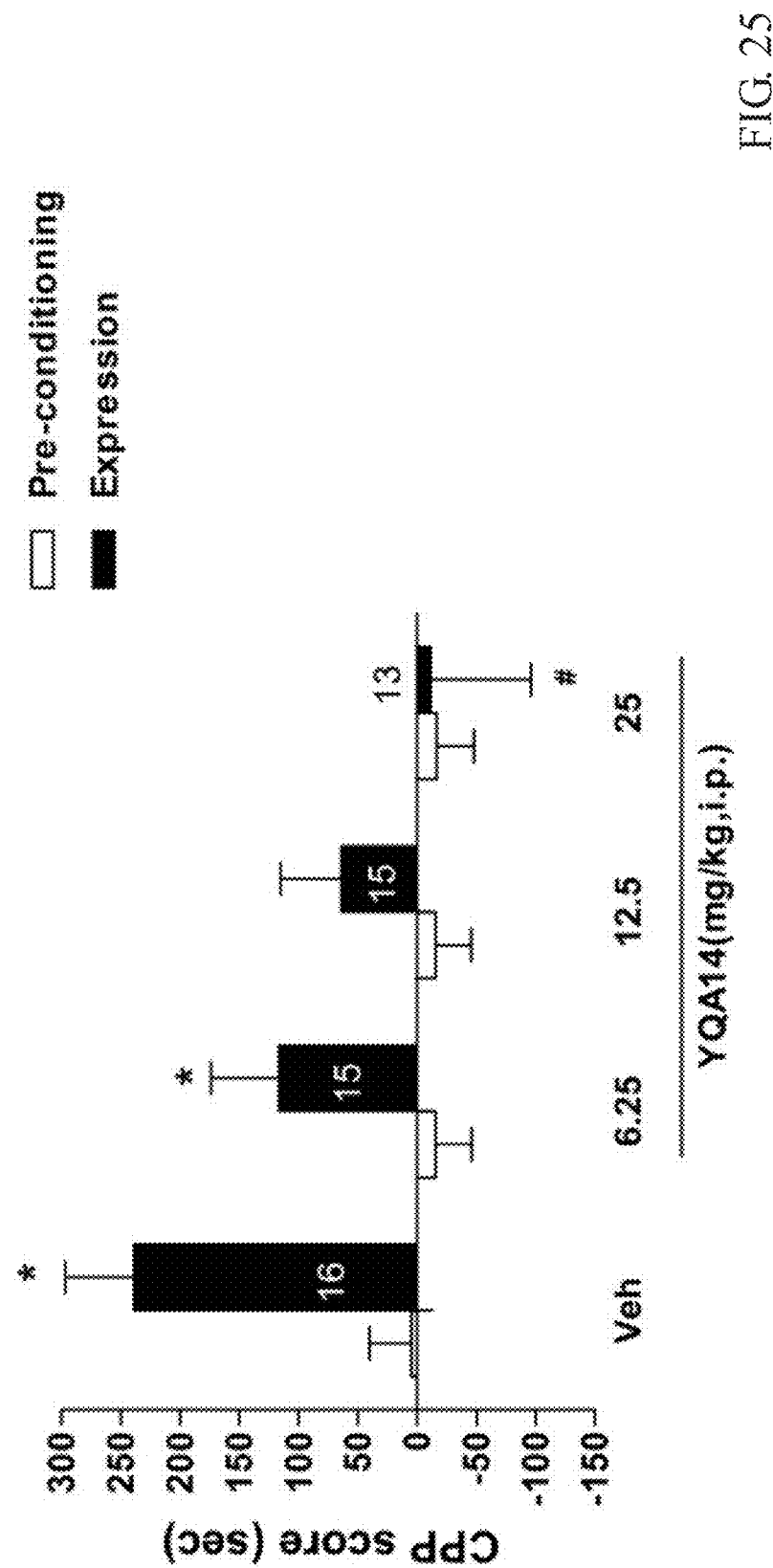
FIG. 25 is a graph showing that YQA14 attenuated the expression of morphine-induced CPP in rats.

2. YQA14 attenuated the expression of morphine-induced CPP in rats. We investigated whether an acute single injection of YQA14 on the test day altered the morphine-induced CPP responses. FIG. 25 illustrates that compared with vehicle injection, YQA14 (6.25, 12.5 and 25 mg/kg, i.p.) decreased the CPP scores in a dose-related manner compared with the vehicle injections (F3, 54=2.890, P=0.044). At 25 mg/kg, YQA14 produced a statistically significant reduction in the expression of morphine-induced CPP (t=2.819, P<0.05; Holm-Sidak post-hoc test).

3. YQA14 inhibited the reactivation of morphine-induced CPP in rats.

Figure 26B:
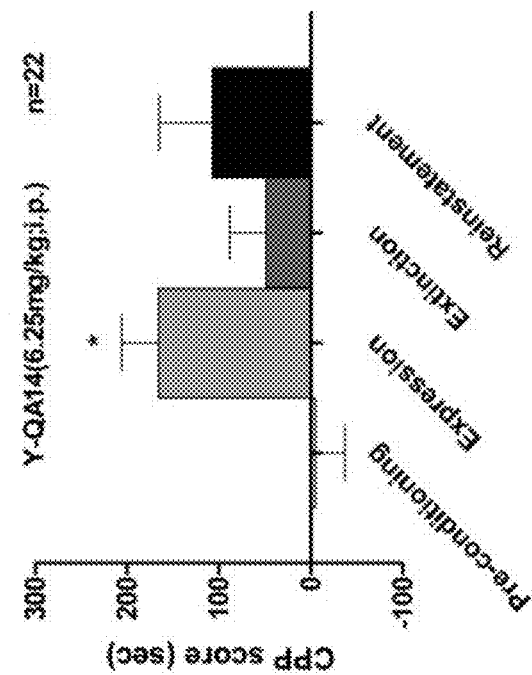
Figure 26A:
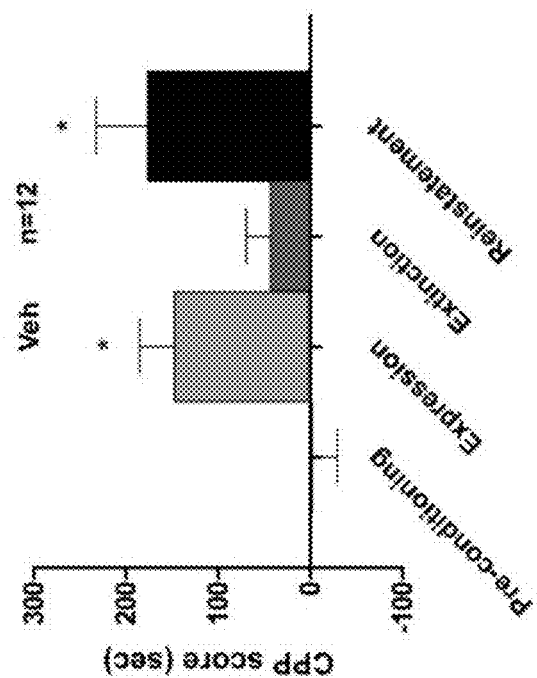

We replaced morphine with YQA14 (6.25, 12.5 and 25 mg/kg, i.p.) or vehicle treatment in the drug-paired compartment on the extinction training days. All the rats were given only a morphine (5 mg/kg, s.c.) injection on the reactivation test day. In FIG. 26, the YQA14 groups (6.25, 12.5 and 25 mg/kg, i.p.) exhibited a dose-related manner decreased in morphine-induced reactivation. At 25 mg/kg, the reduction was statistically significance (in FIG. 26D) (t=1.838, P=0.038, t-test). Before extinction training, the rats did not receive YQA14 pretreatment. Morphine (10 mg/kg, s.c.) induced significant activation of CPP in the vehicle group (t=5.098, P=0.0003) and in the groups that received 6.25, 12.5 and 25 mg/kg of YQA14 (t=5.654, P<0.0001; t=5.512, P<0.0001; t=4.580, P=0.0002; respectively) compared with their respective pre-conditioning phases. After 8 days of extinction training, morphine-induced CPP was completely extinct in all the groups (in FIG. 9). On the test day for reactivation, the preference was recovered only in the vehicle group when the rats were given morphine (5 mg/kg, s.c.) injections (t=3.094, P=0.0102). These results indicate that YQA14 deterred the drug-primed reactivation.

Biological Effect Experiment 18:

Effects of YQA14 and YQA31 on heroin-induced self-administration in rats.

The drug self-administration model presents the most obvious and face-relevant model of addiction.

Experiment Materials and Methods:

Male SD rats weighing 250-300 g were used. METH was dissolved in physiological saline. YQA14 and YQA31 was synthesized by the inventors and dissolved in vehicle, i.e., 25% 2-hydroxypropyl-β-cyclodextrin.

Experiment Apparatus:

Intravenous cocaine self-administration experiments were conducted in operant response test chambers (32×25×33 cm) (Med Associates, Saint Albans, Vt., USA). Each test chamber had two levers located 6.5 cm above the floor, one active and one inactive.

Experiment Procedure:

The protocol is the same as the cocaine self-administration. The doses of Heroin are 0.05, 0.1 mg/kg/infusion. (See the details in the part 3: Effects of YQA14 on cocaine-induced self-administration in rats.)

Experiment Results:

1. YQA14 Inhibited Heroin Self-Administration Under FR2 Reinforcement in Rats

Figure 27:
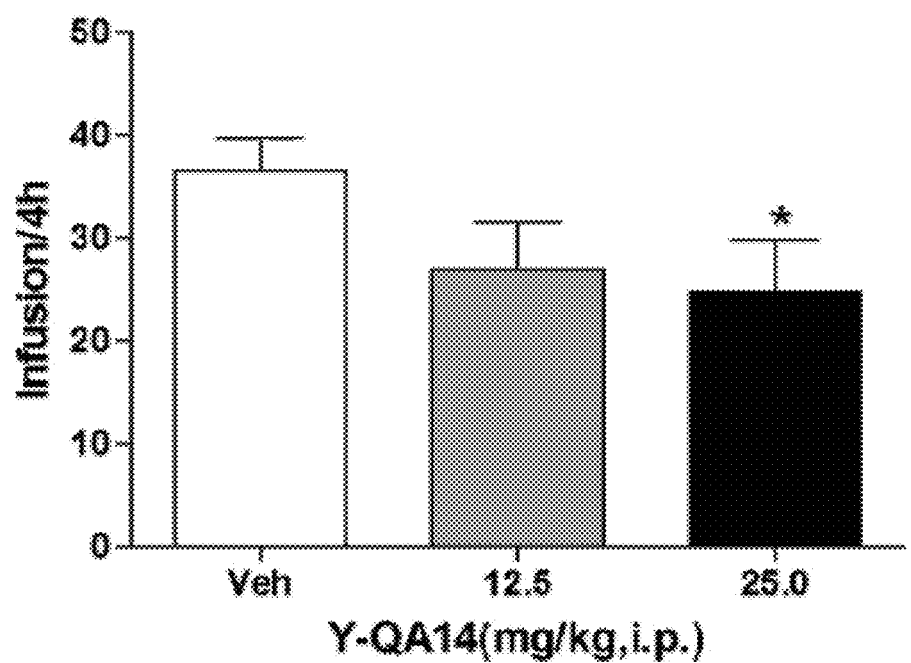
FIG. 27 is a graph showing that YQA14 inhibited Heroin self-administration under FR2 reinforcement in rats.

FIG. 27 illustrates that systemic administration of YQA14 (12.5, 25 mg/kg, i.p.) significantly reduced Heroin self-administration behavior by 0.05 mg/kg Heroin (P<0.05). Individual group comparisons using the Student-Newman-Keuls test revealed a statistically significant reduction in Heroin self-administration maintained after 25 mg/kg (P<0.05) YQA14, when compared to the vehicle control group.

2. YQA31 Inhibited Heroin Self-Administration Under FR5 Reinforcement in Rats

Figure 28:
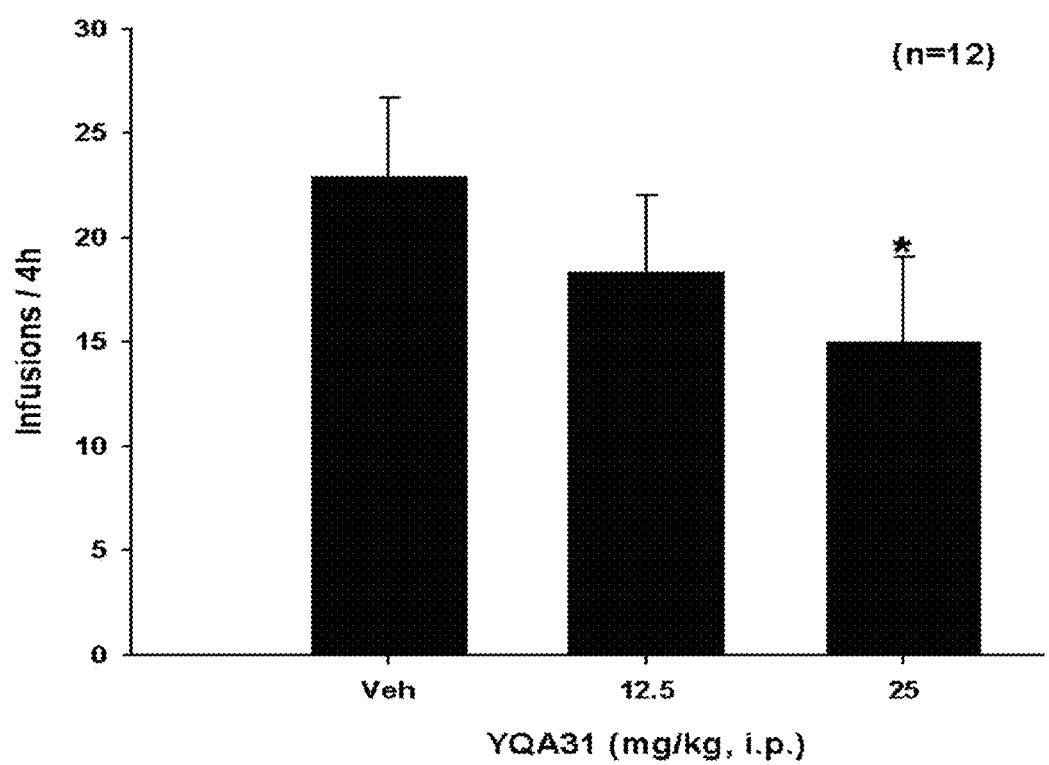
FIG. 28 is a graph showing that YQA31 inhibited Heroin self-administration under FR5 reinforcement in rats.

FIG. 28 illustrates that systemic administration of YQA31 (12.5, 25 mg/kg, i.p.) significantly reduced Heroin self-administration behavior by 0.05 mg/kg Heroin (P<0.05). Individual group comparisons using the Student-Newman-Keuls test revealed a statistically significant reduction in Heroin self-administration maintained after 25 mg/kg (P<0.05) YQA31, when compared to the vehicle control group.

THE REFERENCE

1. R Song, R-F Yang, N Wu, R-B Su, J Li, X-Q Peng, X Li, J Gaál, Z-X Xi, E L Gardner. YQA14: A novel dopamine D3 receptor antagonist that inhibits cocaine self-administration in rats and mice, but not in D3-knockout mice. *Addiction Biology*, 2012, 17 (2):259-73.
2. R Song, H-Y Zhang, X-Q Peng, R-B Su, R-F Yang, J Li, Z-X Xi, E L Gardner. Dopamine D3 receptor deletion or blockade attenuates cocaine-induced conditioned place preference in mice. *Neuropharmacology*, 2013, (7) 82-87.
3. R Song, G-H Bi, H-Y Zhang, R-F Yang, E L Gardner, J Li, Z-X Xi. Blockade of D3 Receptors by YQA14 Inhibits Cocaine's Rewarding Effects and Relapse to Drug-Seeking Behavior in Rats. *Neuropharmacology,* 2014 February; 77:398-405. doi: 10.1016/j.neuropharm. 2013.10.010. Epub 2013 Oct. 28.

4. R-R Hu, R Song, R-B Su, J Li. YQA14: dopamine D3 receptor antagonist that inhibits the expression and drug-primed reactivation of morphine-induced conditioned place preference in rats. *European Journal of Pharmacology,* 2013 Oct. 24. pii: S0014-2999 (13)00782-6. doi: 10.1016/j.ejphar.2013.10.026. [Epub ahead of print]

What is claimed is:

1. A method for treating a drug addiction selected from heroin addiction, cocaine addiction and methamphetamine addiction, comprising administering to a subject in a need thereof a therapeutically effective amount of the compound N-{4-[4-(5-chloro-2-methylphenyl)piperazinyl]butyl}-benzoxazolin-2-one-5-carboxamide or a tautomer, racemate, optical isomer, or pharmaceutically acceptable salt thereof.

2. The method of claim 1, wherein the drug addiction is heroin addiction.

3. The method of claim 1, wherein the drug addiction is cocaine addiction.

4. The method of claim 1, wherein the drug addiction is methamphetamine addiction.

* * * * *